(12) United States Patent
Law et al.

(10) Patent No.: US 8,337,838 B2
(45) Date of Patent: *Dec. 25, 2012

(54) ANTI-CD70 ANTIBODY AND ITS USE FOR THE TREATMENT AND PREVENTION OF CANCER AND IMMUNE DISORDERS

(75) Inventors: Che-Leung Law, Shoreline, WA (US); Julie McEarchern, Mill Creek, WA (US); Alan F. Wahl, Mercer Island, WA (US)

(73) Assignee: Seattle Genetics, Inc., Bothell, WA (US)

( * ) Notice: Subject to any disclaimer, the term of this patent is extended or adjusted under 35 U.S.C. 154(b) by 363 days.

This patent is subject to a terminal disclaimer.

(21) Appl. No.: 12/370,151

(22) Filed: Feb. 12, 2009

(65) Prior Publication Data

US 2009/0232806 A1 Sep. 17, 2009

Related U.S. Application Data

(63) Continuation of application No. 11/735,365, filed on Apr. 13, 2007, now Pat. No. 7,641,903, which is a continuation-in-part of application No. 11/251,173, filed on Oct. 14, 2005, now Pat. No. 7,491,390.

(60) Provisional application No. 60/645,355, filed on Jan. 19, 2005, provisional application No. 60/619,018, filed on Oct. 15, 2004.

(51) Int. Cl.
*A61K 39/395* (2006.01)

(52) U.S. Cl. .................................. 424/130.1; 424/141.1

(58) Field of Classification Search ........................ None
See application file for complete search history.

(56) References Cited

U.S. PATENT DOCUMENTS

| | | |
|---|---|---|
| 5,530,101 A | 6/1996 | Queen |
| 5,573,924 A | 11/1996 | Beckmann et al. |
| 5,618,920 A | 4/1997 | Robinson et al. |
| 6,214,345 B1 | 4/2001 | Firestone et al. |
| 6,342,219 B1 | 1/2002 | Thorpe et al. |
| 6,884,869 B2 | 4/2005 | Senter et al. |
| 7,091,186 B2 | 8/2006 | Senter et al. |
| 7,098,308 B2 | 8/2006 | Senter et al. |
| 7,256,257 B2 | 8/2007 | Doronina et al. |
| 7,261,892 B2 | 8/2007 | Terrett |
| 7,491,390 B2 | 2/2009 | Law et al. |
| 7,641,903 B2 | 1/2010 | Law et al. |
| 7,662,387 B2 | 2/2010 | Law et al. |
| 2002/0168360 A1 | 11/2002 | Dingivan et al. |
| 2003/0083263 A1 | 5/2003 | Doronina et al. |
| 2003/0130189 A1 | 7/2003 | Senter et al. |
| 2004/0180002 A1 | 9/2004 | Young |
| 2005/0118656 A1 | 6/2005 | Terrett |
| 2005/0123547 A1 | 6/2005 | Terrett |
| 2005/0191299 A1 | 9/2005 | Swamy et al. |
| 2005/0238649 A1 | 10/2005 | Doronina et al. |
| 2005/0282168 A1 | 12/2005 | Liu et al. |
| 2006/0074008 A1 | 4/2006 | Senter et al. |
| 2006/0083736 A1 | 4/2006 | Law et al. |
| 2006/0233794 A1 | 10/2006 | Law et al. |
| 2007/0292422 A1 | 12/2007 | Law et al. |
| 2008/0025989 A1 | 1/2008 | Law et al. |
| 2008/0138341 A1 | 6/2008 | Law et al. |
| 2008/0138343 A1 | 6/2008 | Law et al. |
| 2008/0226657 A1 | 9/2008 | Doronina et al. |
| 2008/0248051 A1 | 10/2008 | Doronina et al. |
| 2008/0248053 A1 | 10/2008 | Doronina et al. |
| 2009/0047296 A1 | 2/2009 | Doronina et al. |
| 2009/0074772 A1 | 3/2009 | Law et al. |
| 2009/0148942 A1 | 6/2009 | McDonagh et al. |
| 2010/0129362 A1 | 5/2010 | Law et al. |
| 2010/0150925 A1 | 6/2010 | Law et al. |
| 2010/0158910 A1 | 6/2010 | Law et al. |
| 2010/0183636 A1 | 7/2010 | Law et al. |

FOREIGN PATENT DOCUMENTS

| | | |
|---|---|---|
| EP | 1 594 542 A2 | 9/2004 |
| EP | 1 799 262 A2 | 4/2006 |
| EP | 1 871 418 A2 | 10/2006 |
| WO | WO 01/94629 A2 | 12/2001 |
| WO | WO 02/088172 A2 | 11/2002 |
| WO | WO 03/026577 A2 | 4/2003 |
| WO | WO 03/046581 A2 | 6/2003 |
| WO | WO 2004/010957 A2 | 2/2004 |
| WO | WO 2004/073656 A2 | 9/2004 |
| WO | WO2004/104045 A1 | 12/2004 |
| WO | WO 2005/081711 A2 | 9/2005 |
| WO | WO 2006/044643 A2 | 4/2006 |
| WO | WO 2006/113909 A2 | 10/2006 |
| WO | WO 2007/038637 A2 | 4/2007 |
| WO | WO 2008/074004 A2 | 6/2008 |

OTHER PUBLICATIONS

U.S. Appl. No. 11/833,954, pending, filed Feb. 19, 2009, Doronina et al.
U.S. Appl. No. 11/912,096, pending, filed Jun. 11, 2009, McDonagh et al.
U.S. Appl. No. 12/265,451, pending, filed Mar. 19, 2009, Law et al.
Adam, et al. "CD70 (TNFSF7) is expressed at high prevalence in renal cell carcinomas and is rapidly internalised on antibody binding" *British J. of Cancer*. 95:298-306 (2006).
Agathanggelou et al., "Expression of immune regulatory molecules in Epstein-Barr virus-associated nasopharyngeal carcinomas with prominent lymphoid stroma. Evidence for a functional interaction between epithelial tumor cells and infiltrating lymphoid cells," *Am J. Pathol.* 147(4):1152-1160 (1995).
Agematsu et al., "B cell subpopulations separated by CD27 and crucial collaboration of CD27+ B cells and helper T cells in immunoglobulin production," *Eur. J. Immunol.* 27(8):2073-2079 (1997).

(Continued)

*Primary Examiner* — Misook Yu
*Assistant Examiner* — Mark Halvorson
(74) *Attorney, Agent, or Firm* — Alston & Bird LLP

(57) ABSTRACT

Disclosed are CD70 binding agents, such as anti-CD70 antibodies and derivatives, that induce a cytotoxic, cytostatic or immunomodulatory without conjugation to a therapeutic agents as well as pharmaceutical compositions and kits comprising the antibody or derivative. Also disclosed are methods for the treatment and prevention of CD70-expressing cancers and immunological disorders comprising administering the CD70 binding agents to a subject.

28 Claims, 20 Drawing Sheets

OTHER PUBLICATIONS

Agematsu et al., "Generation of plasma cells from peripheral blood memory B cells: synergistic effect of interleukin-10 and CD27/CD70 interaction " *Blood.* 91(1):173-180 (1998).
Akiba et al., "Critical contribution of OX40 ligand to T helper cell type 2 differentiation in experimental leishmaniasis," *J. Exp. Med.* 191(2):375-380 (2000).
Baert, et al., "Influence of Immunogenicity on the Long-Term Efficacy of Infliximab in Crohn's Disease" *N. Engl J Med.* 348(7):601-608 (2003).
Bahler et al., "Antigen selection in human lymphomagenesis," *Cancer Res.* 52(19 Suppl.):5547s-5551s (1992).
Bahler et al., "Clonal evolution of a follicular lymphoma: evidence for antigen selection," *PNAS.* 89(15):6770-6774.
Bowman et al., "The cloning of CD70 and its identification as the ligand for CD27" *J. Immunol.* 152(4):1756-1761.
Brugnoni et al., "CD70 expression on T-cell subpopulations: study of normal individuals and patients with chronic immune activation," *Immunol. Lett.* 55(2):99-104 (1997).
Carter, P., "Improving the Efficacy of Antibody-Based Cancer Therapies," *Nature Reviews.* (1):118-129 (2001).
Casset, et al., "A peptide mimetic of an anti-CD4 monoclonal antibody of rational design" *Biochem. Biophys. Res.* 307:198-205 (2003).
Chen et al., "Selection and Analysis of an Optimized Anti-VEGF Antibody: Crystal Structure of an Affinity-matured Fab in Complex with Antigen," *J Mol Biol.* 5:293(4):865-81(1999).
Coleman, PM., "Effects of amino acid sequence changes on antibody-antigen interactions" *Res. Immunology.* 145:33-36 (1994).
De Jong et al., "Regulation of expression of CD27, a T cell-specific member of a novel family of membrane receptors," *J. Immunol.* 146(8):2488-2494 (1991).
De Pascalis et al., "Grafting of "Abbreviated" Complementarity-Determining Regions Containing Specificity-Determining Residues Essential of Ligand Contact to Engineer a Less Immunogenic Humanized Monoclonal Antibody" *J. Immunol.* 15/169(6):3076-84 (2002).
Den Haan et al., "Identification of a graft versus host disease-associated human minor histocompatibility antigen," *Science.* 268(5216):1476-1480 (1995).
Dillman, R. O., "Monoclonal Antibodies for Treating Cancer" *Ann. Int. Med.* 111:592-603 (1989).
Doronina et al., "Development of potent monoclonal antibody auristatin conjugates for cancer therapy," *Nature Biotechnology.*, 21(7):778-784 (2003) + erratum: 21(8):941(2003).
Emery, et al., "Humanised monoclonal antibodies for therapeutic applications" *Exp. Opin. Invest. Drugs.* 3(3):241-251.
EP 04 71 3441 Supplementary Partial European Search Report completed Mar. 12, 2007.
Giralt et al., "Leukemia relapse after allogeneic bone marrow transplantation: a review " *Blood.* 84(11):3603-3612.
Goodwin et al., "Molecular and biological characterization of a ligand for CD27 defines a new family of cytokines with homology to tumor necrosis factor," *Cell.* 73(3):447-456 (1993).
Gordon et al., "Humanized Anti-CD70 Auristatin Antibody-Drug Conjugates Show Potent In Vitro Cytotoxicity in Renal Cell Carcinoma Primary Cultures Established from Patient Tumor Isolates," Abstract No. 3733, 97th Annual Meeting of the American Association for Cancer Research, Apr. 1-5, 2006, Washington, D.C.
Gravestein et al., "Cloning and expression of murine CD27: comparison with 4-1 BB, another lymphocyte-specific member of the nerve growth factor receptor family," *Eur. J. Immunol.* 23(4):943-950 (1993).
Gravestein et al., "Novel mAbs reveal potent co-stimulatory activity of murine CD27," *Int. Immunol.* 7(4):551-557.
Gruss et al., "Pathophysiology of Hodgkin's disease: functional and molecular aspects," *Baillieres Clin. Haematol.* 9(3):417-446 (1996).
Held-Feindt et al., "CD70/CD27 ligand, a member of the TNF family, is expressed in human brain tumors," *Int. J. Cancer.* 98(3):352-356 (2002).
Hintzen et al., "A soluble form of the human T cell differentiation antigen CD27 is released after triggering of the TCR/CD3 complex," *J. Immunol.* 147(1):29-35 (1991).
Hintzen et al., "CD27: marker and mediator of T-cell activation?," *Immunol. Today.* 15(7):307-311 (1994).
Hintzen et al., "CD70 represents the human ligand for CD 27," *Int. Immunol.* 6(3):477-480 (1994).
Hintzen et al., "Characterization of the human CD27 ligand, a novel member of the TNF gene family," *J. Immunol.* 152(4):1762-1773 (1994).
Hintzen et al., "Engagement of CD27 with its ligand CD70 provides a second signal for T cell activation," *J. Immunol.* 154(6):2612-2623 (1995).
Hintzen et al., "Regulation of CD27 expression on subsets of mature T-lymphocytes," *J. Immunol.* 151(5):2426-2435.
Hishima et al., "CD70 expression in thymic carcinoma," *Am. J. Surg. Pathol.* 24(5):742-746 (2000).
Holm et al., "Functional mapping and single chain construction of the anti-cytokeratin 8 monoclonal antibody TS1" *Mol. Immunol.* 44:1075-84 (2007). Epub 2006.
International Search Report mailed Jun. 2, 2006 in International Application No. PCT/US05/36994.
Jacquot et al., "CD154/CD40 and CD70/CD27 interactions have different and sequential functions in T cell-dependent B cell responses: enhancement of plasma cell differentiation by CD27 signaling," *J. Immunol.* 159(6):2652-2657 (1997).
Jeffrey et al., "Development and properties of beta-glucuronide linkers for monoclonal antibody-drug conjugates," Bioconjug. *Chem.* 17(3):831-840 (2006).
Knoll et al., "Targeted Therapy of Experimental Renal Cell Carcinoma with a Novel Conjugate of Monoclonal Antibody 138H11 and Calicheamicin ØII," *Cancer Research*. 60:6089-6094 (2000).
Kobata et al., "CD27-CD70 interactions regulate B-cell activation by T cells," *PNAS.* 92(24):11249-11253 (1995).
Law et al., "Anti-CD70 Antibody Drug Conjugates Mediate Renal Carcinoma Cell Killing Through Cytotoxic Drug Delivery and Antibody-Dependent Cellular Cytotoxicity (abstract only)", *Proc Amer Assoc Cancer Res.* 46:6143 (2005).
Law et al., "Anti-CD70 Auristatin Conjugates with Potent and Selective Activity Against Renal Cell Carcinoma," poster presentation, 4th International Kidney Cancer Symposium, Oct. 21-23, 2005, Chicago, IL.
Law et al., "Lymphocyte Activation Antigen CD70 Expressed by Renal Cell Carcinoma Is a Potential Therapeutic Target for Anti-CD70 Antibody-Drug Conjugates," *Cancer Res.* 2006; 66:(4) 2328-2337.
Lens et al., "Aberrant expression and reverse signaling of CD70 on malignant B cells," *Br. J. Haematol.* 106(2):491-503 (1999).
Lens et al., "Antigen-presenting cell-derived signals determine expression levels of CD70 on primed T cells," *Immunol.* 90:38-45 (1997).
Lens et al., "Control of lymphocyte function through CD27-CD70 interactions," *Semin Immunol.* 10(6):491-499 (1998).
Lens et al., "Phenotype and function of human B cells expressing CD70 (CD27 ligand)," *Eur. J. Immunol.* 26(12):2964-2971 (1996).
Locksley et al., "The TNF and TNF receptor superfamilies: integrating mammalian biology," *Cell.* 104(4):487-501 (2001).
MacCallum, et al "Antibody-antigen Interactions: Contact Analysis and Binding Site Topography" *J Mol. Biol.* 262:732-745 (1996).
Maurer et al., "CD27 expression by a distinct subpopulation of human B lymphocytes," *Eur. J. Immunol.* 20(12):2679-2684 (1990).
McEarchern et al., "Engineered Anti-CD70 Antibody Variants Support Multiple Effector Functions and Exhibit Potent In Vitro and In Vivo Antitumor Activities (abstract only)" *Proc Amer Assoc Cancer Res.* 46:6142 (2005).
McEarchern et al., "A Humanized Anti-CD70 Monoclonal Antibody Targets CD70-Expressing Multiple Myeloma," Publication No. 1591, 47th Annual Meeting and Exposition of the American Society of Hematology, Dec. 10-13, 2005, Atlanta, Georgia.
McEarchern et al., "Engineered Anti-CD70 Antibody with Multiple Effector Functions Exhibits in vitro and in vivo Antitumor Activities", *Blood.* 2007; 109(3) 1185-1192.

McEarchern, Julie, "Antitumor Activities of Engineered Anti-CD70 Antibody (h1F6)", *Presentation by Seattle Genetics at Annual Meeting of American Association for Cancer Research* Apr. 16-20:1-15 (2005).

Nakajima et al., "Involvement of CD70-CD27 interactions in the induction of experimental autoimmune encephalomyelitis," *J. Neuroimmunol.* 109(2):188-196 (2000).

Nakajima et al., "Roles of IL-4 and IL-12 in the development of lupus in NZB/W F1 mice " *J. Immunol.* 158(3):1466-1472 (1997).

Oelke et al., "Overexpression of CD70 and Overstimulation of IgG Synthesis by Lupus T Cells and T Cells Treated With DNA Methylation Inhibitors," *Arthritis & Rheumatism.* 50(6):1850-1860 (2004).

Oflazoglu et al."In Vivo Characterization of the Mechanism of Action of c1F6, an Anti-CD70 Antibody," Abstract No. 3732, 97th Annual Meeting of the American Association for Cancer Research, Apr. 1-5, 2006, Washington, D.C.

Orengo et al., "Reciprocal expression of CD70 and of its receptor, CD27, in human long term-activated T and natural killer (NK) cells: inverse regulation by cytokines and role in induction of cytotoxicity," *Clin. Exp. Immunol.* 107(3):608-613.

Oshima et al., "Characterization of murine CD70 by molecular cloning and mAb," *Int. Immunol.* 10(4):517-526 (1998).

Paul, Willliam, "Fundamental Immunology", 3rd edition, *Laboratory of Immunology National Institute of Allergy and Infectious Diseases.* 292-295 (1993).

PCT Search Report and Written Opinion of Jun. 2, 2006 for application PCT/US05/36994 (WO 2006/044643 A3).

PCT Search Report and Written Opinion of Oct. 16, 2007 for application PCT/US06/015145 (WO 2006/113909 A3).

PCT Search Report of Oct. 4, 2007 for application PCT/US2006/037753 (WO 2007/038637 A3).

PCT Search Report of Dec. 4, 2008 for application PCT/US2007/087401 (WO 2008/074004 A3).

PCT Search Report of Dec. 22, 2004 for application PCT/US04/05247 (WO 2004/073656 A3).

PCT Search Report of Dec. 22, 2004 for application PCT/US04/05247 (WO 2004/073656 A3) (Corrected Version).

Peitsch et al., "Comparative molecular modeling of the Fas-ligand and other members of the TNF family," *Mol. Immunol.* 32(10):761-772 (1995).

Reff, M. et al., "Future of Monoclonal Antibodies in the Treatment of Hematologic Malignancies," *Cancer Control.* 9(2):152-166 (2002).

Rudikoff et al.,"Single amino acid substitution altering antigen-abinding specificity" *PNAS.* 79(6):1979-1983, Mar. 1982.

Smith et al., "A receptor for tumor necrosis factor defines an unusual family of cellular and viral proteins," *Science.* 248(4958):1019-1023 (1990).

Stein et al., "A5 Cluster Report: CDw70," pp. 446-449 from Leucocyte Typing IV White Cell Differentiation Antigens, Knapp, eds., *Oxford University Press*, 1989.

Sugita et al., "Participation of the CD27 antigen in the regulation of IL-2-activated human natural killer cells," *J. Immunol.* 149(4):1199-1203 (1992).

Tesselaar et al., "Characterization of murine CD70, the ligand of the TNF receptor family member CD27," *J. Immunol.* 159(10):4959-4965 (1997).

U.S. Appl. No. 10/546,304 Amendment filed Nov. 21, 2008 in response to Final Office Action mailed May 22, 2008.

U.S. Appl. No. 10/546,304 Final Office Action mailed May 22, 2008.

U.S. Appl. No. 10/983,340 Amendment filed Jul. 9, 2007 in response to Office Action mailed Mar. 9, 2007.

U.S. Appl. No. 10/983,340 Office Action mailed Oct. 4, 2007.

Vajdos et al. "Comprehensive Functional Maps of the Antigen-binding Site of an Anti-ErbB2 Antibody Obtained with Shotgun Scanning Mutagenesis" *J. Mol. Biol.* 5;320(2):415-28 (2002).

Van Lier et al., "Tissue distribution and biochemical and functional properties of Tp55 (CD27), a novel T cell differentiation antigen," *J. Immunol.* 139(5):1589-1596 (1987).

Wischhusen et al., "Identification of CD70-mediated apoptosis of immune effector cells as a novel immune escape pathway of human gliblastoma," *Cancer Res.* 6299):2592-2599 (2002).

Witzig et al., "Radioimmunotherapy for patients with relapsed B-cell non-Hodgkin lymphoma," *Cancer Chemother. Pharmacol.* 48(suppl. 1):S91-S95 (2001).

Written Opinion of the International Searching Authority mailed Jun. 2, 2006 for application PCT/US05/36994.

Wu et al., "Humanization of a Murine Monoclonal Antibody by Simultaneous Optimization of Framework and CDR Residues," *J Mol Biol.* 19:294(1):151-62 (1999).

U.S. Appl. No. 60/449,055, filed Feb. 20, 2003, Law et al.

Drachman, et al., "SGN-70: Phase 1a Study of a Novel Humanized Antibody Targeting CD70 for the Treatment of Autoimmune Diseases." American College of Rheumatology, Abstract No. 1273, Atlanta, Georgia, Nov. 6-11, 2010 (poster).

Grewal. "CD70 as a therapeutic target in human malignancies", *Expert Opin. Ther. Targets.* (2008) 12(3):341-351.

McEarchern et al., "Preclinical characterization of SGN-70, a humanized antibody directed against CD70", *Clin. Cancer Res.*, 14(23):7763-7772 (2008).

McEarchern et al., "SGN-70, A Humanized Anti-CD70 Antibody, Target CD70-Expressing Hematologic Tumors", ASH, Orlando, Florida, Dec. 9-12, 2006 (poster).

Schnell et al., "Current Strategies of Antibody-Based Treatment in Hodgkin's Disease", Annals of Oncology, 13 (Supplement 1): 57-66, 2002.

EP 1 799 262, Supplemental European Search Report mailed Sep. 17, 2009.

EP 1 871 418, Supplementary European Search Report mailed Dec. 7, 2009.

Harlow and Lane, Antibodies, A Laboratory Manual, *Cold Spring Harbor Laboratory*, p. 140-243, (1988).

U.S. Appl. No. 12/265,451, Final Office Action mailed Apr. 1, 2011.

Michel et al., "Intracellular Accumulation of the Anti-CD20 Antibody 1F5 in B-Lymphoma Cells", *Clinical Cancer Research*, 8:2701-2713, (2002).

Figure 1

1F6 VL nucleotide sequence:
```
1    atggagacag acacactcct gttatgggta ctgctgctct gggttccagg ttccactggt  60
61   gacattgtgc tgacacagtc tcctgcttcc ttagctgtat ctctggggca gagggccacc 120
121  atctcatgca gggccagcaa aagtgtcagt acatctggct atagttttat gcactggtat 180
181  caacagaaac caggacagcc acccaaactc ctcatctatc ttgcatccaa cctagaatct 240
241  ggggtccctg ccaggttcag tggcagtggg tctgggacag acttcaccct caacatccat 300
301  cctgtggagg aggaggatgc tgcaacctat tactgtcagc acagtaggga ggttccgtgg 360
361  acgttcggtg gaggcaccaa gctggaaatc aaacgg                            396
```

1F6 VL amino acid sequence:
```
-20  METDTLLLWV LLLWVPGSTG                                              0
1    DIVLTQSPAS LAVSLGQRAT ISCRASKSVS TSGYSFMHWY QQKPGQPPKL LIYLASNLES  60
61   GVPARFSGSG SGTDFTLNIH PVEEEDAATY YCQHSREVPW TFGGGTKLEI KR         112
```

1F6 VH nucleotide sequence:
```
1    atggcttggg tgtggacctt gctattcctg atggcagctg cccaaagtgc caagcacag   60
61   atccagttgg tgcagtctgg acctgaggtg aagaagcctg gagagacagt caagatctcc 120
121  tgcaaggctt ctggtatac cttcacaaac tatggaatga actgggtgaa gcaggctcca 180
181  ggaaagggtt taaagtggat gggctggata aacacctaca ctggagagcc aacatatgct 240
241  gatgccttca agggacggtt tgccttctct ttggaaacct ctgccagcac tgcctatttg 300
301  cagatcaaca accctcaaaaa tgaggacacg gctacatatt tctgtgcaag agactacggc 360
361  gactatggta tggactactg gggtcaagga acctcagtca ccgtctcctc a           411
```

1F6 VH amino acid sequence:
```
-19  MAWVWTLLFL MAAAQSAGA                                               0
1    QIQLVQSGPE VKKPGETVKI SCKASGYTFT NYGMNWVKQA PGKGLKWMGW INTYTGEPTY  60
61   ADAFKGRFAF SLETSASTAY LQINNLKNED TATYFCARDY GDYGMDYWGQ GTSVTVSS   118
```

Figure 2

2F2 VL nucleotide sequence:
```
  1 atggagacag acacactcct gttatgggta ctgctgctct gggttccagg ttccactggt  60
 61 gacattgtgc tgacacagtc tcctgcttcc ttaactgtat ctctggggca gaagaccacc 120
121 atctcatgca gggccagcaa gagtgtcagt acatctggct atagttttat gcactggtac 180
181 caactgaaac caggacagtc acccaaactc ctcatctatc ttgcgtccaa cctaccatct 240
241 ggggtccctg ccaggttcag tggcagtggg tctgggacag acttcaccct caaaatccat 300
301 cctgtggagg aggaggatgc tgcaacctat tactgtcagc acagtaggga gattccgtac 360
361 acgttcggag gggggaccaa gctggaaata acacgg                            396
```

2F2 VL amino acid sequence:
```
-20 METDTLLLWV LLLWVPGSTG                                              0
  1 DIVLTQSPAS LTVSLGQKTT ISCRASKSVS TSGYSFMHWY QLKPGQSPKL LIYLASNLPS 60
 61 GVPARFSGSG SGTDFTLKIH PVEEEDAATY YCQHSREIPY TFGGGTKLEI TR         112
```

2F2 VH nucleotide sequence:
```
  1 atggaatgga ctgggtctt tctcttcctc ctgtcagtaa ctgcagatgt ccaatcccag  60
 61 gttcagctgc aacagtctgg aactgagctg atgacgcctg ggcctcagt gacgatgtcc 120
121 tgcaagactt ctggctacac attcagtacc tactggatag agtgggtaaa acagaggcct 180
181 ggacatggcc ttgagtggat tggagaaatt tacctggaa gtggttatac tgactacaat 240
241 gagaagttca aggccaaggc cacattcact gcagatacat cctccaacac agcctacatg 300
301 caactcagca gcctggcatc tgaggactct gccgtctatt actgtgcaag atgggatagg 360
361 ctctatgcta tggactactg gggtcaagga acctcagtca ccgtctcctc a           411
```

2F2 VH amino acid sequence:
```
-19 MEWTWVFLFL LSVTADVQS                                               0
  1 QVQLQQSGTE LMTPGASVTM SCKTSGYTFS TYWIEWVKQR PGHGLEWIGE ILGPSGYTDY 60
 61 NEKFKAKATF TADTSSNTAY MQLSSLASED SAVYYCARWD RLYAMDYWGG GTSVTVSS   118
```

Figure 3

```
1F6 CDR-L1 (residues 23 to 38):  R A S K S V S T S G Y S F M H
2F2 CDR-L1 (residues 23 to 38):  R A S K S V S T S G Y S F M H 1F6 CDR-L2 (residues 54 to 60):  L A S N L E S
2F2 CDR-L2 (residues 54 to 60):  L A S N L P S 1F6 CDR-L3 (residues 93 to 101): Q H S R E V P W T
2F2 CDR-L3 (residues 93 to 101): Q H S R E I P Y T 1F6 CDR-H1 (residues 26 to 35):  G Y T F T N Y G M N
2F2 CDR-H1 (residues 26 to 35):  G Y T F S T Y W I E 1F6 CDR-H2 (residues 49 to 66):  W I N T Y T G E P T Y A D D A F K G
2F2 CDR-H2 (residues 49 to 66):  E I L G P S G Y T D Y N E K F K A 1F6 CDR-H3 (residues 99 to 107): D Y G D Y G M D Y
2F2 CDR-H3 (residues 99 to 107): W D R L Y A M D Y
```

Figure 15

| Cell Line | % specific ADCP activity |
|---|---|
| Renal Cell Carcinoma | |
| 786-O | 62 |
| A498 | 55 |
| Hodgkin's Disease | |
| KMH2 | 8 |
| L428 | 25 |
| Hs445 | 38 |
| RPMI-6666 | 49 |
| Multiple Myeloma | |
| LP-1 | 30 |
| Non-Hodgkin's Lymphoma | |
| MHH-PreB-1 | 45 |
| B cell lymphoma | |
| WIL2-S | 39 |

Figure 16
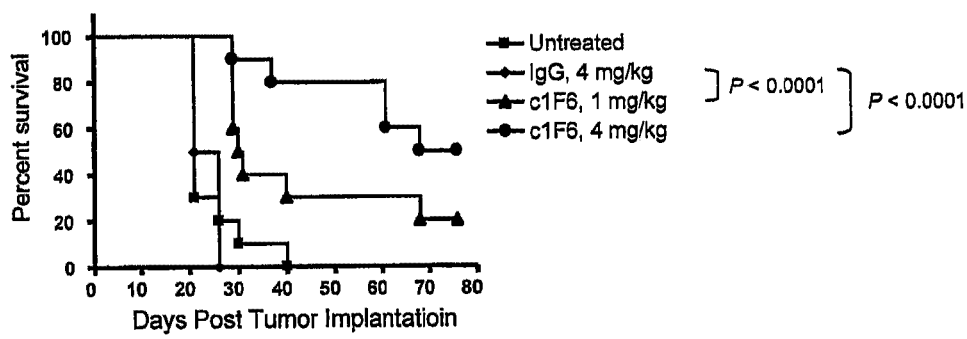
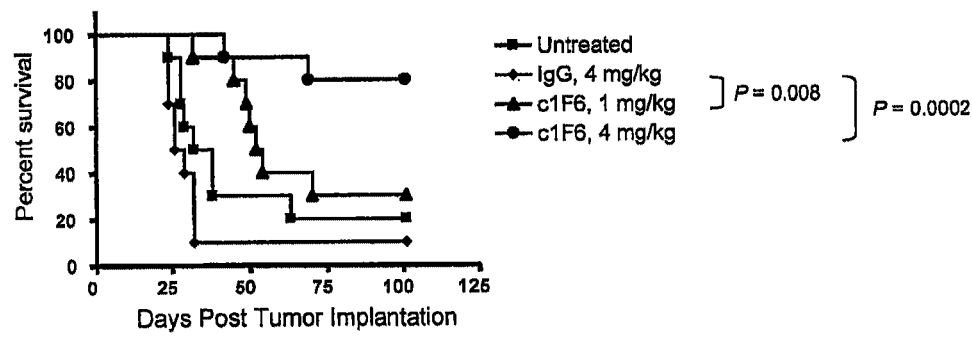

ns, and 50% of B-CLL have been reported to express CD70 (Lens et al., 1999, *Br. J. Haematol.* 106:491-503). CD70 is frequently expressed together with other lymphoid activation markers on the malignant Hodgkin and Reed-Sternberg cells of Hodgkin's disease (Gruss and Kadin, 1996, *Bailieres Clin. Haematol.* 9:417-46). One report demonstrates CD70 expression on 88% (7 of 8 cases) of thymic carcinomas and 20% (1 of 5 cases) of atypical thymomas (Hishima et al., 2000, supra). The second type of carcinoma on which CD70 has been detected is nasopharyngeal carcinoma. One study reports the presence of CD70 on 80% (16 of 20 cases) of snap-frozen tumor biopsies obtained from undifferentiated nasopharyngeal carcinomas (Agathanggelou et al, 1995, *Am J Path* 147:1152-60). CD70 has also been detected on brain tumor cells, especially glioma cell lines, solid human gliomas, and meningiomas (Held-Feindt and Mentlein, 2002, *Int. J. Cancer* 98:352-56; Wischlusen et al., 2002, *Can. Res.* 62:2592-99).

SEQUENCE LISTING

<160> NUMBER OF SEQ ID NOS: 50

<210> SEQ ID NO 1
<211> LENGTH: 411
<212> TYPE: DNA
<213> ORGANISM: Artificial
<220> FEATURE:
<223> OTHER INFORMATION: 1F6 Heavy Chain Variable region

<400> SEQUENCE: 1

```
atggcttggg tgtggacctt gctattcctg atggcagctg cccaaagtgc ccaagcacag      60
atccagttgg tgcagtctgg acctgaggtg aagaagcctg agagacagt caagatctcc     120 tgcaaggctt ctgggtatac cttcacaaac tatggaatga actgggtgaa gcaggctcca    180
ggaaagggtt taaagtggat gggctggata acacctaca ctggagagcc aacatatgct     240
gatgccttca agggacggtt tgccttctct ttggaaacct ctgccagcac tgcctatttg    300
cagatcaaca acctcaaaaa tgaggacacg gctacatatt tctgtgcaag agactacggc    360
gactatggta tggactactg gggtcaagga acctcagtca ccgtctcctc a             411
```

<210> SEQ ID NO 2
<211> LENGTH: 137
<212> TYPE: PRT
<213> ORGANISM: Artificial
<220> FEATURE:
<223> OTHER INFORMATION: 1F6 Heavy Chain Variable region

<400> SEQUENCE: 2

```
Met Ala Trp Val Trp Thr Leu Leu Phe Leu Met Ala Ala Gln Ser
1               5                   10                  15

Ala Gly Ala Gln Ile Gln Leu Val Gln Ser Gly Pro Glu Val Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Ala Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Asp Tyr Gly Asp Tyr Gly Met Asp Tyr Trp Gly
        115                 120                 125

Gln Gly Thr Ser Val Thr Val Ser Ser
    130                 135
```

<210> SEQ ID NO 3
<211> LENGTH: 57
<212> TYPE: DNA
<213> ORGANISM: Artificial
<220> FEATURE:
<223> OTHER INFORMATION: 1F6 Heavy Chain Signal Peptide

<400> SEQUENCE: 3

```
atggcttggg tgtggacctt gctattcctg atggcagctg cccaaagtgc ccaagca        57
```

```
<210> SEQ ID NO 4
<211> LENGTH: 19
<212> TYPE: PRT
<213> ORGANISM: Artificial
<220> FEATURE:
<223> OTHER INFORMATION: 1F6 Heavy Chain Signal Peptide

<400> SEQUENCE: 4

Met Ala Trp Val Trp Thr Leu Leu Phe Leu Met Ala Ala Ala Gln Ser
1               5                   10                  15

Ala Gly Ala

<210> SEQ ID NO 5
<211> LENGTH: 30
<212> TYPE: DNA
<213> ORGANISM: Artificial
<220> FEATURE:
<223> OTHER INFORMATION: 1F6 Heavy Chain -CDR1(H1)

<400> SEQUENCE: 5
gggtatacct tcacaaacta tggaatgaac                                    30

<210> SEQ ID NO 6
<211> LENGTH: 30
<212> TYPE: PRT
<213> ORGANISM: Artificial
<220> FEATURE:
<223> OTHER INFORMATION: 1F6 Heavy Chain -CDR1(H1)

<400> SEQUENCE: 6

Gly Leu Tyr Thr Tyr Arg Thr His Arg Pro His Glu Thr His Arg Ala
1               5                   10                  15

Ser Asn Thr Tyr Arg Gly Leu Tyr Met Glu Thr Ala Ser Asn
            20                  25                  30

<210> SEQ ID NO 7
<211> LENGTH: 51
<212> TYPE: DNA
<213> ORGANISM: Artificial
<220> FEATURE:
<223> OTHER INFORMATION: 1F6 Heavy Chain -CDR2(H2)

<400> SEQUENCE: 7
tggataaaca cctacactgg agagccaaca tatgctgatg ccttcaaggg a            51

<210> SEQ ID NO 8
<211> LENGTH: 17
<212> TYPE: PRT
<213> ORGANISM: Artificial
<220> FEATURE:
<223> OTHER INFORMATION: 1F6 Heavy Chain -CDR2(H2)

<400> SEQUENCE: 8

Trp Ile Asn Thr Tyr Thr Gly Glu Pro Thr Tyr Ala Asp Ala Phe Lys
1               5                   10                  15

Gly

<210> SEQ ID NO 9
<211> LENGTH: 27
<212> TYPE: DNA
<213> ORGANISM: Artificial
<220> FEATURE:
<223> OTHER INFORMATION: 1F6 Heavy Chain -CDR3(H3)

<400> SEQUENCE: 9
gactacggcg actatggtat ggactac                                       27
```

```
<210> SEQ ID NO 10
<211> LENGTH: 9
<212> TYPE: PRT
<213> ORGANISM: Artificial
<220> FEATURE:
<223> OTHER INFORMATION: 1F6 Heavy Chain -CDR3(H3)

<400> SEQUENCE: 10

Asp Tyr Gly Asp Tyr Gly Met Asp Tyr
1               5

<210> SEQ ID NO 11
<211> LENGTH: 396
<212> TYPE: DNA
<213> ORGANISM: Artificial
<220> FEATURE:
<223> OTHER INFORMATION: 1F6 Light Chain Variable Region

<400> SEQUENCE: 11
atggagacag acacactcct gttatgggta ctgctgctct ggttccagg ttccactggt      60 gacattgtgc tgacacagtc tcctgcttcc ttagctgtat ctctggggca gagggccacc    120
atctcatgca gggccagcaa aagtgtcagt acatctggct atagttttat gcactggtat    180
caacagaaac aggacagcc acccaaactc ctcatctatc ttgcatccaa cctagaatct     240
ggggtccctg ccaggttcag tggcagtggg tctgggacag acttcaccct caacatccat    300
cctgtggagg aggaggatgc tgcaacctat tactgtcagc acagtaggga ggttccgtgg    360
acgttcggtg aggcaccaa gctggaaatc aaacgg                               396

<210> SEQ ID NO 12
<211> LENGTH: 132
<212> TYPE: PRT
<213> ORGANISM: Artificial
<220> FEATURE:
<223> OTHER INFORMATION: 1F6 Light Chain Variable Region

<400> SEQUENCE: 12

Met Glu Thr Asp Thr Leu Leu Leu Trp Val Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Lys Ser
        35                  40                  45

Val Ser Thr Ser Gly Tyr Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln His Ser Arg Glu Val Pro Trp Thr Phe Gly Gly Gly Thr Lys Leu
        115                 120                 125

Glu Ile Lys Arg
    130

<210> SEQ ID NO 13
<211> LENGTH: 60
<212> TYPE: DNA
<213> ORGANISM: Artificial
<220> FEATURE:
<223> OTHER INFORMATION: 1F6 Light Chain Signal Peptide
```

<400> SEQUENCE: 13
atggagacag acacactcct gttatgggta ctgctgctct gggttccagg ttccactggt        60

<210> SEQ ID NO 14
<211> LENGTH: 20
<212> TYPE: PRT
<213> ORGANISM: Artificial
<220> FEATURE:
<223> OTHER INFORMATION: 1F6 Light Chain Signal Peptide

<400> SEQUENCE: 14

Met Glu Thr Asp Thr Leu Leu Leu Trp Val Leu Leu Leu Trp Val Pro
1               5                   10                  15

Gly Ser Thr Gly
            20

<210> SEQ ID NO 15
<211> LENGTH: 45
<212> TYPE: DNA
<213> ORGANISM: Artificial
<220> FEATURE:
<223> OTHER INFORMATION: 1F6 Light Chain-CDR1 (L1)

<400> SEQUENCE: 15
agggccagca aaagtgtcag tacatctggc tatagtttta tgcac                        45

<210> SEQ ID NO 16
<211> LENGTH: 15
<212> TYPE: PRT
<213> ORGANISM: Artificial
<220> FEATURE:
<223> OTHER INFORMATION: 1F6 Light Chain-CDR1 (L1)

<400> SEQUENCE: 16

Arg Ala Ser Lys Ser Val Ser Thr Ser Gly Tyr Ser Phe Met His
1               5                   10                  15

<210> SEQ ID NO 17
<211> LENGTH: 21
<212> TYPE: DNA
<213> ORGANISM: Artificial
<220> FEATURE:
<223> OTHER INFORMATION: 1F6 Light Chain-CDR2 (L2)

<400> SEQUENCE: 17
cttgcatcca acctagaatc t                                                  21

<210> SEQ ID NO 18
<211> LENGTH: 7
<212> TYPE: PRT
<213> ORGANISM: Artificial
<220> FEATURE:
<223> OTHER INFORMATION: 1F6 Light Chain-CDR2 (L2)

<400> SEQUENCE: 18

Leu Ala Ser Asn Leu Glu Ser
1               5

<210> SEQ ID NO 19
<211> LENGTH: 27
<212> TYPE: DNA
<213> ORGANISM: Artificial
<220> FEATURE:
<223> OTHER INFORMATION: 1F6 Light Chain-CDR3 (L3)

<400> SEQUENCE: 19
cagcacagta gggaggttcc gtggacg                                          27

<210> SEQ ID NO 20
<211> LENGTH: 9
<212> TYPE: PRT
<213> ORGANISM: Artificial
<220> FEATURE:
<223> OTHER INFORMATION: 1F6 Light Chain-CDR3 (L3)

<400> SEQUENCE: 20

Gln His Ser Arg Glu Val Pro Trp Thr
1               5

<210> SEQ ID NO 21
<211> LENGTH: 411
<212> TYPE: DNA
<213> ORGANISM: Artificial
<220> FEATURE:
<223> OTHER INFORMATION: 2F2 Heavy Chain Variable Region

<400> SEQUENCE: 21
atggaatgga cctgggtctt tctcttcctc ctgccagtaa ctgcagatgt ccaatcccag      60
gttcagctgc aacagtctgg aactgagctg atgacgcctg gggcctcagt gacgatgtcc    120
tgcaagactt ctggctacac attcagtacc tactggatag agtgggtaaa acagaggcct    180
ggacatggcc ttgagtggat tggagaaatt ttacctggaa gtggttatac tgactacaat    240
gagaagttca aggccaaggc cacattcact gcagatacat cctccaacac agcctacatg    300
caactcagca gcctggcatc tgaggactct gccgtctatt actgtgcaag atgggatagg    360
ctctatgcta tggactactg gggtcaagga acctcagtca ccgtctcctc a              411

<210> SEQ ID NO 22
<211> LENGTH: 137
<212> TYPE: PRT
<213> ORGANISM: Artificial
<220> FEATURE:
<223> OTHER INFORMATION: 2F2 Heavy Chain Variable Region

<400> SEQUENCE: 22

Met Glu Trp Thr Trp Val Phe Leu Phe Leu Leu Ser Val Thr Ala Asp
1               5                   10                  15

Val Gln Ser Gln Val Gln Leu Gln Gln Ser Gly Thr Glu Leu Met Thr
            20                  25                  30

Pro Gly Ala Ser Val Thr Met Ser Cys Lys Thr Ser Gly Tyr Thr Phe
        35                  40                  45

Ser Thr Tyr Trp Ile Glu Trp Val Lys Gln Arg Pro Gly His Gly Leu
    50                  55                  60

Glu Trp Ile Gly Glu Ile Leu Gly Pro Ser Gly Tyr Thr Asp Tyr Asn
65                  70                  75                  80

Glu Lys Phe Lys Ala Lys Ala Thr Phe Thr Ala Asp Thr Ser Ser Asn
                85                  90                  95

Thr Ala Tyr Met Gln Leu Ser Ser Leu Ala Ser Glu Asp Ser Ala Val
            100                 105                 110

Tyr Tyr Cys Ala Arg Trp Asp Arg Leu Tyr Ala Met Asp Tyr Trp Gly
        115                 120                 125

Gly Gly Thr Ser Val Thr Val Ser Ser
    130                 135

```
<210> SEQ ID NO 23
<211> LENGTH: 57
<212> TYPE: DNA
<213> ORGANISM: Artificial
<220> FEATURE:
<223> OTHER INFORMATION: 2F2 Heavy Chain Signal Peptide

<400> SEQUENCE: 23
atggaatgga cctgggtctt tctcttcctc ctgtcagtaa ctgcagatgt ccaatcc        57

<210> SEQ ID NO 24
<211> LENGTH: 19
<212> TYPE: PRT
<213> ORGANISM: Artificial
<220> FEATURE:
<223> OTHER INFORMATION: 2F2 Heavy Chain Signal Peptide

<400> SEQUENCE: 24

Met Glu Trp Thr Trp Val Phe Leu Phe Leu Leu Ser Val Thr Ala Asp
1               5                   10                  15

Val Gln Ser

<210> SEQ ID NO 25
<211> LENGTH: 30
<212> TYPE: DNA
<213> ORGANISM: Artificial
<220> FEATURE:
<223> OTHER INFORMATION: 2F2 Heavy Chain -CDR1 (H1)

<400> SEQUENCE: 25
ggctacacat tcagtaccta ctggatagag                                     30

<210> SEQ ID NO 26
<211> LENGTH: 10
<212> TYPE: PRT
<213> ORGANISM: Artificial
<220> FEATURE:
<223> OTHER INFORMATION: 2F2 Heavy Chain -CDR1 (H1)

<400> SEQUENCE: 26

Gly Tyr Thr Phe Ser Thr Tyr Trp Ile Glu
1               5                   10

<210> SEQ ID NO 27
<211> LENGTH: 51
<212> TYPE: DNA
<213> ORGANISM: Artificial
<220> FEATURE:
<223> OTHER INFORMATION: 2F2 Heavy Chain -CDR2 (H2)

<400> SEQUENCE: 27
gaaattttac ctggaagtgg ttatactgac tacaatgaga agttcaaggc c              51

<210> SEQ ID NO 28
<211> LENGTH: 17
<212> TYPE: PRT
<213> ORGANISM: Artificial
<220> FEATURE:
<223> OTHER INFORMATION: 2F2 Heavy Chain -CDR2 (H2)

<400> SEQUENCE: 28

Glu Ile Leu Pro Gly Ser Gly Tyr Thr Asp Tyr Asn Glu Lys Phe Lys
1               5                   10                  15

Ala
```

<210> SEQ ID NO 29
<211> LENGTH: 27
<212> TYPE: DNA
<213> ORGANISM: Artificial
<220> FEATURE:
<223> OTHER INFORMATION: 2F2 Heavy Chain -CDR3 (H3)

<400> SEQUENCE: 29
tgggataggc tctatgctat ggactac                                    27

<210> SEQ ID NO 30
<211> LENGTH: 9
<212> TYPE: PRT
<213> ORGANISM: Artificial
<220> FEATURE:
<223> OTHER INFORMATION: 2F2 Heavy Chain -CDR3 (H3)

<400> SEQUENCE: 30

Trp Asp Arg Leu Tyr Ala Met Asp Tyr
1               5

<210> SEQ ID NO 31
<211> LENGTH: 396
<212> TYPE: DNA
<213> ORGANISM: Artificial
<220> FEATURE:
<223> OTHER INFORMATION: 2F2 Light Chain Variable Region

<400> SEQUENCE: 31
atggagacag acacactcct gttatgggta ctgctgctct ggttccagg ttccactggt      60
gacattgtgc tgacacagtc tcctgcttcc ttaactgtat ctctggggca aagaccacc    120
atctcatgca gggccagcaa gagtgtcagt acatctggct atagttttat gcactggtac   180
caactgaaac aggacagtc acccaaactc ctcatctatc ttgcgtccaa cctaccatct    240
ggggtccctg ccaggttcag tggcagtggg tctgggacag acttcaccct caaaatccat   300
cctgtggagg aggaggatgc tgcaacctat tactgtcagc acagtaggga gattccgtac   360
acgttcggag gggggaccaa gctggaaata acacgg                             396

<210> SEQ ID NO 32
<211> LENGTH: 132
<212> TYPE: PRT
<213> ORGANISM: Artificial
<220> FEATURE:
<223> OTHER INFORMATION: 2F2 Light Chain Variable Region

<400> SEQUENCE: 32

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Thr
            20                  25                  30

Val Ser Leu Gly Gln Lys Thr Thr Ile Ser Cys Arg Ala Ser Lys Ser
        35                  40                  45

Val Ser Thr Ser Gly Tyr Ser Phe Met His Trp Tyr Gln Leu Lys Pro
    50                  55                  60

Gly Gln Ser Pro Lys Leu Leu Ile Tyr Leu Ala Ser Asn Leu Pro Ser
65                  70                  75                  80

Gly Val Pro Ala Arg Phe Ser Gly Ser Gly Ser Gly Thr Asp Phe Thr
                85                  90                  95

Leu Lys Ile His Pro Val Glu Glu Glu Asp Ala Ala Thr Tyr Tyr Cys
            100                 105                 110

Gln His Ser Arg Glu Ile Pro Tyr Thr Phe Gly Gly Gly Thr Lys Leu
    115                 120                 125

Glu Ile Thr Arg
    130

<210> SEQ ID NO 33
<211> LENGTH: 60
<212> TYPE: DNA
<213> ORGANISM: Artificial
<220> FEATURE:
<223> OTHER INFORMATION: 2F2 Light Chain Signal Peptide

<400> SEQUENCE: 33
atggagacag acacactcct gttatgggta ctgctgctct gggttccagg ttccactggt    60

<210> SEQ ID NO 34
<211> LENGTH: 20
<212> TYPE: PRT
<213> ORGANISM: Artificial
<220> FEATURE:
<223> OTHER INFORMATION: 2F2 Light Chain Signal Peptide

<400> SEQUENCE: 34

Met Glu Thr Asp Thr Leu Leu Leu Trp Val Leu Leu Leu Trp Val Pro
1               5                   10                  15

Gly Ser Thr Gly
            20

<210> SEQ ID NO 35
<211> LENGTH: 45
<212> TYPE: DNA
<213> ORGANISM: Artificial
<220> FEATURE:
<223> OTHER INFORMATION: 2F2 Light Chain-CDR1 (L1)

<400> SEQUENCE: 35
agggccagca agagtgtcag tacatctggc tatagtttta tgcac    45

<210> SEQ ID NO 36
<211> LENGTH: 15
<212> TYPE: PRT
<213> ORGANISM: Artificial
<220> FEATURE:
<223> OTHER INFORMATION: 2F2 Light Chain-CDR1 (L1)

<400> SEQUENCE: 36

Arg Ala Ser Lys Ser Val Ser Thr Ser Gly Tyr Ser Phe Met His
1               5                   10                  15

<210> SEQ ID NO 37
<211> LENGTH: 21
<212> TYPE: DNA
<213> ORGANISM: Artificial
<220> FEATURE:
<223> OTHER INFORMATION: 2F2 Light Chain-CDR2 (L2)

<400> SEQUENCE: 37
cttgcgtcca acctaccatc t    21

<210> SEQ ID NO 38
<211> LENGTH: 7
<212> TYPE: PRT
<213> ORGANISM: Artificial
<220> FEATURE:
<223> OTHER INFORMATION: 2F2 Light Chain-CDR2 (L2)

-continued

```
<400> SEQUENCE: 38

Leu Ala Ser Asn Leu Pro Ser
1               5

<210> SEQ ID NO 39
<211> LENGTH: 28
<212> TYPE: DNA
<213> ORGANISM: Artificial
<220> FEATURE:
<223> OTHER INFORMATION: 2F2 Light Chain-CDR3 (L3)

<400> SEQUENCE: 39
cagcacagta gggagattcc gtacacgt                                       28

<210> SEQ ID NO 40
<211> LENGTH: 9
<212> TYPE: PRT
<213> ORGANISM: Artificial
<220> FEATURE:
<223> OTHER INFORMATION: 2F2 Light Chain-CDR3 (L3)

<400> SEQUENCE: 40

Gln His Ser Arg Glu Ile Pro Tyr Thr
1               5

<210> SEQ ID NO 41
<211> LENGTH: 25
<212> TYPE: DNA
<213> ORGANISM: Artificial
<220> FEATURE:
<223> OTHER INFORMATION: mIgcK1 primer

<400> SEQUENCE: 41
cttccacttg acattgatgt ctttg                                          25

<210> SEQ ID NO 42
<211> LENGTH: 22
<212> TYPE: DNA
<213> ORGANISM: Artificial
<220> FEATURE:
<223> OTHER INFORMATION: mIgG1 primer

<400> SEQUENCE: 42
caggtcactg tcactggctc ag                                             22

<210> SEQ ID NO 43
<211> LENGTH: 37
<212> TYPE: DNA
<213> ORGANISM: Artificial
<220> FEATURE:
<223> OTHER INFORMATION: ANCTAIL primer

<400> SEQUENCE: 43
gtcgatgagc tctagaattc gtgcccccccc ccccccc                            37

<210> SEQ ID NO 44
<211> LENGTH: 47
<212> TYPE: DNA
<213> ORGANISM: Artificial
<220> FEATURE:
<223> OTHER INFORMATION: HBS-mck primer

<400> SEQUENCE: 44
cgtcatgtcg acggatccaa gcttcaagaa gcacacgact gaggcac                  47
```

```
<210> SEQ ID NO 45
<211> LENGTH: 47
<212> TYPE: DNA
<213> ORGANISM: Artificial
<220> FEATURE:
<223> OTHER INFORMATION: HBS-mG1 primer

<400> SEQUENCE: 45
cgtcatgtcg acggatccaa gcttgtcacc atggagttag tttgggc          47

<210> SEQ ID NO 46
<211> LENGTH: 42
<212> TYPE: DNA
<213> ORGANISM: Artificial
<220> FEATURE:
<223> OTHER INFORMATION: Primer

<400> SEQUENCE: 46
ataaataagc ttaccgccac catggcttgg gtgtggacct tg              42

<210> SEQ ID NO 47
<211> LENGTH: 33
<212> TYPE: DNA
<213> ORGANISM: Artificial
<220> FEATURE:
<223> OTHER INFORMATION: Reverse primer

<400> SEQUENCE: 47
ataaaggcta gctgaggaga cggtgactga ggt                         33

<210> SEQ ID NO 48
<211> LENGTH: 42
<212> TYPE: DNA
<213> ORGANISM: Artificial
<220> FEATURE:
<223> OTHER INFORMATION: Forward primer

<400> SEQUENCE: 48 ataagaagc ttaccgccac catggagaca gacacactcc tg               42

<210> SEQ ID NO 49
<211> LENGTH: 54
<212> TYPE: DNA
<213> ORGANISM: Artificial
<220> FEATURE:
<223> OTHER INFORMATION: Reverse primer

<400> SEQUENCE: 49 ataaggaag acagatggtg cagccacagt ccgtttgatt tccagcttgg tgcc   54

<210> SEQ ID NO 50
<211> LENGTH: 9
<212> TYPE: PRT
<213> ORGANISM: Artificial
<220> FEATURE:
<223> OTHER INFORMATION: M1 peptide

<400> SEQUENCE: 50

Gly Ile Leu Gly Phe Val Phe Thr Leu
1               5
```

ANTI-CD70 ANTIBODY AND ITS USE FOR THE TREATMENT AND PREVENTION OF CANCER AND IMMUNE DISORDERS

CROSS REFERENCES TO RELATED APPLICATIONS

This application is a continuation of U.S. application Ser. No. 11/735,365, filed Apr. 13, 2007, which is a continuation-in-part of U.S. application Ser. No. 11/251,173 (now U.S. Pat. No. 7,491,390), filed Oct. 14, 2005, which claims the benefit of U.S. Provisional Patent Application No. 60/619,018, filed Oct. 15, 2004, and U.S. Provisional Application No. 60/645,355, filed Jan. 19, 2005, each of which is incorporated by reference herein in its entirety. This application also claims the benefit of U.S. Provisional Patent Application No. 60/792,132, filed Apr. 13, 2006, which is incorporated by reference herein in its entirety.

REFERENCE TO A SEQUENCE LISTING

This application includes a Sequence Listing provided in ASCII text file 825SEQLIST.txt, of size 16,647 bytes and created on Feb. 6, 2009, which is hereby incorporated by reference in its entirety for all purposes.

BACKGROUND OF THE INVENTION

CD70 is a member of the tumor necrosis factor (TNF) family of cell membrane-bound and secreted molecules that are expressed by a variety of normal and malignant cell types. The primary amino acid (AA) sequence of CD70 predicts a transmembrane type II protein with its carboxyl terminus exposed to the outside of cells and its amino terminus found in the cytosolic side of the plasma membrane (Bowman et al., 1994, *J. Immunol.* 152:1756-61; Goodwin et al., 1993, *Cell* 73:447-56). Human CD70 is composed of a 20 AA cytoplasmic domain, an 18 AA transmembrane domain, and a 155 AA extracytoplasmic domain with two potential N-linked glycosylation sites (Bowman et al., supra; Goodwin et al., supra). Specific immunoprecipitation of radioisotope-labeled CD70-expressing cells by anti-CD70 antibodies yields polypeptides of 29 and 50 kDa (Goodwin et al., supra; Hintzen et al., 1994, *J. Immunol.* 152:1762-73). Based on its homology to TNF-alpha and TNF-beta, especially in structural strands C, D, H and I, a trimeric structure is predicted for CD70 (Petsch et al., 1995, *Mol. Immunol.* 32:761-72).

Original immunohistological studies revealed that CD70 is expressed on germinal center B cells and rare T cells in tonsils, skin, and gut (Hintzen et al., 1994, *Int. Immunol.* 6:477-80). Subsequently, CD70 was reported to be expressed on the cell surface of recently antigen-activated T and B lymphocytes, and its expression wanes after the removal of antigenic stimulation (Lens et al., 1996, *Eur. J. Immunol.* 26:2964-71; Lens et al., 1997, *Immunology* 90:38-45). Within the lymphoid system, activated natural killer cells (Orengo et al., 1997, *Clin. Exp. Immunol.* 107:608-13) and mouse mature peripheral dendritic cells (Akiba et al., 2000, *J. Exp. Med.* 191:375-80) also express CD70. In non-lymphoid lineages, CD70 has been detected on thymic medullar epithelial cells (Hintzen et al., 1994, supra; Hishima et al., 2000, *Am. J. Surg. Pathol.* 24:742-46).

In addition to expression on normal cells, CD70 expression has been reported in different types of cancers including lymphomas, carcinomas, and tumors of neural origin. In malignant B cells, 71% of diffuse large B-cell lymphomas, 33% of follicle center lymphomas, 25% of mantle lympho- The receptor for CD70 is CD27, a glycosylated type I transmembrane protein of about 55 kDa (Goodwin et al, 1993, *Cell* 73:447-56; Hintzen et al., 1994, supra). CD70 is sometimes referred to as CD27L. CD27, which exists as a homodimer on the cell surface (Gravestein et al, 1993, *Eur. J. Immunol.* 23:943-50), is a member of the TNF receptor superfamily as defined by cysteine-rich repeats of about 40 amino acids in the extracellular domain (Smith et al., 1990, *Science* 248:1019-23; Locksley et al., 2001, *Cell* 104:487-501). CD27 is expressed by thymocytes, NK, T, and B cells (Hintzen et al., 1994, *Immunol. Today* 15:307-11; Lens et al, 1998, *Semin. Immunol.* 10:491-99). On resting T cells, CD27 is constitutively expressed, yet antigenic triggering further upregulates CD27 expression (de Jong et al., 1991, *J. Immunol.* 146:2488-94; Hintzen et al., 1993, *J. Immunol.* 151:2426-35). Further, triggering of T cells via their T cell antigen receptor complex alone or in combination with the accessory molecule CD28 releases soluble CD27 from activated T cells (Hintzen et al., 1991, *J. Immunol.* 147:29-35). Naïve B cells do not express CD27, but its expression is induced and, in contrast to CD70, sustained after antigenic triggering of B cells (Jacquot et al., 1997, *J. Immunol.* 159:2652-57; Kobata et al., 1995, *Proc. Natl. Acad. Sci. USA* 92:11249-53).

In marked contrast to the restricted expression of CD27 and CD70 in normal B lineage cells, both CD27 and CD70 are frequently co-expressed in many B cell non-Hodgkin's lymphomas and leukemias. This could potentially lead to functional CD27-CD70 interactions on these cells in the form of an autocrine loop, resulting in CD27 signaling and in CD70-induced proliferation, thereby providing a growth advantage to malignant cells (Lens et al., 1999, supra).

The role of CD70-CD27 co-stimulation in cell-mediated autoimmune diseases has been investigated in a model of experimental autoimmune encephalomyelitis (EAE) (Nakajima et al., 2000, *J. Neuroimmunol.* 109:188-96). In vivo administration of the anti-mouse CD70 mAb (clone FR-70) suppressed the onset of EAE by inhibiting antigen-induced TNF-alpha production without affecting B and T cell number, T cell priming, Ig production or $T_H1/T_H2$ cell balance. However, such treatment had little efficacy in established disease.

Graft versus host disease (GVHD) is a $T_H1$-mediated immune response that is a major and often lethal consequence of allogeneic bone marrow transplantation (BMT) therapy that occurs when histocompatibility antigen differences between the BM donor and the recipient of the transplant are present (den Haan et al., 1995, *Science* 268:1476). GVHD is an immune reaction against host tissues mounted by mature T cells present in the transplanted donor marrow (Giralt and Champlin, 1994, *Blood* 84:3603). It is noteworthy that CD70 has been detected in vivo on CD4+ cells in conditions characterized by allogeneic reaction, as in cases of maternal T cell engraftment in severe combined immune deficiency patients (Brugnoni et al., 1997, *Immunol. Lett.* 55:99-104). Prophylaxis of GVHD is achieved by pan-T cell immunomodulatory agents such as cyclosporine, corticosteroids, or methotrexate. However, these agents are not specific and cause significant adverse side effects.

As indicated supra, CD70 is not expressed on normal non-hematopoietic cells. CD70 expression is mostly restricted to recently antigen-activated T and B cells under physiological conditions, and its expression is down-regulated when antigenic stimulation ceases. Evidence from animal models suggests that CD70 may contribute to immunological disorders such as, e.g., rheumatoid arthritis (Brugnoni et al., 1997, *Immunol. Lett.* 55:99-104), psoriatic arthritis (Brugnoni et al., 1997, *Immunol Lett.* 55:99-104), and systemic lupus erythematosus (SLE). (Oelke et al., 2004, *Arthritis Rheum.* 50:1850-60). In addition to its potential role in inflammatory responses, CD70 is also expressed on a variety of transformed cells including lymphoma B cells, Hodgkin and Reed-Sternberg cells, malignant cells of neural origin, and a number of carcinomas.

Accordingly, there is a need for anti-CD70 antibodies and other CD70 binding agents that can exert a clinically useful cytotoxic, cytostatic, or immunomodulatory effect on CD70-expressing cells, particularly without exerting undesirable effects on non-CD70-expressing cells. Such binding agents would be useful against cancers that express CD70 or immune disorders that are mediated by CD70-expressing cells.

BRIEF SUMMARY OF THE INVENTION

The present invention provides CD70 antibodies and other CD70 binding agents and methods relating to the use of such binding agents for the prophylaxis or treatment of CD70-expressing cancers and immunological disorders where CD70-expressing cells are present. The antibody or other binding agent binds to CD70 and exhibits a cytotoxic, cytostatic, and/or immunomodulatory effect on CD70-expressing cells in the absence of conjugation to a therapeutic agent.

In one aspect, a method of treating a CD70-expressing cancer in a subject is provided. The method generally includes administering to the subject an effective amount of a binding agent having an antigen-binding region that binds to CD70, and at least one effector domain mediating at least an ADCC, ADCP or CDC response in the subject, wherein the binding agent exerts a cytostatic or cytotoxic effect in the absence of conjugation to a therapeutic agent. The CD70 binding agent can be, for example, an antibody, such as a chimeric, humanized, or fully human antibody. The antibody can include, for example, an effector domain of a human IgM or IgG antibody. The IgG antibody can be, for example, a human IgG1 or IgG3 subtype. In some embodiments, the antibody includes a human constant region.

In some embodiments, the antibody competes for binding to CD70 with monoclonal antibody 1F6 or 2F2. In other embodiments, the antibody is a humanized 1F6 or 2F2 or a chimeric 1F6 or 2F2 antibody. The antibody can be, for example, monovalent, divalent or multivalent.

The CD70-expressing cancer can be, for example, a kidney tumor, a B cell lymphoma, a colon carcinoma, Hodgkin's Disease, multiple myeloma, Waldenstrom macroglobulinemia, non-Hodgkin's lymphoma, a mantle cell lymphoma, chronic lymphocytic leukemia, acute lymphocytic leukemia, a nasopharyngeal carcinoma, brain tumor or a thymic carcinoma. The kidney tumor can be, for example, a renal cell carcinoma. The brain tumor can be, for example, a glioma, a glioblastoma, an astrocytoma or a meningioma. The subject can be, for example, a mammal, such as a human being.

In another aspect, a method for treating an immunological disorder is provided. The method includes administering to a subject an effective amount of a binding agent having an antigen-binding region that binds to CD70, and at least one effector domain mediating at least an ADCC, ADCP or CDC response in the subject, wherein the binding agent exerts a cytostatic, cytotoxic, or immunomodulatory effect in the absence of conjugation to a therapeutic agent. The CD70 binding agent can be, for example, an antibody, such as a chimeric, humanized, or fully human antibody. The antibody can include, for example, an effector domain of a human IgM or IgG antibody. The IgG antibody can be, for example, a human IgG1 or IgG3 subtype. In some embodiments, the antibody includes a human constant region.

In some embodiments, the antibody competes for binding to CD70 with monoclonal antibody 1F6 or 2F2. In other embodiments, the antibody is a humanized 1F6 or 2F2 or a chimeric 1F6 or 2F2 antibody. The antibody can be, for example, monovalent, divalent or multivalent.

The immunological disorder can be, for example, a T cell-mediated immunological disorder. In some embodiments, the T cell mediated immunogical disorder comprises activated T cells expressing CD70. In some embodiments, resting T cells are not substantially depleted by administration of the antibody. The T cell-mediated immunological disorder also can be, for example, rheumatoid arthritis, systemic lupus erythematosus (SLE), Type I diabetes, asthma, atopic dermatitis, allergic rhinitis, thrombocytopenic purpura, multiple sclerosis, psoriasis, Sjögren's syndrome, Hashimoto's thyroiditis, Graves' disease, primary biliary cirrhosis, Wegener's granulomatosis, tuberculosis, or graft versus host disease. In other embodiments, the immunological disorder is an activated B-lymphocyte disorder. The subject can be, for example, a mammal, such as a human being.

In another aspect, an antibody that includes an antigen-binding region that binds to CD70 is provided. The antibody includes at least one effector domain mediating at least an ADCC, ADCP or CDC response in a subject, and exerts a cytostatic or cytotoxic effect on a CD70 expressing cancer, which cytostatic or cytotoxic effect is achieved in the absence of conjugation to a cytostatic or cytotoxic agent, and wherein the antibody is not monoclonal antibody 1F6 or 2F2. The antibody can compete for binding to CD70 with monoclonal antibody 1F6 and 2F2.

In another aspect, the antibody includes an antigen-binding region that binds to CD70, and at least one effector domain mediating at least an ADCC, ADCP or CDC response in a subject, and exerts an immunomodulatory effect on a CD70 expressing immunological disorder, which immunomodulatory effect is achieved in the absence of conjugation to a cytostatic or cytotoxic agent, and wherein the antibody is not monoclonal antibody 1F6 or 2F2. The antibody can compete for binding to CD70 with monoclonal antibody 1F6 and 2F2.

In a related aspect, also provided is a pharmaceutical composition for the treatment of a CD70-expressing cancer or an immunological disorder. The composition includes a CD70 binding antibody and at least one pharmaceutically compatible ingredient. Further provided is a pharmaceutical kit including a container including a CD70 binding antibody, wherein the antibody is lyophilized, and a second container comprising a pharmaceutically acceptable diluent.

The present invention may be more fully understood by reference to the following detailed description of the invention, non-limiting examples of specific embodiments of the invention and the appended figures.

BRIEF DESCRIPTION OF THE DRAWINGS

FIG. 1. The 1F6 $V_L$ and $V_H$ cDNA and amino acid sequences. The coding and amino acid sequences for the light ($V_L$, upper 2 panels; SEQ ID NOs: 11 and 12) and heavy chain ($V_H$, lower 2 panels; SEQ ID NOs: 1 and 2) variable regions of 1F6 were determined. The complementarity determining regions (CDRs) for the $V_L$ and $V_H$ were identified according to criteria described in Kabat et al. (1991, *Sequences of Proteins of Immunogical Interest*, Washington, D.C., US Department of Health and Public Services; Chothia and Lesk, 1987, *J. Mol. Biol.* 196: 901-17). Amino acid residues corresponding to the CDRs are underlined. The signal peptide for the $V_L$ and $V_H$ are identified to be amino residues –20 to 0 and –19 to 0, respectively.

FIG. 2. The 2F2 $V_L$ and $V_H$ cDNA and amino acid sequences. The coding and amino acid sequences for the light ($V_L$, upper 2 panels; SEQ ID NOs:31 and 32) and heavy chain ($V_H$, lower 2 panels; SEQ ID NOs:21 and 22) variable regions of 2F2 were determined. The complementarity determining regions (CDRs) for the $V_L$ and $V_H$ were identified according to criteria described in Kabat et al., supra; Chothia and Lesk, supra. Amino acid residues corresponding to the CDRs are underlined. The signal peptides for the $V_L$ and $V_H$ were identified to be amino residues –20 to 0 and –19 to 0, respectively.

FIG. 3. Amino acid sequence comparisons between the 1F6 and 2F2 CDRs L1, L2, L3, H1, H2 and H3 (SEQ ID NOs:16 and 36, SEQ ID NOs:18 and 38, SEQ ID NOs:20 and 40, residues 45-54 of SEQ ID NO:2 and SEQ ID NO:26, SEQ ID NOs:8 and 28, and SEQ ID NOs:10 and 30, respectively). The amino acid sequences of 1F6 and 2F2 CDRs are aligned. Underlined residues represent conservative substitutions and boxed and italic residues represent divergent substitutions.

FIG. 15. Chimeric 1F6 mediates ADCP against multiple CD70+ cell targets. The indicated CD70+ lymphoma, multiple myeloma, and renal cell carcinoma cell lines were used as targets for chimeric 1F6-mediated ADCP assays as described in FIG. 15. Percentage specific ADCP activity at saturating concentrations of chimeric 1F6 is tabulated.

FIG. 16. In vivo antitumor activity of c1F6 in CD70+ xenograft lymphoma models. SCID mice (n=10/group) were inoculated intravenously with $1 \times 10^6$ Ramos cells or IM-9 cells one day prior to drug treatment. A single dose of chimeric 1F6 was administered at 1 or 4 mg/kg and a single dose of the non-binding control antibody (IgG) was administered at 4 mg/kg. Survival was monitored and the difference(s) between treatment groups was compared using the log-rank test as indicated by the P values.

DETAILED DESCRIPTION

Figure 4:
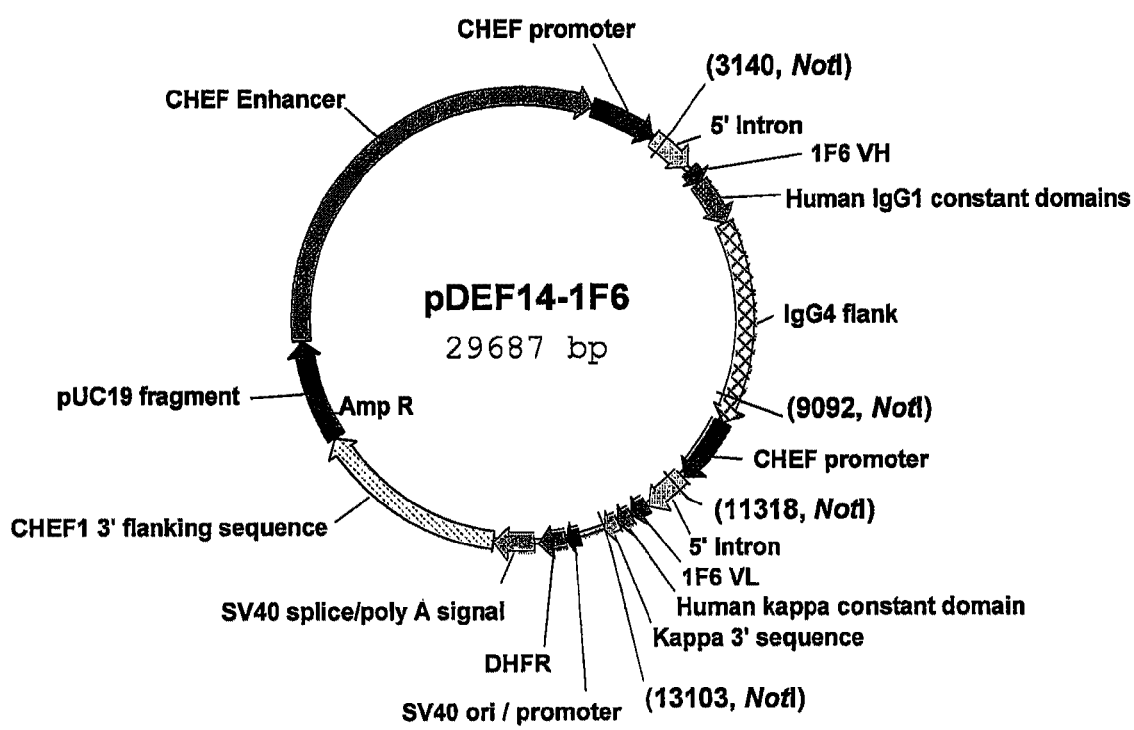
FIG. 4. Chimeric 1F6 Expression Vector pDEF14-1F6. The structure of an expression vector for expression of antibodies is shown.

The present invention provides CD70 binding agent and methods for using such binding agents for the prophylaxis or treatment of CD70-expressing cancers and immunological disorders. The CD70 binding agent includes a domain that binds to CD70 (e.g., the extracellular domain of human CD70) and an effector domain. The present inventors have discovered that a CD70 binding agent containing an effector domain can induces a cytotoxic, cytostatic, or immunomodulatory effect on CD70-expressing cells in the absence of conjugation to a therapeutic agent. The cytotoxic, cytostatic, or immunomodulatory effect can be induced, for example, by recruiting and activating cytotoxic white blood cells, e.g., natural killer (NK) cells, phagocytic cells (e.g., macrophages) and/or serum complement components.

In one aspect, the methods and compositions relate to antibodies and antibody derivatives that bind to CD70. In an exemplary embodiment, the antibodies or derivatives thereof compete with monoclonal antibody 1F6 or 2F2 for binding to CD70. A cytotoxic, cytostatic, and/or immunomodulatory effect is mediated by the CD70 antibody or derivative and effector cells or complement components that interact with an effector domain (e.g., an Fc region) of the antibody. The cytotoxic, cytostatic, and/or immunomodulatory effect depletes or inhibits the proliferation of CD70-expressing cells. CD70 antibodies can be monoclonal, chimeric, humanized, or human antibodies. In some embodiments, the antibody constant regions are of the IgG subtype. In some embodiments, the antibody is not a mouse monoclonal antibody.

In another aspect, the methods and compositions relate to other CD70 binding agents that bind to CD70. The CD70 binding agent binds to an extracellular domain of CD70. A cytotoxic, cytostatic, and/or immunomodulatory effect is mediated by the CD70 binding agent and effector cells or complement components that interact with an effector domain (e.g., an Fc region). The cytotoxic, cytostatic, and/or immunomodulatory effect depletes or inhibits the proliferation of CD70-expressing cells. CD70 binding agents can be, for example, CD27 and derivatives thereof.

I. Definitions and Abbreviations

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "inhibit" or "inhibition of" as used herein means to reduce by a measurable amount, or to prevent entirely.

The term "CD70 binding agent" as used herein means an anti-CD70 antibody, a derivative of an anti-CD70 antibody, or other agent that binds to CD70, such as an extracellular domain or a portion thereof.

A "therapeutic agent" is an agent that exerts a cytotoxic, cytostatic, or immunomodulatory effect on cancer cells or activated immune cells.

A "cytotoxic effect" refers to the depletion, elimination and/or the killing of a target cell. A "cytotoxic agent" refers to an agent that has a cytotoxic effect on a cell.

A "cytostatic effect" refers to the inhibition of cell proliferation. A "cytostatic agent" refers to an agent that has a cytostatic effect on a cell (or a specific subset of cells), thereby inhibiting the growth and/or expansion of the cell (or specific subset of cells).

The term "deplete," in the context of the effect of a CD70 binding agent on CD70-expressing cells, refers to a reduction or elimination of the CD70-expressing cells.

The term "immunomodulatory agent" as used herein refers to an agent that modulates the development or maintenance of an immunologic response. Such modulation can be effected by, for example, elimination of immune cells (e.g., T or B lymphocytes); induction or generation of immune cells that can modulate (e.g., down-regulate) the functional capacity of other cells; induction of an unresponsive state in immune cells (e.g., anergy); or increasing, decreasing or changing the activity or function of immune cells, including, for example, altering the pattern of proteins expressed by these cells (e.g., altered production and/or secretion of certain classes of molecules such as cytokines, chemokines, growth factors, transcription factors, kinases, costimulatory molecules or other cell surface receptors, and the like). In typical embodiments, an immunomodulatory agent has a cytotoxic or cytostatic effect on an immune cell that promotes an immune response.

"Immune cell" as used herein refers to a cell of hematopoietic lineage involved in regulating an immune response. In typical embodiments, an immune cell is a T lymphocyte, a B lymphocyte, an NK cell, a monocyte/macrophage, or a dendritic cell.

The term "polypeptide" refers to a polymer of amino acids and its equivalent and does not refer to a specific length of a product; thus, "peptides" and "proteins" are included within the definition of a polypeptide. Also included within the definition of polypeptides are "antibodies" as defined herein. A "polypeptide region" refers to a segment of a polypeptide, which segment may contain, for example, one or more domains or motifs (e.g., a polypeptide region of an antibody can contain, for example, one or more complementarity determining regions (CDRs)). The term "fragment" refers to a portion of a polypeptide typically having at least 20 contiguous or at least 50 contiguous amino acids of the polypeptide. A "derivative" is a polypeptide or fragment thereof having one or more non-conservative or conservative amino acid substitutions relative to a second polypeptide; or a polypeptide or fragment thereof that is modified by covalent attachment of a second molecule such as, e.g., by attachment of a heterologous polypeptide, or by glycosylation, acetylation, phosphorylation, and the like. Further included within the definition of "derivative" are, for example, a polypeptides containing one or more analogs of an amino acid (e.g., unnatural amino acids and the like), polypeptides with unsubstituted linkages, as well as other modifications known in the art, both naturally and non-naturally occurring.

The term "antibody" as used herein refers to (a) immunoglobulin polypeptides and immunologically active portions of immunoglobulin polypeptides (i.e., polypeptides of the immunoglobulin family, or fragments thereof, that contain an antigen binding site that immunospecifically binds to a specific antigen (e.g., CD70)), or (b) conservatively substituted derivatives of such immunoglobulin polypeptides or fragments that immunospecifically bind to the antigen (e.g., CD70). Antibodies are generally described in, for example, Harlow and Lane, Antibodies: *A Laboratory Manual* (Cold Spring Harbor Laboratory Press, 1988).

In the context of immunoglobulin polypeptides or fragments thereof as defined above, "conservative substitution" means one or more amino acid substitutions that do not substantially reduce specific binding (e.g., as measured by the $K_D$) of the immunoglobulin polypeptide or fragment thereof to an antigen (i.e., substitutions that increase binding, that do not significantly alter binding, or that reduce binding by no more than about 40%, typically no more than about 30%, more typically no more than about 20%, even more typically no more than about 10%, or most typically no more than about 5%, as determined by standard binding assays such as, e.g., ELISA).

An "antibody derivative" as used herein refers to an antibody, as defined above, that is modified by covalent attachment of a heterologous molecule such as, e.g., by attachment of a heterologous polypeptide, or by glycosylation, acetylation or phosphorylation not normally associated with the antibody, and the like. In some embodiments, the heterologous molecule is not a therapeutic agent. In some embodiments, the heterologous molecule does not exhibit a cytostatic or cytotoxic effect by itself.

The term "monoclonal antibody" refers to an antibody that is derived from a single cell clone, including any eukaryotic or prokaryotic cell clone, or a phage clone, and not the method by which it is produced. Thus, the term "monoclonal antibody" as used herein is not limited to antibodies produced through hybridoma technology.

The term "heterologous," in the context of a polypeptide, means from a different source (e.g., a cell, tissue, organism, or species) as compared with another polypeptide, so that the two polypeptides are different. Typically, a heterologous polypeptide is from a different species.

As used herein, the term "functional," in the context of an CD70 binding agent indicates that the binding agent is (1) capable of binding to CD70 and (2) depletes or inhibits the proliferation of CD70-expressing cells without conjugation to a cytotoxic or cytostatic agent, or has an immunosuppressive effect on an immune cell without conjugation to an immunomodulatory agent.

The term "antibody effector function(s)," as used herein refers to a function contributed by an Fc effector domain(s) of an Ig (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the CD70 targeted cell.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a tumor cell and Fcγ receptors, particularly FcγRI and FcγRIII, on immune effector cells such as neutrophils, macrophages and natural killer cells. The tumor cell is eliminated by phagocytosis or lysis, depending upon the type of mediating effector cell. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an immunoglobulin Fc region.

The term "complement-dependent cytotoxicity" or CDC refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

The terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences are the same length.

The term "substantially identical," in the context of two nucleic acids or polypeptides, refers to two or more sequences or subsequences that have at least 50%, at least 55%, at least 60%, or at least 65% identity; typically at least 70% or at least 75% identity; more typically at least 80% or at least 85% identity; and even more typically at least 90%, at least 95%, or at least 98% identity (e.g., as determined using one of the methods set forth infra).

The terms "similarity" or "percent similarity" in the context of two or more polypeptide sequences, refer to two or more sequences or subsequences that have a specified percentage of amino acid residues that are the same or conservatively substituted when compared and aligned for maximum correspondence, as measured using one of the methods set forth infra. By way of example, a first amino acid sequence can be considered similar to a second amino acid sequence when the first amino acid sequence is at least 50%, 60%, 70%, 75%, 80%, 90%, or 95% identical, or conservatively substituted, to the second amino acid sequence when compared to an equal number of amino acids as the number contained in the first sequence, or when compared to an alignment of polypeptides that has been aligned by a, e.g., one of the methods set forth infra.

The terms "substantial similarity" or "substantially similar," in the context of polypeptide sequences, indicates that a polypeptide region has a sequence with at least 70%, typically at least 80%, more typically at least 85%, or at least 90% or at least 95% sequence similarity to a reference sequence. For example, a polypeptide is substantially similar to a second polypeptide, when the two peptides differ by one or more conservative substitutions.

In the context of anti-CD70 antibodies or derivatives thereof, a protein that has one or more polypeptide regions substantially identical or substantially similar to one or more antigen-binding regions (e.g., a heavy or light chain variable region, or a heavy or light chain CDR) of an anti-CD70 antibody retains specific binding to an epitope of CD70 recognized by the anti-CD70 antibody, as determined using any of various standard immunoassays known in the art or as referred to herein.

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (id.). When utilizing BLAST, Gapped BLAST, and PSI-Blast programs, the default parameters of the respective programs (e.g., XBLAST and NBLAST) can be used Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA.

Alternatively, protein sequence alignment may be carried out using the CLUSTAL W algorithm, as described by Higgins et al, 1996, *Methods Enzymol.* 266:383-402.

As used herein, the terms "prevention" or "prevent" refer to administration of an anti-CD70 antibody or derivative or other binding agent to a subject before the onset of a clinical or diagnostic symptom of a CD70-expressing cancer or immunological disorder (e.g., administration to an individual with a predisposition or at a high risk of acquiring the CD70-expressing cancer or immunological disorder) to (a) block the occurrence or onset of the CD70-expressing cancer or immunological disorder, or one or more of clinical or diagnostic symptoms thereof, (b) inhibit the severity of onset of the CD70-expressing cancer or immunological disorder, or (c) to lessen the likelihood of the onset of the CD70-expressing cancer or immunological disorder.

As used herein, the terms "treatment" or "treat" refer to slowing, stopping, and/or reversing the progression of a CD70-expressing cancer or immunological disorder in a subject, as evidenced by a decrease or elimination of a clinical or diagnostic symptom of the disease, by administration of an anti-CD70 antibody or derivative thereof or other binding agent to the subject after the onset of the clinical or diagnostic symptom of the CD70-expressing cancer or immunological disorder at any clinical stage. Treatment can include, for example, a decrease in the severity of a symptom, the number of symptoms, or frequency of relapse.

The term "pharmaceutically acceptable" as used herein means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-CD70 binding agent is administered.

The term "effective amount" refers to the amount of the antibody or derivative or other binding agent that is sufficient to inhibit the occurrence or ameliorate one or more clinical or diagnostic symptoms of a CD70-expressing cancer or immunological disorder in a subject. An effective amount of an agent is administered according to the methods described herein in an "effective regime." The term "effective regime" refers to a combination of amount of the agent and dosage frequency adequate to accomplish treatment or prevention of a CD70-expressing cancer or immunological disorder.

II. Anti-CD70 Antibodies and Derivatives Thereof

The methods and compositions described herein encompass the use of a CD70 binding agent that specifically binds to CD70 and exerts a cytotoxic, cytostatic or immunomodulatory effect on CD70-expressing cancer cells or activated immune cells. The CD70 binding agent can be, for example, an anti-CD70 antibody, an antigen-binding fragment of an anti-CD70 antibody, a derivative thereof, or other CD70 binding agent. The CD70 binding agent includes an antibody effector domain function that mediates or stimulates ADCC, ADCP and/or CDC responses against a CD70-expressing target cell. The effector domain(s) can be, for example, an Fc region of an Ig molecule. The CD70 binding agent exerts a cytotoxic or cytostatic effect on CD70-expressing cancer cells, or exerts a cytotoxic, cytostatic, or immunomodulatory effect on activated lymphocytes or dendritic cells, for the treatment of a CD70-expressing cancer or an immunological disorder, respectively. Typically, the CD70 binding agent recruits and/or activates cytotoxic white blood cells (e.g., natural killer (NK) cells, phagocytotic cells (e.g., macrophages), and/or serum complement components). In some embodiments, the CD70 binding agent is monoclonal antibody (mAb) 1F6 or 2F2 or a derivative thereof. In other embodiments, the anti-CD70 antibody or derivative thereof competes with monoclonal antibody 1F6 or 2F2 for binding to CD70. In some embodiments, the CD70 binding agent is agonistic. In some embodiments, the CD70 binding agent is antagonistic. In some embodiments, the CD70 binding agent blocks binding to CD27.

An anti-CD70 antibody typically is or is derived from a monoclonal antibody and can include, for example, a chimeric (e.g., having a human constant region and mouse variable region), a humanized, or a fully human antibody; a single chain antibody; a maxibody, a minibody, an antigen binding region, or the like. The antibody molecule includes at least one effector domain that can functionally interact with and activate cytotoxic white blood cells and/or serum complement components. In some embodiments, a CD70 antigen binding region can be joined to an effector domain or domains such as, for example, hinge-$C_H2$-$C_H3$ domains of an immunoglobulin, or a portion or fragment of an effector domain(s) having effector function. Antigen-binding antibody fragments, including single-chain antibodies, can comprise for example the variable region(s) in combination with the entirety or a portion of an effector domain (e.g., a $C_H2$ and/or $C_H3$ domain alone or in combination with a $C_H1$, hinge and/or $C_L$ domain). Also, antigen-binding fragments can comprise any combination of effector domains. In some embodiments, the anti-CD70 antibody can be a single chain antibody comprising a CD70 binding variable region joined to hinge-$C_H2$-$C_H3$ domains.

Typically, the antibodies are of human, or non-human origin (e.g., rodent (e.g., mouse or rat)), donkey, sheep, rabbit, goat, guinea pig, camelid, horse, or chicken) of specific Ig isotypes that can mediate effector function. As used herein, "human" antibodies include antibodies having the amino acid sequence of a human immunoglobulin and include antibodies isolated from human immunoglobulin libraries, from human B cells, or from animals transgenic for one or more human immunoglobulin, as described infra and, for example in U.S. Pat. Nos. 5,939,598 and 6,111,166.

The effector domain of an antibody can be from any suitable vertebrate animal species and isotypes. The isotypes from different animal species differ in the abilities to mediate effector functions. For example, the ability of human immunoglobulin to mediate CDC and ADCC/ADCP is generally in the order of IgM≈IgG1≈IgG3>IgG2>IgG4 and IgG1≈IgG3>IgG2/IgM/IgG4, respectively. Murine immunoglobulins mediate CDC and ADCC/ADCP generally in the order of murine IgM≈IgG3>>IgG2b>IgG2a>>IgG1 and IgG2b>IgGa>IgG1>>IgG3, respectively. In another example, murine IgG2a mediates ADCC while both murine IgG2a and IgM mediate CDC. In some embodiments, the CD70 binding agent consists of antibody variable and effector domains. In other embodiments, the CD70 binding agent consists essentially of antibody variable and effector domains, and can further include an additional compound(s) that is not a therapeutic agent(s). A CD70 binding polypeptide also can be expressed as a recombinant fusion protein comprising of the appropriate constant domains to yield the desired effector function(s).

Upon binding to target cells, the antibodies or derivatives can trigger in vitro and in vivo target cell destruction through effector domain (e.g., Fc-) mediated effector functions. Without intending to be bound by any particular theory, Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by CD16[+] effector cells through the secretion of membrane pore-forming proteins and proteases, while phagocytosis is mediated by CD32[+] and CD64[+] effector cells (see *Fundamental Immunology*, 4th ed., Paul ed., Lippincott-Raven, N.Y., 1997, Chapters 3, 17 and 30; Uchida et al., 2004, J. Exp. Med. 199:1659-69; Akewanlop et al., 2001, Cancer Res. 61:4061-65; Watanabe et al., 1999, Breast Cancer Res. Treat. 53:199-207). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see Immunobiology, 6$^{th}$ ed., Janeway et al., Garland Science, N.Y., 2005, Chapter 2).

The antibodies can be monospecific, bispecific, trispecific, or of greater multispecificity. Multispecific antibodies may be specific for different epitopes of CD70 and/or may be specific for both CD70 as well as for a heterologous protein. (See, e.g., PCT Publications WO 93/17715, WO 92/08802, WO 91/00360, and WO 92/05793; Tutt et al., 1991, J. Immunol. 147:60-69; U.S. Pat. Nos. 4,474,893; 4,714,681; 4,925,648; 5,573,920; and 5,601,819; Kostelny et al., 1992, J. Immunol. 148:1547-1553.) Multispecific antibodies, including bispecific and trispecific antibodies, useful for practicing the methods described herein are antibodies that immunospecifically bind to both CD70 (including but not limited to antibodies that have the CDRs of the monoclonal antibodies 2F2 or 1F6) and a second cell surface receptor or receptor complex that mediates ADCC, phagocytosis, and/or CDC, such as CD16/FcgRIII, CD64/FcgRI, killer inhibitory or activating receptors, or the complement control protein CD59. In a typical embodiment, the binding of the portion of the multispecific antibody to the second cell surface molecule or receptor complex enhances the effector functions of the anti-CD70 antibody or other CD70 binding agent.

In one aspect, an anti-CD70 antibody comprises one or more complementarity determining regions (CDRs) substantially identical or substantially similar to one or more CDR(s) of monoclonal antibody 1F6 (see Table 1). For example, the antibody can include a heavy chain CDR and/or a light chain CDR that is substantially identical or substantially similar to a corresponding heavy chain CDR (H1, H2, or H3 regions) or corresponding light chain CDR (L1, L2, or L3 regions) of mAb 1F6 (residues 45-54 of SEQ ID NO:2; SEQ ID NO:8; SEQ ID NO:10; SEQ ID NO:16; SEQ ID NO:18; or SEQ ID NO:20, respectively). In typical embodiments, the anti-CD70 antibody has two or three heavy chain CDRs and/or two or three light chain CDRs that are substantially identical or substantially similar to corresponding heavy and/or light chain CDRs of mAb 1F6. In specific embodiments, a CDR substantially identical or substantially similar to a heavy or light chain CDR of 1F6 has the amino acid sequence set forth in residues 45-54 of SEQ ID NO:2, SEQ ID NO:8, SEQ ID NO:10, SEQ ID NO:16, SEQ ID NO:18, or SEQ ID NO:20.

For example, in some embodiments, where an anti-CD70 antibody has at least one heavy chain CDR substantially identical or substantially similar to a heavy chain CDR of mAb 1F6, the antibody or derivative thereof further includes at least one light chain CDR that is substantially identical or substantially similar to a light chain CDR of mAb 1F6.

In some embodiments, an anti-CD70 antibody includes a heavy or light chain variable domain, the variable domain having (a) a set of three CDRs substantially identical or substantially similar to corresponding CDRs of mAb 1F6, and (b) a set of four framework regions. For example, an anti-CD70 antibody can include a heavy or light chain variable domain, the variable domain having (a) a set of three CDRs, in which the set of CDRs are from monoclonal antibody 1F6, and (b) a set of four framework regions of the IgG type.

In some embodiments, the anti-CD70 antibody is a chimeric antibody. A chimeric antibody is a molecule in which different portions of the antibody are derived from different animal species, such as for example antibodies having a variable region derived from a murine monoclonal antibody and a human IgG immunoglobulin constant region. Methods for producing chimeric antibodies are known in the art. (See e.g., Morrison, Science, 1985, 229:1202; Oi et al., 1986, BioTechniques 4:214; Gillies et al., 1989, J. Immunol. Methods 125:191-202; U.S. Pat. Nos. 5,807,715; 4,816,567; and 4,816,397.)

In an exemplary embodiment, the anti-CD70 antibody is a chimeric antibody that includes a heavy chain variable region that is substantially identical or substantially similar to the heavy chain variable region of mAb 1F6 (i.e., substantially identical or substantially similar to the amino acid sequences set forth in SEQ ID NO:2, see Table 1) and/or a light chain variable region that is substantially identical or substantially similar to the light chain variable regions of mAb 1F6 (i.e., substantially identical or substantially similar to the amino acid sequences set forth in SEQ ID NO:12, see Table 1). For example, the antibody can include a heavy chain variable region having the amino acid sequence set forth in SEQ ID NO:2 and, optionally, can further include a light chain variable region having the amino acid sequence set forth in SEQ ID NO:12. The heavy and light chain antibody constant regions are of the IgG type. In an exemplary embodiment, the anti-CD70 antibody is a chimeric IgG mAb 1F6.

In some embodiments, an anti-CD70 antibody is a chimeric antibody that includes one or more CDRs substantially identical or substantially similar to one or more CDR(s) of monoclonal antibody 2F2 (see Table 1). For example, the antibody can include a heavy chain CDR and/or a light chain CDR that is substantially identical or substantially similar to a corresponding heavy chain CDR (H1, H2, or H3 regions) or corresponding light chain CDR (L1, L2, or L3 regions) of mAb 2F2 (SEQ ID NO:26, SEQ ID NO:28; SEQ ID NO:30; SEQ ID NO:36, SEQ ID NO:38 or SEQ ID NO:40). In typical embodiments, the anti-CD70 antibody has two or three heavy chain CDRs and/or two or three light chain CDRs that are substantially identical or substantially similar to corresponding heavy and/or light chain CDRs of mAb 2F2. In specific embodiments, a CDR substantially identical or substantially similar to a heavy or light chain CDR of 2F2 has the amino acid sequence set forth in SEQ ID NO:26, SEQ ID NO:28, SEQ ID NO:30; SEQ ID NO:36, SEQ ID NO:38, or SEQ ID NO:40.

For example, in some embodiments, where an anti-CD70 antibody has at least one heavy chain CDR substantially identical or substantially similar to a heavy chain CDR of mAb 2F2, the antibody or derivative thereof further includes at least one light chain CDR that is substantially identical or substantially similar to a light chain CDR of mAb 2F2.

In some embodiments, an anti-CD70 antibody includes a heavy or light chain variable domain, the variable domain having (a) a set of three CDRs substantially identical or substantially similar to corresponding CDRs of mAb 2F2, and (b) a set of four framework regions. For example, an anti-CD70 antibody can include a heavy or light chain variable domain, the variable domain having (a) a set of three CDRs, in which the set of CDRs are from monoclonal antibody 2F2, and (b) a set of four framework regions, in which the set of framework regions are of the IgG type. In an exemplary embodiment, the anti-CD70 antibody is a chimeric IgG mAb 2F2.

In an embodiment, the anti-CD70 antibody includes a heavy chain variable region that is substantially identical or substantially similar to the heavy chain variable region of mAb 2F2 (i.e., substantially identical or substantially similar to the amino acid sequences set forth in SEQ ID NO:22, see Table 1) and/or a light chain variable region that is substantially identical or substantially similar to the light chain variable regions of mAb 2F2 (i.e., substantially identical or substantially similar to the amino acid sequences set forth in SEQ ID NO:32, see Table 1). For example, the antibody can include a heavy chain variable region having the amino acid sequence set forth in SEQ ID NO:22 and, optionally, can further include a light chain variable region having the amino acid sequence set forth in SEQ ID NO:32. In one exemplary embodiment, the anti-CD70 antibody is mAb 2F2.

In some embodiments, the antibody comprises a 1F6 $V_H$ and a 2F2 $V_L$ or a 1F6 $V_H$ and a 2F2 $V_L$.

The following table indicates the regions of 1F6 or 2F2 to which each SEQ ID NO. corresponds.

TABLE 1

| MOLECULE | NUCLEOTIDE OR AMINO ACID | SEQ ID NO |
|---|---|---|
| 1F6 Heavy Chain Variable Region | Nucleotide | 1 |
| 1F6 Heavy Chain Variable Region | Amino Acid | 2 |
| 1F6 Heavy Chain Signal Peptide | Nucleotide | 3 |
| 1F6 Heavy Chain Signal Peptide | Amino Acid | 4 |
| 1F6 Heavy Chain-CDR1(H1) | Nucleotide | 5 |
| 1F6 Heavy Chain-CDR1(H1) | Amino Acid | 2 (residues 45-54) |
| 1F6 Heavy Chain-CDR2(H2) | Nucleotide | 7 |
| 1F6 Heavy Chain-CDR2(H2) | Amino Acid | 8 |
| 1F6 Heavy Chain-CDR3(H3) | Nucleotide | 9 |
| 1F6 Heavy Chain-CDR3(H3) | Amino Acid | 10 |
| 1F6 Light Chain Variable Region | Nucleotide | 11 |
| 1F6 Light Chain Variable Region | Amino Acid | 12 |
| 1F6 Light Chain Signal Peptide | Nucleotide | 13 |
| 1F6 Light Chain Signal Peptide | Amino Acid | 14 |
| 1F6 Light Chain-CDR1(L1) | Nucleotide | 15 |
| 1F6 Light Chain-CDR1(L1) | Amino Acid | 16 |
| 1F6 Light Chain-CDR2(L2) | Nucleotide | 17 |
| 1F6 Light Chain-CDR2(L2) | Amino Acid | 18 |
| 1F6 Light Chain-CDR3(L3) | Nucleotide | 19 |
| 1F6 Light Chain-CDR3(L3) | Amino Acid | 20 |
| 2F2 Heavy Chain Variable Region | Nucleotide | 21 |
| 2F2 Heavy Chain Variable Region | Amino Acid | 22 |
| 2F2 Heavy Chain Signal Peptide | Nucleotide | 23 |
| 2F2 Heavy Chain Signal Peptide | Amino Acid | 24 |
| 2F2 Heavy Chain-CDR1(H1) | Nucleotide | 25 |
| 2F2 Heavy Chain-CDR1(H1) | Amino Acid | 26 |
| 2F2 Heavy Chain-CDR2(H2) | Nucleotide | 27 |
| 2F2 Heavy Chain-CDR2(H2) | Amino Acid | 28 |
| 2F2 Heavy Chain-CDR3(H3) | Nucleotide | 29 |
| 2F2 Heavy Chain-CDR3(H3) | Amino Acid | 30 |
| 2F2 Light Chain Variable Region | Nucleotide | 31 |
| 2F2 Light Chain Variable Region | Amino Acid | 32 |
| 2F2 Light Chain Signal Peptide | Nucleotide | 33 |
| 2F2 Light Chain Signal Peptide | Amino Acid | 34 |
| 2F2 Light Chain-CDR1(L1) | Nucleotide | 35 |
| 2F2 Light Chain-CDR1(L1) | Amino Acid | 36 |
| 2F2 Light Chain-CDR2(L2) | Nucleotide | 37 |
| 2F2 Light Chain-CDR2(L2) | Amino Acid | 38 |
| 2F2 Light Chain-CDR3(L3) | Nucleotide | 39 |
| 2F2 Light Chain-CDR3(L3) | Amino Acid | 40 |

Anti-CD70 antibodies and derivatives thereof and other binding agents may also be described or specified in terms of their binding affinity to CD70. Typical binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The antibodies can be generated by methods known in the art. For example, monoclonal antibodies can be prepared using a wide variety of techniques including, e.g., the use of hybridoma, recombinant, and phage display technologies, or a combination thereof. Hybridoma techniques are generally discussed in, for example, Harlow et al., *Antibodies: A Laboratory Manual* (Cold Spring Harbor Laboratory Press, 2nd ed., 1988); and Hammerling, et al., In *Monoclonal Antibodies and T-Cell Hybridomas*, pp. 563-681 (Elsevier, N.Y., 1981). Examples of phage display methods that can be used to make the anti-CD70 antibodies include, e.g., those disclosed in (Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics in Anti-IgE and Allergic Disease*, Jardieu and Fick Jr., eds., Marcel Dekker, New York, N.Y., Chapter 20, pp. 427-469; Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/01134; PCT Publications WO 90/02809, WO 91/10737, WO 92/01047, WO 92/18619, WO 93/11236, WO 95/15982, WO 95/20401, and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108 (the disclosures of which are incorporated by reference herein).

Examples of techniques that can be used to produce single-chain antibodies include those described in U.S. Pat. Nos. 4,946,778 and 5,258,498; Huston et al., 1991, *Methods in Enzymology* 203:46-88; Shu et al., 1993, *Proc. Natl. Acad. Sci. USA* 90:7995-7999; and Skerra et al., 1988, *Science* 240:1038-1040.

Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-39). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al., 1991, EMBO J. 10:3655-59.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. In some embodiments, the fusion includes a first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In an embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (see, e.g., International Publication No. WO 94/04690, which is incorporated herein by reference in its entirety).

For further discussion of bispecific antibodies see, for example, Suresh et al., 1986, *Methods in Enzymology* 121: 210; Rodrigues et al., 1993, *J. Immunology* 151:6954-61; Carter et al., 1992, *Bio/Technology* 10:163-67; Carter et al., 1995, *J. Hematotherapy* 4:463-70; Merchant et al., 1998, *Nature Biotechnology* 16:677-81. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679 and European Patent Publication No. EPA 0 217 577, both of which are incorporated herein by reference.

An anti-CD70 antibody can also be a humanized antibody. Humanized antibodies are antibody molecules that bind the desired antigen and have one or more CDRs from a non-human species, and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al, 1988, *Nature* 332:323.) Antibodies can be humanized using a variety of techniques known in the art including, for example, CDR-grafting (see, e.g., EP 0 239 400; PCT publication WO 91/09967; U.S. Pat. Nos. 5,225,539; 5,530,101; and 5,585, 089), veneering or resurfacing (see, e.g., EP 0 592 106; EP 0 519 596; Padlan, *Molecular Immunology*, 1991, 28(4/5):489-498; Studnicka et al., 1994, *Protein Engineering* 7(6):805-814; Roguska et al, 1994, *Proc. Natl. Acad. Sci. USA* 91:969-973), and chain shuffling (see, e.g., U.S. Pat. No. 5,565,332) (all of these references are incorporated by reference herein).

Humanized monoclonal antibodies also can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 0 012 023; Berter et al., 1988, *Science* 240:1041-43; Liu et al., 1987, *Proc. Natl. Acad. Sci. USA* 84:3439-43; Liu et al., 1987, *J. Immunol.* 139:3521-26; Sun et al., 1987, *Proc. Natl. Acad. Sci. USA* 84:214-18; Nishimura et al., 1987, *Cancer. Res.* 47:999-1005; Wood et al., 1985, *Nature* 314:446-449; and Shaw et al., 1988, *J. Natl. Cancer Inst.* 80:1553-59; Morrison, 1985, *Science* 229:1202-07; Oi et al., 1986, *BioTechniques* 4:214; U.S. Pat. No. 5,225,539; Jones et al., 1986, *Nature* 321:552-25; Verhoeyan et al., 1988, *Science* 239:1534; and Beidler et al., 1988, *J. Immunol.* 141: 4053-60; each of which is incorporated herein by reference in its entirety.

In some embodiments, the antibody is a humanized 1F6 or 2F2 antibody, as disclosed in U.S. Provisional Patent Application No. 60/673,070, filed Apr. 19, 2005, and PCT International Publication No. WO 2006/113909, the disclosures of which is incorporated by reference herein.

In some embodiments, the anti-CD70 antibody is a human IgG antibody. Human antibodies can be made by a variety of methods known in the art including, e.g., phage display methods (see supra) using antibody libraries derived from human immunoglobulin sequences. See also, e.g., U.S. Pat. Nos. 4,444,887 and 4,716,111; and PCT Publications WO 98/46645, WO 98/50433, WO 98/24893, WO 98/16654, WO 96/34096, WO 96/33735, and WO 91/10741 (the disclosures of which are incorporated by reference herein). In addition, a human antibody recognizing a selected epitope can be generated using a technique referred to as "guided selection," in which a selected non-human monoclonal antibody, e.g., a mouse antibody, is used to guide the selection of a completely human antibody recognizing the same epitope (see, e.g., Jespers et al., 1994, *Bio/technology* 12:899-903). Human antibodies can also be produced using transgenic mice that express human immunoglobulin genes. Monoclonal antibodies directed against the antigen can be obtained from the immunized, transgenic mice using conventional hybridoma technology. For an overview of this technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., PCT Publications WO 98/24893, WO 92/01047, WO 96/34096, and WO 96/33735; European Patent No. 0 598 877; U.S. Pat. Nos. 5,413,923; 5,625,126; 5,633,425; 5,569, 825; 5,661,016; 5,545,806; 5,814,318; 5,885,793; 5,916,771; and 5,939,598 (the disclosures of which are incorporated by reference herein).

In addition, companies such as Abgenix, Inc. (now Amgen; Fremont, Calif.), Genpharm (San Jose, Calif.), and Medarex (Princeton, N.J.) can be engaged to provide human antibodies directed against a selected antigen using technology similar to that described above. Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety.)

As set forth supra, a CD70 binding agent can be a derivative of an anti-CD70 antibody. Generally, an anti-CD70 antibody derivative comprises an anti-CD70 antibody (including e.g., an antigen-binding fragment or conservatively substituted polypeptides) and at least one polypeptide region or other moiety heterologous to the anti-CD70 antibody. For example, an anti-CD70 antibody can be modified, e.g., by the covalent attachment of any type of molecule, such that covalent attachment does not prevent the antibody derivative from specifically binding to CD70 via the antigen-binding region or region derived therefrom, or the effector domains(s) from specifically binding Fc receptor. Typical modifications include, e.g., glycosylation, acetylation, pegylation, phosphorylation, amidation, derivatization by known protecting/blocking groups, proteolytic cleavage, linkage to a cellular ligand or other protein, and the like. Any of numerous chemical modifications may be carried out by known techniques, including, but not limited to specific chemical cleavage, acetylation, formylation, metabolic synthesis in the presence of tunicamycin, etc.

In some embodiments, the antibody derivative is a multimer, such as, for example, a dimer, comprising one or more monomers, where each monomer includes (i) an antigen-binding region of an anti-CD70 antibody, or a polypeptide region derived therefrom (such as, e.g., by conservative substitution of one or more amino acids), and (ii) a multimerizing (e.g., dimerizing) polypeptide region, such that the antibody derivative forms multimers (e.g., homodimers) that specifically bind to CD70. In typical embodiments, an antigen binding region of an anti-CD70 antibody, or a polypeptide region derived therefrom, is recombinantly or chemically fused with a heterologous protein, wherein the heterologous protein comprises a dimerization or multimerization domain. Prior to administration of the antibody derivative to a subject for the purpose of treating or preventing immunological disorders or CD70-expressing cancers, the derivative is subjected to conditions that allow formation of a homodimer or heterodimer. A heterodimer, as used herein, may comprise identical dimerization domains but different CD70 antigen-binding regions, identical CD70 antigen-binding regions but different dimerization domains, or different CD70 antigen-binding regions and dimerization domains.

Typical dimerization domains are those that originate from transcription factors. In one embodiment, the dimerization domain is that of a basic region leucine zipper ("bZIP") (see Vinson et al., 1989, *Science* 246:911-916). Useful leucine zipper domains include, for example, those of the yeast transcription factor GCN4, the mammalian transcription factor CCAAT/enhancer-binding protein C/EBP, and the nuclear transform in oncogene products, Fos and Jun. (See Landschultz et al., 1988, *Science* 240:1759-64; Baxevanis and Vinson, 1993, *Curr. Op. Gen. Devel.* 3:278-285; O'Shea et al., 1989, *Science* 243:538-542.) In another embodiment, the dimerization domain is that of a basic-region helix-loop-helix ("bHLH") protein. (See Murre et al., 1989, *Cell* 56:777-783. See also Davis et al., 1990, *Cell* 60:733-746; Voronova and Baltimore, 1990, *Proc. Natl. Acad. Sci. USA* 87:4722-26.) Particularly useful hHLH proteins are myc, max, and mac.

In yet other embodiments, the dimerization domain is an immunoglobulin constant region such as, for example, a heavy chain constant region or a domain thereof (e.g., a $C_H1$ domain, a $C_H2$ domain, and/or a $C_H3$ domain). (See, e.g., U.S. Pat. Nos. 5,155,027; 5,336,603; 5,359,046; and 5,349,053; EP 0 367 166; WO 96/04388.)

Heterodimers are known to form between Fos and Jun (Bohmann et al, 1987, *Science* 238:1386-1392), among members of the ATF/CREB family (Hai et al., 1989, *Genes Dev.* 3:2083-2090), among members of the C/EBP family (Cao et al., 1991, *Genes Dev.* 5:1538-52; Williams et al., 1991, *Genes Dev.* 5:1553-67; Roman et al., 1990, *Genes Dev.* 4:1404-15), and between members of the ATF/CREB and Fos/Jun families (Hai and Curran, 1991, *Proc. Natl. Acad. Sci. USA* 88:3720-24). Therefore, when a CD70 binding protein is administered to a subject as a heterodimer comprising different dimerization domains, any combination of the foregoing may be used.

In other embodiments, an anti-CD70 antibody derivative is an anti-CD70 antibody conjugated to a second antibody (an "antibody heteroconjugate") (see U.S. Pat. No. 4,676,980). Heteroconjugates useful for practicing the present methods comprise an antibody that binds to CD70 (e.g., an antibody that has the CDRs and/or heavy chains of the monoclonal antibodies 2F2 or 1F6) and an antibody that binds to a surface receptor or receptor complex, such as CD16/FcgRIII, CD64/FcgRI, killer cell activating or inhibitory receptors, or the complement control protein CD59. In a typical embodiment, the binding of the portion of the multispecific antibody to the second cell surface molecule or receptor complex enhances the effector functions of an anti-CD70 antibody.

In some embodiments, the anti-CD70 antibody or derivative thereof competitively inhibits binding of mAb 1F6 or 2F2 to CD70, as determined by any method known in the art for determining competitive binding (such as e.g., the immunoassays described herein). In typical embodiments, the antibody competitively inhibits binding of 1F6 or 2F2 to CD70 by at least 50%, at least 60%, at least 70%, or at least 75%. In other embodiments, the antibody competitively inhibits binding of 1F6 or 2F2 to CD70 by at least 80%, at least 85%, at least 90%, or at least 95%.

Antibodies can be assayed for specific binding to CD70 by any of various known methods. Immunoassays which can be used include, for example, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well-known in the art. (See, e.g., Ausubel et al., eds., *Short Protocols in Molecular Biology* (John Wiley and Sons, Inc., New York, 4th ed. 1999); Harlow and Lane, *Using Antibodies: A Laboratory Manual* (Cold Spring Harbor Laboratory Press, Cold Spring Harbor, N.Y., 1999.)

Further, the binding affinity of an antibody to CD70 and the off-rate of an antibody CD70 interaction can be determined by competitive binding assays. One example of a competitive binding assay is a radioimmunoassay comprising the incubation of labeled CD70 (e.g., $^3H$ or $^{125}I$) with the antibody of interest in the presence of increasing amounts of unlabeled CD70, and the detection of the antibody bound to the labeled CD70. The affinity of the antibody for CD70 and the binding off-rates can then be determined from the data by Scatchard plot analysis. Competition with a second antibody (such as e.g., mAb 1F6 or 2F2) can also be determined using radioimmunoassays. For example, CD70 is incubated with the antibody of interest conjugated to a labeled compound (e.g., $^3H$ or $^{125}I$) in the presence of increasing amounts of an unlabeled second antibody. Alternatively, the binding affinity of an antibody to CD70 and the on- and off-rates of an antibody-CD70 interaction can be determined by surface plasmon resonance.

In some embodiments, the anti-CD70 antibodies or derivatives thereof can be targeted to and accumulate on the membrane of a CD70-expressing cell.

The anti-CD70 antibodies and derivatives thereof that are useful in the present methods can be produced by methods known in the art for the synthesis of proteins, typically, e.g., by recombinant expression techniques. Recombinant expression of an antibody or derivative thereof that binds to CD70 and depletes or inhibits the proliferation of CD70-expressing cells requires construction of an expression vector containing a nucleic acid that encodes the antibody or derivative thereof. A vector for the production of the protein molecule may be produced by recombinant DNA technology using techniques known in the art. Standard techniques such as, for example, those described in Sambrook and Russell, *Molecular Cloning: A Laboratory Manual* (Cold Spring Harbor Laboratory Press, Cold Spring Harbor, N.Y., 3rd ed., 2001); Sambrook et al., *Molecular Cloning: A Laboratory Manual* (Cold Spring Harbor Laboratory Press, Cold Spring Harbor, N.Y., 2nd ed., 1989); *Short Protocols in Molecular Biology* (Ausubel et al., John Wiley and Sons, New York, 4th ed., 1999); and Glick and Pasternak, *Molecular Biotechnology: Principles and Applications of Recombinant DNA* (ASM Press, Washington, D.C., 2nd ed., 1998) can be used for recombinant nucleic acid methods, nucleic acid synthesis, cell culture, transgene incorporation, and recombinant protein expression.

For example, for recombinant expression of an anti-CD70 antibody, an expression vector may encode a heavy or light chain thereof, or a heavy or light chain variable domain, operably linked to a promoter. An expression vector may include, for example, the nucleotide sequence encoding the constant region of the antibody molecule (see, e.g., PCT Publication WO 86/05807; PCT Publication WO 89/01036; and U.S. Pat. No. 5,122,464), and the variable domain of the antibody may be cloned into such a vector for expression of the entire heavy or light chain. The expression vector is transferred to a host cell by conventional techniques, and the transfected cells are then cultured by conventional techniques to produce the anti-CD70 antibody. In typical embodiments for the expression of double-chain antibodies, vectors encoding both the heavy and light chains can be co-expressed in the host cell for expression of the entire immunoglobulin molecule.

A variety of prokaryotic and eukaryotic host-expression vector systems can be utilized to express an anti-CD70 antibody or derivative thereof. Typically, eukaryotic cells, particularly for whole recombinant anti-CD70 antibody molecules, are used for the expression of the recombinant protein. For example, mammalian cells such as Chinese hamster ovary cells (CHO), in conjunction with a vector such as the major intermediate early gene promoter element from human cytomegalovirus, is an effective expression system for the production of anti-CD70 antibodies and derivatives thereof (see, e.g., Foecking et al., 1986, *Gene* 45: 101; Cockett et al., 1990, *Bio/Technology* 8:2).

Other host-expression systems include, for example, plasmid-based expression systems in bacterial cells (see, e.g., Ruther et al., 1983, *EMBO* 1, 2:1791; Inouye and Inouye, 1985, *Nucleic Acids Res.* 13:3101-3109; Van Heeke and Schuster, 1989, *J. Biol. Chem.* 24:5503-5509); insect systems such as, e.g., the use of *Autographa californica* nuclear polyhedrosis virus (AcNPV) expression vector in *Spodoptera frugiperda* cells; and viral-based expression systems in mammalian cells, such as, e.g., adenoviral-based systems (see, e.g., Logan and Shenk, 1984, *Proc. Natl. Acad. Sci. USA* 81:355-359; Bittner et al., 1987, *Methods in Enzymol.* 153:51-544).

In addition, a host cell strain can be chosen that modulates the expression of the inserted sequences, or modifies and processes the gene product in the specific fashion desired. Appropriate cell lines or host systems can be chosen to ensure the correct modification and processing (e.g., glycosylation, phosphorylation, and cleavage) of the protein expressed. To this end, eukaryotic host cells which possess the cellular machinery for proper processing of the primary transcript and gene product can be used. Such mammalian host cells include, for example, CHO, VERO, BHK, HeLa, COS, MDCK, 293, 3T3, and W138.

A stable expression system is typically used for long-term, high-yield production of recombinant anti-CD70 antibody or derivative thereof. For example, cell lines that stably express the anti-CD70 antibody or derivative thereof can be engineered by transformation of host cells with DNA controlled by appropriate expression control elements (e.g., promoter, enhancer, sequences, transcription terminators, polyadenylation sites) and a selectable marker, followed by growth of the transformed cells in a selective media. The selectable marker confers resistance to the selection and allows cells to stably integrate the DNA into their chromosomes and grow to form foci which in turn can be cloned and expanded into cell lines. A number of selection systems can be used, including, for example, the herpes simplex virus thymidine kinase, hypoxanthineguanine phosphoribosyltransferase, and adenine phosphoribosyltransferase genes, which can be employed in tk⁻, hgprt⁻ or aprt⁻ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin. Methods commonly known in the art of recombinant DNA technology can be routinely applied to select the desired recombinant clone, and such methods are described, for example, in *Current Protocols in Molecular Biology* (Ausubel et al. eds., John Wiley and Sons, N.Y., 1993); Kriegler, *Gene Transfer and Expression, A Laboratory Manual* (Stockton Press, N.Y., 1990); *Current Protocols in Human Genetics* (Dracopoli et al. eds., John Wiley and Sons, N.Y., 1994, Chapters 12 and 13); and Colberre-Garapin et al., 1981, *J. Mol. Biol.* 150:1.

The expression levels of an antibody or derivative can be increased by vector amplification. (See generally, e.g., Bebbington and Hentschel, *The Use of Vectors Based on Gene Amplification for the Expression of Cloned Genes in Mammalian Cells in DNA Cloning*, Vol. 3 (Academic Press, New York, 1987).) When a marker in the vector system expressing an anti-CD70 antibody or derivative thereof is amplifiable, an increase in the level of inhibitor present in host cell culture media will select host cells that have increased copy number of a marker gene conferring resistance to the inhibitor. The copy number of an associated antibody gene will also be increased, thereby increasing expression of the antibody or derivative thereof (see Crouse et al., 1983, *Mol. Cell. Biol.* 3:257). Expression levels can also be increased by optimizating the vector, and in particular the nucleic acids encoding the antibody or derivative, for the host organism (e.g., by modifying the codon usage, CpG content, and the like).

Where the anti-CD70 antibody comprises both a heavy and a light chain or derivatives thereof, the host cell may be co-transfected with two expression vectors, the first vector encoding the heavy chain protein and the second vector encoding the light chain protein. The two vectors may contain identical selectable markers which enable equal expression of heavy and light chain proteins. Alternatively, a single vector may be used which encodes, and is capable of expressing, both heavy and light chain proteins. In such situations, the light chain is typically placed before the heavy chain to avoid an excess of toxic free heavy chain (see Proudfoot, 1986, Nature 322:52; Kohler, 1980, Proc. Natl. Acad. Sci. USA 77:2197). The coding sequences for the heavy and light chains may comprise cDNA or genomic DNA.

Once an anti-CD70 antibody or derivative thereof has been produced (e.g., by an animal, chemical synthesis, or recombinant expression), it can be purified by any suitable method for purification of proteins, including, for example, by chromatography (e.g., ion exchange or affinity chromatography (such as, for example, Protein A chromatography for purification of antibodies having an intact Fc region)), centrifugation, differential solubility, or by any other standard technique for the purification of proteins. An anti-CD70 antibody or derivative thereof can, for example, be fused to a marker sequence, such as a peptide, to facilitate purification by affinity chromatography. Suitable marker amino acid sequences include, e.g., a hexa-histidine peptide, such as the tag provided in a pQE vector (QIAGEN, Inc., Chatsworth, Calif., 91311), and the "HA" tag, which corresponds to an epitope derived from the influenza hemagglutinin protein (Wilson et al., 1984, Cell 37:767), and the "flag" tag.

Once an anti-CD70 antibody or derivative thereof is produced, its ability to exert a cytostatic or cytotoxic effect on CD70-expressing cancer cells or an immunomodulatory effect on a CD70-expressing immune cell is determined by the methods described infra or as known in the art.

To minimize activity of the anti-CD70 antibody outside the activated immune cells or CD70-expressing cancer cells, an antibody that specifically binds to cell membrane-bound CD70, but not to soluble CD70, can be used, so that the anti-CD70 antibody is concentrated at the cell surface of the activated immune cell or CD70-expressing cancer cell.

Typically, the anti-CD70 antibody or derivative is substantially purified (e.g., substantially free from substances that limit its effect or produce undesired side-effects). In some embodiments, the anti-CD70 antibody or derivative is at least about 40% pure, at least about 50% pure, or at least about 60% pure. In some embodiments, the anti-CD70 antibody or derivative is at least about 60-65%, 65-70%, 70-75%, 75-80%, 80-85%, 85-90%, 90-95%, or 95-98% pure. In some embodiments, the anti-CD70 antibody or derivative is approximately 99% pure.

III. Other CD70 Binding Agents

Further CD70 binding agents include fusion proteins (i.e., proteins that are recombinantly fused or chemically conjugated, including both covalent and non-covalent conjugation) to heterologous proteins (of typically at least 10, 20, 30, 40, 50, 60, 70, 80, 90 or at least 100 amino acids). Such CD70 binding agents include a portion that binds to CD70 and an immunoglobulin effector domain or a functional equivalent thereof. As used herein, a functional equivalent of immunoglobulin effector domain binds to an Fc receptor on an immune cell with phagocytic or lytic activity or by binding of an Fc effector domain(s) to components of the complement system. The fusion protein does not necessarily need to be direct, but may occur through linker sequences.

For example, a CD70 binding agent can be produced recombinantly by fusing the coding region of one or more of the CDRs of an anti-CD70 antibody in frame with a sequence coding for a heterologous protein. The heterologous protein includes an effector domain or a functional equivalent thereof and may provide one or more of the following characteristics: promote stable expression; provide a means of facilitating high yield recombinant expression; and/or provide a multimerization domain.

In some embodiments, the CD70 binding agent can include one or more CDRs from an antibody that binds to CD70 and depletes or inhibits the proliferation of CD70-expressing cells alone, without conjugation to a cytotoxic agent.

In an aspect, a CD70 binding agent can include CD27 and variants or fragments thereof that bind to CD70. CD70 binding agent can further include peptides, ligands and other molecules that specifically bind to CD70.

A CD70 binding agent can be identified using any method suitable for screening for protein-protein interactions. Typically, proteins are initially identified by their ability to specifically bind to CD70. The ability of such a binding protein to exert a cytostatic or cytotoxic effect on activated lymphocytes or CD70-expressing cancer cells by recruiting and activating cytotoxic white blood cells, e.g., natural killer (NK) cells, phagocytotic cells, e.g., macrophages, and serum complement components, without conjugation to a cytotoxic or cytostatic agent, or an immunomodulatory effect on an immune cell by themselves, without conjugation to an immunomodulatory agent, can be determined. Among the traditional methods which can be employed are "interaction cloning" techniques which entail probing expression libraries with labeled CD70 in a manner similar to the technique of antibody probing of λgt11 libraries. By way of example and not limitation, this can be achieved as follows: a cDNA clone encoding CD70 (or a 1F6 or 2F2 binding domain thereof) can be modified at the C-terminus by inserting the phosphorylation site for the heart muscle kinase (HMK) (see, e.g., Blanar and Rutter, 1992, Science 256:1014-18). The recombinant protein is expressed in E. coli and purified on a GDP-affinity column to homogeneity (Edery et al., 1988, Gene 74:517-25) and labeled using $\gamma^{32}$P-ATP and bovine heart muscle kinase (Sigma) to a specific activity of $1 \times 10^8$ cpm/μg, and used to screen a human placenta λgt11 cDNA library in a "far-Western assay" (Blanar and Rutter, 1992, Science 256:1014-18). Plaques which interact with the CD70 probe are isolated. The cDNA inserts of positive λ plaques are released and subcloned into a vector suitable for sequencing, such as pBluescript KS (Stratagene, La Jolla, Calif.).

One method which detects protein interactions in vivo is the two-hybrid system. One version of this system has been described (Chien et al., 1991, Proc. Natl. Acad. Sci. USA 88:9578-82) and is commercially available from Clontech (Palo Alto, Calif.).

Once a CD70 binding protein is identified, its ability (alone or when multimerized or fused to a dimerization or multimerization domain) to exert a cytostatic or cytotoxic effect on CD70-expressing cancer cells or an immunomodulatory effect on a CD70-expressing immune cell can be determined by the methods described infra.

IV. Methods to Improve Effector Functions of Anti-CD70 Targeting Agents

In some embodiments, the effector function of a CD70 binding agent can be augmented by improving its effector functions using one or more antibody engineering approaches known in the art. Illustrative, non-limiting examples for such approaches are provided below.

ADCC and ADCP are mediated through the interaction of cell-bound antibodies with Fcγreceptors (FcγR) expressed on effector cells. Both the glycosylation status and primary amino acid sequence of the IgG Fc region have functional effects on the Fcγ-FcγR interaction. A stronger Fcγ-FcγR interaction is associated with better target cell killing by effector cells.

Oligosaccharides covalently attached to the conserved Asn297 are required for the Fc region of an IgG to bind FcγR (Lund et al, 1996, *J. Immunol.* 157:4963-69; Wright and Morrison, 1997, *Trends Biotechnol.* 15:26-31). Engineering of this glycoform on IgG can significantly improve IgG-mediated ADCC. Addition of bisecting N-acetylglucosamine modifications (Umana et al., 1999, *Nat. Biotechnol.* 17:176-180; Davies et al., 2001, *Biotech. Bioeng.* 74:288-94) to this glycoform or removal of fucose (Shields et al., 2002, *J. Biol. Chem.* 277:26733-40; Shinkawa et al., 2003, *J. Biol. Chem.* 278:6591-604; Niwa et al., 2004, *Cancer Res.* 64:2127-33) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., 2001, *J. Biol. Chem.* 276:6591-604). When compared to parental IgG1, a subset of these variants involving substitutions at Thr256/Ser298, Ser298/Glu333, Ser298/Lys334, or Ser298/Glu333/Lys334 to Ala demonstrate increased in both binding affinity toward FcγR and ADCC activity (Shields et al., 2001, *J. Biol. Chem.* 276:6591-604; Okazaki et al., 2004, *J. Mol. Biol.* 336:1239-49).

Antibody-mediated CDC begins with the binding of C1q to cell bound IgG molecules. Specific amino acid residues on human IgG1 responsible for C1q binding and species-specific differences of C1q binding have been reported (Idusogie et al., 2000, *J. Immunol.* 164:4178-4184). Complement fixation activity of antibodies have been improved by substitutions at Lys326 and Glu333; for e.g., such substitutions can improve both C1q binding and CDC activity of the human IgG 1 antibody rituximab (Idusogie et al., 2001, *J. Immunol.* 166: 2571-2575). The same substitutions on a human IgG2 backbone can convert an antibody isotype that binds poorly to C1q and is severely deficient in complement activation activity to one that can both bind C1q and mediate CDC (Idusogie et al., 2001, *J. Immunol.* 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., 1995, *J. Immunol.* 154:2226-36). Also, substituting Ser444 located close to the carboxy-terminal of IgG1 heavy chain with Cys induced tail-to-tail dimerization of IgG1 with a 200-fold increase of CDC activity over monomeric IgG1 (Shopes et al., 1992, *J. Immunol.* 148:2918-22). In addition, a bispecific diabody construct with specificity for C1q also confers CDC activity (Kontermann et al., 1997, *Nat. Biotech.* 15:629-31).

The in vivo half-life of an antibody can also impact on its effector functions. In some embodiments, it is desirable to increase or decrease the half-life of an antibody to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, *Annu. Rev. Immunol.* 18:739-766; Ghetie and Ward, 2002, *Immunol. Res.* 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, *Ann. Rev. Immunol.* 18:739-766; Ghetie and Ward, 2002, *Immunol. Res.* 25:97-113). The region on human IgG1 involved in FcRn binding has been mapped (Shields et al., 2001, *J. Biol. Chem.* 276:6591-604). Alanine substitutions at positions Pro238, Thr256, Thr307, Gln311, Asp312, Glu380, Glu382, or Asn434 of human IgG1 enhance FcRn binding (Shields et al., 2001, *J. Biol. Chem.* 276:6591-604). IgG1 molecules harboring these substitutions are expected to have longer serum half-lives. Consequently, these modified IgG1 molecules may be able to carry out their effector functions, and hence exert their therapeutic efficacies, over a longer period of time compared to unmodified IgG1.

V. Assays for Cytotoxic, Cytostatic, and Immunomodulatory Activities

Methods of determining whether an antibody mediates effector function against a target cell are known. Illustrative examples of such methods are described infra.

For determining whether an anti-CD70 antibody or derivative mediates antibody-dependent cellular cytotoxicity against activated immune cells or CD70-expressing cancer cells, an assay that measures target cell death in the presence of antibody and effector immune cells may be used. An assay used to measure this type of cytotoxicity can be based on determination of $^{51}$Cr release from metabolically-labeled targets cells after incubation in the presence of effector cells and target-specific antibody (see, e.g., Perussia and Loza, 2000, *Methods in Molecular Biology* 121:179-92 and "$^{51}$Cr Release Assay of Antibody-Dependent Cell-Mediated Cytotoxicity (ADCC)," in *Current Protocols in Immunology*, Coligan et al. eds., Wiley and Sons, 1993). For example, activated immune cells (e.g., activated lymphocytes) or CD70-expressing cancer cells labeled with Na$_2$$^{51}$CrO$_4$ and plated at a density of 5,000 cells per well of a 96-well plate can be treated with varying concentrations of anti-CD70 antibody for 30 minutes and then mixed with normal human peripheral blood mononuclear cells (PBMC) for 4 hours. The membrane disruption that accompanies target cell death releases $^{51}$Cr into the culture supernatant which may be collected and assessed for radioactivity as a measure of cytotoxic activity. Other assays to measure ADCC may involve nonradioactive labels or be based on induced release of specific enzymes. For example, a non-radioactive assay based on time-resolved fluorometry is commercially available (Delphia, Perkin Elmer). This assay is based on loading target cells with an acetoxymethyl ester of fluorescence enhancing ligand (BATDA) that penetrates the cell membrane then hydrolyses to form a membrane impermeable hydrophilic ligand (TDA). When mixed with target specific antibody and PBMC effector cells, TDA is released from lysed cells and is available to form a highly fluorescent chelate when mixed with Europium. The signal, measured with a time-resolved fluorometer, correlates with the amount of cell lysis.

To determine whether an anti-CD70 antibody or derivative mediates antibody-dependent cellular phagocytosis against activated immune cells or CD70-expressing cancer cells, an assay that measures target cell internalization by effector immune cells (e.g., fresh cultured macrophages or established macrophage-like cell line) may be used (see, e.g., Munn and Cheung, 1990, *J. Exp. Med.* 172:231-37; Keler et al., 2000, *J. Immunol.* 164:5746-52; Akewanlop et al., 2001, *Cancer Res.* 61:4061-65). For example, target cells may be labeled with a lipophilic membrane dye such as PKH67 (Sigma), coated with target-specific antibody, and mixed with effector immune cells for 4-24 hours. The effector cells may then be identified by counterstaining with a fluorochrome-labeled antibody specific for a phagocytic cell surface marker (e.g., CD14) and the cells analyzed by two-color flow cytometry or fluoresence microscopy. Dual-positive cells represent effector cells that have internalized target cells. For these assays, effector cells may be monocytes derived from PBMC that have been differentiated into macrophages by culture for 5-10 days with M-CSF or GM-CSF (see, e.g., Munn and Cheung, supra). Human macrophage-like cell lines U937 (Larrick et al., 1980, *J. Immunology* 125:6-12) or THP-1 (Tsuchiya et al., 1980, *Int. J. Cancer* 26:171-76) which are available from ATCC may be used as an alternative phagocytic cell source.

Methods of determining whether an antibody mediates complement-dependent cytotoxicity upon binding to target cells are also known. The same methods can be applied to determine whether a CD70 binding agent mediates CDC activated immune cells or CD70-expressing cancer cells. Illustrative examples of such methods are described infra.

The source of active complement can either be normal human serum or purified from laboratory animal including rabbits. In a standard assay, a CD70 binding agent is incubated with CD70-expressing activated immune cells (e.g., activated lymphocytes) or CD70-expressing cancer cells in the presence of complement. The ability of such CD70 binding agent to mediate cell lysis can be determined by several readouts. In one example, a $Na^{51}CrO_4$ release assay is used. In this assay, target cells are labeled with $Na^{51}CrO_4$. Unincorporated $Na^{51}CrO_4$ is washed off and cells are plated at a suitable density, typically between 5,000 to 50,000 cells/well, in a 96-well plate. Incubation with the CD70 binding agent in the presence of normal serum or purified complement typically last for 2-6 hours at 37° C. in a 5% $CO_2$ atmosphere. Released radioactivity, indicating cell lysis, is determined in an aliquot of the culture supernatant by gamma ray counting. Maximum cell lysis is determined by releasing incorporated $Na^{51}CrO_4$ by detergent (0.5-1% NP-40 or Triton X-100) treatment. Spontaneous background cell lysis is determined in wells where only complement is present without any CD70 binding agents. Percentage cell lysis is calculated as (CD70 binding agent-induced lysis-spontaneous lysis)/maximum cell lysis. The second readout is a reduction of metabolic dyes, e.g., Alamar Blue, by viable cells. In this assay, target cells are incubated with CD70 binding agent and with complement and incubated as described above. At the end of incubation, 1/10 volume of Alamar Blue (Biosource International, Camarillo, Calif.) is added. Incubation is continued for up to 16 hours at 37° C. in a 5% $CO_2$ atmosphere. Reduction of Alamar Blue as an indication of metabolically active viable cells is determined by fluorometric analysis with excitation at 530 nm and emission at 590 nm. The third readout is cellular membrane permeability to propidium iodide (PI). Formation of pores in the plasma membrane as a result of complement activation facilitates entry of PI into cells where it will diffuse into the nuclei and bind DNA. Upon binding to DNA, PI fluorescence in the 600 nm significantly increases. Treatment of target cells with CD70 binding agent and complement is carried out as described above. At end of incubation, PI is added to a final concentration of 5 µg/ml. The cell suspension is then examined by flow cytometry using a 488 nm argon laser for excitation. Lysed cells are detected by fluorescence emission at 600 nm.

VI. Animal Models of Immunological Disorders or CD70-Expressing Cancers

The anti-CD70 antibodies or derivatives can be tested or validated in animal models of immunological disorders or CD70-expressing cancers. A number of established animal models of immunological disorders or CD70-expressing cancers are known to the skilled artisan, any of which can be used to assay the efficacy of the anti-CD70 antibody or derivative. Non-limiting examples of such models are described infra.

Examples for animal models of systemic and organ-specific autoimmune diseases including diabetes, lupus, systemic sclerosis, Sjögren's Syndrome, experimental autoimmune encephalomyelitis (multiple sclerosis), thyroiditis, myasthenia gravis, arthritis, uveitis, inflammatory bowel disease have been described by Bigazzi, "Animal Models of Autoimmunity: Spontaneous and Induced," in *The Autoimmune Diseases* (Rose and Mackay eds., Academic Press, 1998); in "Animal Models for Autoimmune and Inflammatory Disease," in *Current Protocols in Immunology* (Coligan et al. eds., Wiley and Sons, 1997); and Peng, "Experimental Use of Murine Lupus Models," in *Methods in Molecular Medicine*, Vol. 102. *Autoimmunity: Methods and Protocols* (Perl ed., Humana Press Inc.).

Allergic conditions, e.g., asthma and dermatitis, can also be modeled in rodents. Airway hypersensitivity can be induced in mice by ovalbumin (Tomkinson et al, 2001, *J. Immunol.* 166:5792-800) or *Schistosoma mansoni* egg antigen (Tesciuba et al., 2001, *J. Immunol.* 167:1996-2003). The Nc/Nga strain of mice show marked increase in serum IgE and spontaneously develop atopic dermatitis-like leisons (Vestergaard et al., 2000, *Mol. Med. Today* 6:209-10; Watanabe et al., 1997, *Int. Immunol.* 9:461-66; Saskawa et al, 2001, *Int. Arch. Allergy Immunol.* 126:239-47).

Injection of immuno-competent donor lymphocytes into a lethally irradiated histo-incompatible host is a classical approach to induce GVHD in mice. Alternatively, the parent B6D2F1 murine model provides a system to induce both acute and chronic GVHD. In this model the B6D2F1 mice are F1 progeny from a cross between the parental strains of C57BL/6 and DBA/2 mice. Transfer of DBA/2 lymphoid cells into non-irradiated B6D2F1 mice causes chronic GVHD, whereas transfer of C57BL/6, C57BL/10 or B10.D2 lymphoid cells causes acute GVHD (Slayback et al., 2000, *Bone Marrow Transpl.* 26:931-938; Kataoka et al., 2001, *Immunology* 103:310-318).

Additionally, both human hematopoietic stem cells and mature peripheral blood lymphoid cells can be engrafted into SCID mice, and these human lympho-hematopoietic cells remain functional in the SCID mice (McCune et al., 1988, *Science* 241:1632-1639; Kamel-Reid and Dick, 1988, *Science* 242:1706-1709; Mosier et al., 1988, *Nature* 335:256-259). This has provided a small animal model system for the direct testing of potential therapeutic agents on human lymphoid cells. (See, e.g., Tournoy et al, 2001, *J. Immunol.* 166: 6982-6991.)

Moreover, small animal models to examine the in vivo efficacies of the anti-CD70 antibodies or derivatives can be created by implanting CD70-expressing human tumor cell lines into appropriate immunodeficient rodent strains, e.g., athymic nude mice or SCID mice. Examples of CD70-expressing human lymphoma cell lines include, for example, Daudi (Ghetie et al., 1994, *Blood* 83:1329-36; Ghetie et al., 1990, *Int. J. Cancer* 15:481-85; de Mont et al., 2001, *Cancer Res.* 61:7654-59), HS-Sultan (Cattan and Maung, 1996, *Cancer Chemother. Pharmacol.* 38:548-52; Cattan and Douglas, 1994, *Leuk. Res.* 18:513-22), and Raji (Ochakovskaya et al., 2001, *Clin. Cancer Res.* 7:1505-10; Breisto et al., 1999, *Cancer Res.* 59:2944-49). A non-limiting example of a CD70-expressing Hodgkin's lymphoma line is L428 (Drexler, H. G., 1993, *Leuk. Lymphoma* 9:1-25; Dewan et al., 2005, *Cancer Sci.* 96:466-473). Non-limiting examples of CD70 expressing human renal cell carcinoma cell lines include 786-O (Ananth et al., 1999, *Cancer Res.* 59:2210-16; Datta et al., 2001, *Cancer Res.* 61:1768-75), ACHN (Hara et al., 2001, *J. Urol.* 166:2491-94; Miyake et al., 2002, *J. Urol.* 167:2203-08), Caki-1 (Prewett et al., 1998, *Clin. Cancer Res.* 4:2957-66; Shi and Siemann, 2002, *Br. J. Cancer* 87:119-26), and Caki-2 (Zellweger et al., 2001, *Neoplasia* 3:360-67). Non-limiting examples of CD70-expressing nasopharyngeal carcinoma cell lines include C15 and C17 (Busson et al., 1988, *Int. J. Cancer* 42:599-606; Bernheim et al., 1993, *Cancer Genet. Cytogenet.* 66:11-5). Non-limiting examples of CD70-expressing human glioma cell lines include U373 (Palma et al., 2000, *Br. J. Cancer* 82:480-7) and U87MG (Johns et al., 2002, *Int. J. Cancer* 98:398-408). Non-limiting examples of multiple myeloma cell lines include MM.1S (Greenstein et al, 2003, *Experimental Hematology* 31:271-282) and L363 (Diehl et al., 1978, Blut 36:331-338). (See also Drexler and Matsuo, 2000, *Leukemia Research* 24:681-703). These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-CD70 antibody or derivatives as described herein on modulating in vivo tumor growth.

VII. Immune Disorders and CD70-Expressing Cancers

The anti-CD70 antibodies or derivatives as described herein are useful for treating or preventing a CD70-expressing cancer or an immunological disorder characterized by expression of CD70 by inappropriate activation of immune cells (e.g., lymphocytes or dendritic cells). Such expression of CD70 can be due to, for example, increased CD70 protein levels on the cells surface and/or altered antigenicity of the expressed CD70. Treatment or prevention of the immunological disorder, according to the methods described herein, is achieved by administering to a subject in need of such treatment or prevention an effective amount of the anti-CD70 antibody or derivative, whereby the antibody or derivative (i) binds to activated immune cells that express CD70 and that are associated with the disease state and (ii) exerts a cytotoxic, cytostatic, or immunomodulatory effect on the activated immune cells without conjugation to a cytotoxic, cytostatic, or immunomodulatory agent.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., *Fundamental Immunology* (William E. Paul ed., Raven Press, N.Y., 3rd ed. 1993).)

Specific examples of such immunological diseases include the following; rheumatoid arthritis, autoimmune demyelinative diseases (e.g., multiple sclerosis, allergic encephalomyelitis), psoriatic arthritis, endocrine opthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

Accordingly, the methods described herein encompass treatment of disorders of B lymphocytes (e.g., systemic lupus erythematosus, Goodpasture's syndrome, rheumatoid arthritis, and type I diabetes), $Th_1$-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or $Th_2$-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of $Th_1$-lymphocytes or $Th_2$-lymphocytes.

In some embodiments, the immunological disorder is a T cell-mediated immunological disorder, such as a T cell disorder in which activated T cells associated with the disorder express CD70. Anti-CD70 antibodies or derivatives can be administered to deplete such CD70-expressing activated T cells. In a specific embodiment, administration of anti-CD70 antibodies or derivatives can deplete CD70-expressing activated T cells, while resting T cells are not substantially depleted by the anti-CD70 or derivative. In this context, "not substantially depleted" means that less than about 60%, or less than about 70% or less than about 80% of resting T cells are not depleted.

The anti-CD70 antibodies and derivatives as described herein are also useful for treating or preventing a CD70-expressing cancer. Treatment or prevention of a CD70-expressing cancer, according to the methods described herein, is achieved by administering to a subject in need of such treatment or prevention an effective amount of the anti-CD70 antibody or derivative, whereby the antibody or derivative (i) binds to CD70-expressing cancer cells and (ii) exerts a cytotoxic or cytostatic effect to deplete or inhibit the proliferation of the CD70-expressing cancer cells alone (i.e., without conjugation to a cytotoxic, cytostatic, or immunomodulatory agent).

CD70-expressing cancers that can be treated or prevented by the methods described herein include, for example, different subtypes of Non-Hodgkin's Lymphoma (indolent NHLs, follicular NHLs, small lymphocytic lymphomas, lymphoplasmacytic NHLs, or marginal zone NHLs); Hodgkin's disease (e.g., Reed-Sternberg cells); cancers of the B-cell lineage, including, e.g., diffuse large B-cell lymphomas, follicular lymphomas, Burkitt's lymphoma, mantle cell lymphomas, B-cell lymphocytic leukemias (e.g., acute lymphocytic leukemia, chronic lymphocytic leukemia); Epstein Barr Virus positive B cell lymphomas; renal cell carcinomas (e.g., clear cell and papillary); nasopharyngeal carcinomas; thymic carcinomas; gliomas; glioblastomas; neuroblastomas; astrocytomas; meningiomas; Waldenstrom macroglobulinemia; multiple myelomas; and colon, stomach, and rectal carcinomas. The cancer can be, for example, newly diagnosed, pretreated or refractory or relapsed. In some embodiments, a CD70-expressing cancer has at least about 15,000, at least about 10,000 or at least about 5,000 CD70 molecules/cell.

VIII. Pharmaceutical Compositions Comprising Anti-CD70 Antibodies and Derivatives and Administration Thereof A composition containing a CD70 binding agent (e.g., an anti-CD70 antibody or derivative) can be administered to a subject having or at risk of having an immunological disorder or a CD70-expressing cancer. The invention further provides for the use of a CD70 binding agent (e.g., an anti-CD70 antibody or derivative) in the manufacture of a medicament for prevention or treatment of a CD70 expressing cancer or immunological disorder. The term "subject" as used herein means any mammalian patient to which a CD70 binding agent can be administered, including, e.g., humans and non-human mammals, such as primates, rodents, and dogs. Subjects specifically intended for treatment using the methods described herein include humans. The antibodies or derivatives can be administered either alone or in combination with other compositions in the prevention or treatment of the immunological disorder or CD70-expressing cancer.

Various delivery systems are known and can be used to administer the CD70 binding agent. Methods of introduction include but are not limited to intradermal, intramuscular, intraperitoneal, intravenous, subcutaneous, intranasal, epidural, and oral routes. The CD70 binding agent can be administered, for example by infusion or bolus injection, by absorption through epithelial or mucocutaneous linings (e.g., oral mucosa, rectal and intestinal mucosa, and the like) and can be administered together with other biologically active agents such as chemotherapeutic agents. Administration can be systemic or local.

In specific embodiments, the CD70 binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-CD70 antibody or derivative does not absorb are used.

In other embodiments, the anti-CD70 antibody or derivative is delivered in a controlled release system. In one embodiment, a pump may be used (see Langer, 1990, *Science* 249: 1527-1533; Sefton, 1989, *CRC Crit. Ref. Biomed. Eng.* 14:201; Buchwald et al., 1980, *Surgery* 88:507; Saudek et al., 1989, *N. Engl. J. Med.* 321:574). In another embodiment, polymeric materials can be used. (See *Medical Applications of Controlled Release* (Langer and Wise eds., CRC Press, Boca Raton, Fla., 1974); *Controlled Drug Bioavailability, Drug Product Design and Performance* (Smolen and Ball eds., Wiley, New York, 1984); Ranger and Peppas, 1983, *Macromol. Sci. Rev. Macromol. Chem.* 23:61. See also Levy et al., 1985, *Science* 228:190; During et al., 1989, *Ann. Neurol.* 25:351; Howard et al., 1989, *J. Neurosurg.* 71:105.) Other controlled release systems are discussed, for example, in Langer, supra.

A CD70 binding agent (e.g., an anti-CD70 antibody or derivative) can be administered as pharmaceutical compositions comprising a therapeutically effective amount of the binding agent and one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the protein, typically in purified form, together with a suitable amount of carrier so as to provide the form for proper administration to the patient. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a buffering agent (e.g., a phosphate, citrate or amino acid, such as histidine), a solubilizing agent (e.g., nonionic detergents such as a polysorbate, triton, or polyoxamer; or an amino acid) and/or a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a CD70 binding agent (e.g., an anti-CD70 antibody or derivative) in lyophilized form and (b) a second container containing a pharmaceutically acceptable diluent (e.g., sterile water) for injection. The pharmaceutically acceptable diluent can be used for reconstitution or dilution of the lyophilized anti-CD70 antibody or derivative. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the CD70 binding agent (e.g., anti-CD70 antibody or derivative) that is effective in the treatment or prevention of an immunological disorder or CD70-expressing cancer can be determined by standard clinical techniques. In addition, in vitro assays may optionally be employed to help identify optimal dosage ranges. The precise dose to be employed in the formulation will also depend on the route of administration, and the stage of immunological disorder or CD70-expressing cancer, and should be decided according to the judgment of the practitioner and each patient's circumstances. Effective doses may be extrapolated from dose-response curves derived from in vitro or animal model test systems.

For example, toxicity and therapeutic efficacy of the anti-CD70 antibody or derivative can be determined in cell cultures or experimental animals by standard pharmaceutical procedures for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A CD70 binding agent (e.g., an anti-CD70 antibody or derivative) that exhibits a large therapeutic index is preferred. Where a CD70 binding agent exhibits toxic side effects, a delivery system that targets the CD70 binding agent to the site of affected tissue can be used to minimize potential damage non-CD70-expressing cells and, thereby, reduce side effects.

The data obtained from the cell culture assays and animal studies can be used in formulating a range of dosage for use in humans. The dosage of the CD70 binding agent typically lies within a range of circulating concentrations that include the $ED_{50}$ with little or no toxicity. The dosage may vary within this range depending upon the dosage form employed and the route of administration utilized. For any CD70 binding agent used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Generally, the dosage of an anti-CD70 antibody or derivative administered to a patient with an immunological disorder or CD70-expressing cancer is typically 0.1 mg/kg to 100 mg/kg of the subject's body weight. The dosage administered to a subject is 0.1 mg/kg to 50 mg/kg of the subject's body weight, 0.1 to 20 mg/mg, 0.5 mg/kg to 30 mg/kg, 1 mg/kg to 20 mg/kg, 1 mg/kg to 15 mg/kg, or 1 mg/kg to 10 mg/kg of the subject's body weight. Generally, human antibodies have a longer half-life within the human body than antibodies from other species due to the immune response to the foreign proteins. Thus, lower dosages of anti-CD70 antibody or derivative comprising humanized, chimeric or human antibodies and less frequent administration is often possible.

In some embodiments, the pharmaceutical compositions comprising the CD70 binding agent can further comprise a therapeutic agent (i.e., a non-conjugated cytotoxic or immunomodulatory agent such as, for example, any of those described herein). The anti-CD70 binding agent also can be co-administered in combination with one or more therapeutic agents for the treatment or prevention of immunological disorders or CD70-expressing cancers. For example, combination therapy can include a therapeutic agent (e.g., a cytostatic, cytotoxic, or immunomodulatory agent, such as an unconjugated cytostatic, cytotoxic, or immunomodulatory agent such as those conventionally used for the treatment of cancers or immunological disorders). Combination therapy can also include, e.g., administration of an agent that targets a receptor or receptor complex other than CD70 on the surface of activated lymphocytes, dendritic cells or CD70-expressing cancer cells. An example of such an agent includes a second, non-CD70 antibody that binds to a molecule at the surface of an activated lymphocyte, dendritic cell or CD70-expressing cancer cell. Another example includes a ligand that targets such a receptor or receptor complex. Typically, such an antibody or ligand binds to a cell surface receptor on activated lymphocytes, dendritic cell or CD70-expressing cancer cell and enhances the cytotoxic or cytostatic effect of the anti-CD70 antibody by delivering a cytostatic or cytotoxic signal to the activated lymphocyte, dendritic cell or CD70-expressing cancer cell. Such combinatorial administration can have an additive or synergistic effect on disease parameters (e.g., severity of a symptom, the number of symptoms, or frequency of relapse).

With respect to therapeutic regimens for combinatorial administration, in a specific embodiment, an anti-CD70 binding agent is administered concurrently with a therapeutic agent. In another specific embodiment, the therapeutic agent is administered prior or subsequent to administration of the anti-CD70 antibody or derivative, by at least an hour and up to several months, for example at least an hour, five hours, 12 hours, a day, a week, a month, or three months, prior or subsequent to administration of the anti-CD70 antibody or derivative. In some embodiments, the subject is monitored following administration of the anti-CD70 binding agent, and optionally the therapeutic agent.

The therapeutic agent can be, for example, any agent that exerts a therapeutic effect on cancer cells or activated immune cells. Typically, the therapeutic agent is a cytotoxic or immunomodulatory agent. Such combinatorial administration can have an additive or synergistic effect on disease parameters (e.g., severity of a symptom, the number of symptoms, or frequency of relapse).

Useful classes of cytotoxic or immunomodulatory agents include, for example, antitubulin agents, auristatins, DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic or immunomodulatory agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, rapamycin (Sirolimus), streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the cytotoxic agent is a conventional chemotherapeutic such as, for example, doxorubicin, paclitaxel, melphalan, vinca alkaloids, methotrexate, mitomycin C or etoposide. In some embodiments, the therapeutic agent can be a combined therapy, such as CHOP (Cyclophosphamide, Doxorubicin, Prednisolone and Vincristine), CHOP-R (Cyclophosphamide, Doxorubicin Vincristine, Prednisolone, and rituximab) or ABVD (Doxorubicin, Bleomycin, Vinblastine and Dacarbazine). Agents such as CC-1065 analogues, calicheamicin, maytansine, analogues of dolastatin 10, rhizoxin, and palytoxin can also be used.

In specific embodiments, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin E and its derivatives are described in U.S. Patent Application Nos. 20030083263 and 20050009751), International Patent Application No. PCT/US03/24209, International Patent Application No. PCT/US02/13435, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In specific embodiments, the cytotoxic agent is a DNA minor groove binding agent. (See, e.g., U.S. Pat. No. 6,130,237.) For example, in some embodiments, the minor groove binding agent is a CBI compound. In other embodiments, the minor groove binding agent is an enediyne (e.g., calicheamicin).

Examples of anti-tubulin agents include, but are not limited to, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other anti-tubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In some embodiments, the cytotoxic agent is a maytansinoid, another group of anti-tubulin agents. For example, in specific embodiments, the maytansinoid is maytansine or DM-1 (ImmunoGen, Inc.; see also Chari et al., 1992, *Cancer Res.* 52:127-131).

In some embodiments, the therapeutic agent is not a radioisotope. In some embodiments, the therapeutic agent is not ricin or saporin.

In certain embodiments, the therapeutic agent is an anti-VEGF agent, such as AVASTIN (bevacizumab) or NEXAVAR (Sorafenib); a PDGF blocker, such as SUTENT (sunitinib malate); or a kinase inhibitor, such as NEXAVAR (sorafenib tosylateor).

In some embodiments, the cytotoxic or immunomodulatory agent is an antimetabolite. The antimetabolite can be, for example, a purine antagonist (e.g. azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxic or immunomodulatory agent is tacrolimus, cyclosporine or rapamycin. In further embodiments, the cytoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine and zoledronate.

In additional embodiments, the therapeutic agent is an antibody, such as a humanized anti HER2 monoclonal antibody, RITUXAN (rituximab; Genentech; a chimeric anti CD20 monoclonal antibody); OVAREX (AltaRex Corporation, MA); PANOREX (Glaxo Wellcome, N.C.; a murine IgG2a antibody); Cetuximab ERBITUX (Imclone Systems Inc., NY; an anti-EGFR IgG chimeric antibody); Vitaxin (MedImmune, Inc., MD; Campath I/H (Leukosite, Mass.; a humanized IgG1 antibody); lintuzumab (Protein Design Labs, Inc., CA and Seattle Genetics, Inc.; a humanized anti-CD33 IgG antibody); LymphoCide™ (Immunomedics, Inc., NJ; a humanized anti-CD22 IgG antibody); Smart ID 10 (Protein Design Labs, Inc., CA; a humanized anti-HLA-DR antibody); Oncolym™ (Techniclone, Inc., CA; a radiolabeled murine anti-HLA-Dr10 antibody); Allomune™ (BioTransplant, Calif.; a humanized anti-CD2 mAb); Avastin™ (Genentech, Inc., CA; an anti-VEGF humanized antibody); Epratuzamab (Immunomedics, Inc., NJ and Amgen, Calif.; an anti-CD22 antibody); CEAcide™ (Immunomedics, N.J.; a humanized anti-CEA antibody); or an anti-CD40 antibody (e.g., as disclosed in U.S. Pat. No. 6,838,261).

Other suitable antibodies include, but are not limited to, antibodies against the following antigens: CA125, CA15-3, CA19-9, L6, Lewis Y, Lewis X, alpha fetoprotein, CA 242, placental alkaline phosphatase, prostate specific membrane antigen, prostatic acid phosphatase, epidermal growth factor, MAGE-1, MAGE-2, MAGE-3, MAGE-4, anti-transferrin receptor, p97, MUC1-KLH, CEA, gp100, MART1, Prostate Specific Antigen, IL-2 receptor, CD20, CD52, CD33, CD22, human chorionic gonadotropin, CD38, CD40, mucin, P21, MPG, and Neu oncogene product.

In some embodiments, the therapeutic agent is an immunomodulatory agent. The immunomodulatory agent can be, for example, gancyclovir, etanercept, tacrolimus, cyclosporine, rapamycin, REVLIMID (lenalidomide), cyclophosphamide, azathioprine, mycophenolate mofetil or methotrexate. Alternatively, the immunomodulatory agent can be, for example, a glucocorticoid (e.g., cortisol or aldosterone) or a glucocorticoid analogue (e.g., prednisone or dexamethasone).

In some typical embodiments, the immunomodulatory agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists. In some embodiments, the immodulatory agent is a cytokine, such as G-CSF, GM-CSF or IL-2.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, Ianopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, Ionapalen, esculin, diethylcarbamazine, phenantroline, baicalein, proxicromil, thioethers, diallyl sulfide and di-(1-propenyl) sulfide.

Leukotriene receptor antagonists include calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products Way 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SKandF-104493, Leo Denmark SR-2566, Tanabe T-757 and Teijin TEI-1338.

EXAMPLES

The invention is further described in the following examples, which are in not intended to limit the scope of the invention. Cell lines described in the following examples were maintained in culture according to the conditions specified by the American Type Culture Collection (ATCC) or Deutsche Sammlung von Mikroorganismen und Zellkulturen GmbH, Braunschweig, Germany (DMSZ). Cell culture reagents were obtained from Invitrogen Corp., Carlsbad, Calif.

Example 1

Construction of Chimeric Anti-CD70 Antibody

To determine the cDNA sequences encoding the light ($V_L$) and heavy ($V_H$) chain variable regions of 1F6 and 2F2 mAb, total RNA was isolated from the 1F6 and 2F2 hybridomas using TRIzol® Reagent (Invitrogen, Carlsbad, Calif.) according to the manufacturer's instructions. Gene-specific primers mIgcK1: 5'-CTT CCA CTT GAC ATT GAT GTC TTT G-3' (SEQ ID NO:41) and mIgG1: 5'-CAG GTC ACT GTC ACT GGC TCA G-3' (SEQ ID NO:42) were applied to reverse transcribe the light chain variable ($V_L$) and heavy chain variable ($V_H$) first strand cDNAs from both RNA preparations, respectively. First strand cDNA reactions were run using the SuperScript™ First Strand Synthesis System for RT-PCR from Invitrogen. The $V_L$ and $V_H$ cDNAs were then poly-G tailed using terminal deoxynucleotidyl transferase (TdT) and the supplied TdT buffer, according to conditions specified by the manufacturer (Invitrogen). Poly-G tailed $V_L$ and $V_H$ first strand cDNAs were then subjected to PCR amplification. The forward primer for both the $V_L$ and $V_H$ PCRs was ANCTAIL: 5' GTC GAT GAG CTC TAG AAT TCG TGC CCC CCC CCC C-3' (SEQ ID NO:43). The reverse primer for amplifying the $V_L$ was HBS-mck: 5'-CGT CAT GTC GAC GGA TCC AAG CTT CAA GAA GCA CAC GAC TGA GGC AC-3' (SEQ ID NO:44). The reverse primer for amplifying the $V_H$ was HBS-mG1: 5'-CGT CAT GTC GAC GGA TCC AAG CTT GTC ACC ATG GAG TTA GTT TGG GC-3' (SEQ ID NO:45). PCRs were run with Ex Taq and the supplied reaction buffer in conditions specified by the manufacturer (Fisher Scientific, Pittsburgh, Pa.). The $V_L$ and $V_H$ PCR products were then cut by HindIII and EcoRI and cloned into HindIII/EcoRI-cut pUC19. Recombinant plasmid clones were identified, and the nucleotide sequences for the 1F6 and 2F2 hybridomas were determined.

Complementarity determining regions (CDRs) in the heavy and light chains of 1F6 and 2F2 mAbs were determined according to the criteria described in Kabat et al., 1991, *Sequences of Proteins of Immunological Interest*, Washington D.C., US Department of Health and Public Services; Chothia and Lesk, 1987, *J. Mol. Biol.* 196:901-17 (FIGS. 1 and 2). Sequence alignments at both the cDNA and amino acid levels revealed that closely related light chain genes were probably utilized in both hybridomas. There is a 92% sequence identity between 1F6 $V_L$ and 2F2 $V_L$ at the amino acid level. Sequence comparison of the CDRs shows that 1F6 CDR-L1 is identical to 2F2 CDR-L1, only one divergent substitution is present between 1F6 CDR-L2 and 2F2 CDR-L2, and only 2 conservative substitutions are present between 1F6 CDR-L3 and 2F2 CDR-L3 (FIG. 3). On the other hand, a higher degree of sequence diversity is present between 1F6 $V_H$ and 2F2 $V_H$; about 66 of 137 amino acid residues are different between the 2 $V_H$s. Sequence comparison of the CDRs shows that 5 of 10 residues are different between 1F6 CDR-H1 and 2F2 CDR-H1 (3 of the 5 substitutions are divergent), 12 of 17 residues are different between 1F6 CDR-H2 and 2F2 CDR-H2 (9 of the 12 substitutions are divergent), and 5 of 9 residues are different between 1F6 CDR-H3 and 2F2 CDR-H3 (4 of the 5 substitutions are divergent) (FIG. 3).

An expression vector containing both the chimeric 1F6 heavy and light chains was constructed, as described infra. In this vector, each of the polypeptide chains is under the control of a copy of the CHEF1 promoter, along with an associated CHEF1 intron sequence and an immunoglobulin polyA region. For construction of this large vector, it was necessary to assemble the chimerized heavy and light chain sequences in separate "chimerization" plasmids, each encoding a section of the final construct. The final expression construct was then assembled via three-way ligation with a third vector encoding the rest of the necessary control regions. DG44 CHO cells were transformed with this plasmid and a clonal line with good production was isolated.

Construction of the Heavy Chain Chimerization Vector

A chimerization vector, pSG850, had been previously constructed by cloning a 6 kb NotI-XhoI fragment of a CHEF1 vector into a Bluescript vector. This fragment contains part of the CHEF1 5' intron, a chimeric IgG$_1$ antibody heavy chain, and a portion of a genomic sequence from the region just downstream of the human IgG$_4$ constant region containing a polyA signal. Replacement of the heavy chain variable region with that from 1F6 resulted in a plasmid carrying the chimeric 1F6 sequence. To prepare this construct, the entire 1F6 heavy chain variable region sequence was amplified via PCR from the sequencing vector. The forward oligonucleotide primer 5'-ATA AAT AAG CTT ACC GCC ACC ATG GCT GGG GTG TGG ACC TTG-3' (SEQ ID NO:46) encoding a HindIII restriction site, a consensus Kozac sequence 5' to the coding sequence for the heavy chain leader, and sequence homologous to the leader sequence was used. The reverse primer 5'-ATA AAG GCT AGC TGA GGA GAC GGT GAC TGA GGT-3' (SEQ ID NO:47) encoded sequence homologous to the 3' end of the variable region and a NheI restriction site. The PCR product was digested with HindIII and NheI. The pSG850 vector was digested with the same enzymes to remove the existing variable region and the larger vector fragment was isolated. Ligation of the 1F6 $V_H$ and the pSG850 vector fragments resulted in the construction of pJC140 containing the chimeric 1F6 heavy chain.

Construction of the Light Chain Chimerization Vector

A chimerization vector, pSG855, had been previously constructed by cloning a 4 kb XhoI-XbaI fragment of a CHEF1 vector into a Bluescript vector. This fragment contains a portion of the human IgG$_4$ downstream region, the CHEF1 promoter region, the CHEF1 5' intron, a chimeric antibody kappa light chain, and the human kappa downstream region containing a polyA signal. Replacement of the existing light chain variable region with that from 1F6 resulted in a plasmid carrying the chimeric 1F6 kappa sequence. To prepare this construct, the entire 1F6 light chain variable region sequence was amplified via PCR from the sequencing vector. The forward oligonucleotide primer 5'-ATA AAG AAG CTT ACC GCC ACC ATG GAG ACA GAC ACA CTC CTG-3' (SEQ ID NO:48) encoding a HindIII restriction site, a consensus Kozac sequence 5' to the coding sequence for the light chain leader, and sequence homologous to the leader sequence was used. The reverse primer 5'-ATA AAG GAA GAC AGA TGG TGC AGC CAC AGT CCG TTT GAT TTC CAG CTT GGT GCC-3' (SEQ ID NO:49) encoded sequence complementary to the last 24 base pairs of the light chain variable region and the first 24 base pairs of the kappa constant region, including a BbsI restriction site. The PCR product was digested with HindIII and BbsI. The pSG855 vector was digested with the same enzymes to cut out the existing variable region and the larger vector fragment was isolated. Ligation of the 1F6 $V_L$ and the pSG855 vector fragments resulted in the construction of pJC160 containing the chimeric 1F6 light chain.

Assembly of the c1F6 Expression Vector

The expression vector carrying both chains of the chimeric 1F6 (c1F6) antibody was assembled via a three-way ligation. The CHEF1 expression vector pDEF14 was digested with NotI and XbaI, and the 19.7 kb vector fragment was isolated. pJC140 was digested with NotI and XhoI and the 6 kilobase fragment was isolated. pJC160 was digested with XhoI and XbaI and the 4 kilobase fragment was isolated. These three fragments were mixed in a 1:1:1 molar ratio in a ligation reaction, and the ligation product was used to transform XL10-Gold cells. Clones were screened by restriction mapping, and a correct clone was confirmed by sequencing of the heavy and light chain coding regions. FIG. 4 shows the plasmid map of the final product.

Transfection of DG44 Cells with pDEF14-1F6

200 µg of pDEF14-1F6 plasmid DNA was linearized with PvuI overnight at 37° C., and then ethanol precipitated after the addition of 100 µg sonicated salmon sperm DNA (Specialty Media cat# S-005-G Lavallette, N.J.). The DNA was resuspended in 350 µl sterile dH$_2$O and 450 µl 2×HeBS (40 mM HEPES-NaOH pH 7.0, 274 mM NaCl, 10 mM KCl, 1.4 mM Na$_2$HPO$_4$, and 12 mM dextrose).

DG44 Chinese Hamster Ovary cells were from a bank of cells which had been previously adapted to serum-free suspension. The DG44 were cultured in shake flasks to a density of approximately 1×10$^6$ cells/ml in nonselective media, serum-free Excell325 (JRH Biosciences, Inc., Lenexa, Kans.) supplemented with recombinant human insulin, L-glutamine, hypoxanthine and thymidine. 2×10$^7$ cells were harvested by centrifugation in sterile 15 ml tubes, washed with CMF-PBS and repelleted. The washed DG44 cells were resuspended in the DNA solution and pulsed once in a Bio-Rad GenePulser II electroporator (960 µF, 290 volts, time constant 9-11 msec) (Bio-Rad, Hercules, Calif.). The cells were allowed to recover at room temperature for 8-10 minutes. Cells were then added to 10 ml of the non-selective, serum-free medium above, transferred to stationary T75 flasks and allowed to recover for two days at 37° C. and 5% $CO_2$. The transfection pool was then centrifuged at low speed and resuspended in selective medium (same as the medium described above except without hypoxanthine and thymidine, designated Excell325SEL) and passaged until the culture reached a viability of >90%. A fed-batch culture of this transfection pool yielded cAb with specificity comparable to the murine 1F6 Ab.

Subcloning of c1F6 Transfection Pool

Using a feeder-cell method, the c1F6 transfection pool cells were mixed with DG44 cells at a ratio of 1:2000 in Excell325SEL (without hypoxanthine or thymidine) and plated at a density of 1000 cells/well into four 96-well plates. This gave an effective density of 0.5 c1F6 cells/well along with 1000 DG44 feeder cells/well. The DG44 cells died off after a few days due to their requirement for HT. DG44 cells plated at 10,000 cells/well under the same conditions were shown to exhibit no survival. The two plates yielded 34 wells with outgrowth of single colonies. The 34 clonal wells were scaled up to 24-well plates and extinct-culture supernatants from the wells were screened for cAb titer via a standard anti-chimeric antibody ELISA. Six subclones were chosen based on titer and growth for further screening via shake flask fed-batch culture. One of these clones demonstrated a cell-specific productivity of approximately 20 picograms per cell per day, with a final fed-batch titer of 1.1 g/l.

Example 2

Chimeric 1F6 Mediates ADCC Against $CD70^+$ Tumor Cell Lines

Figure 5:
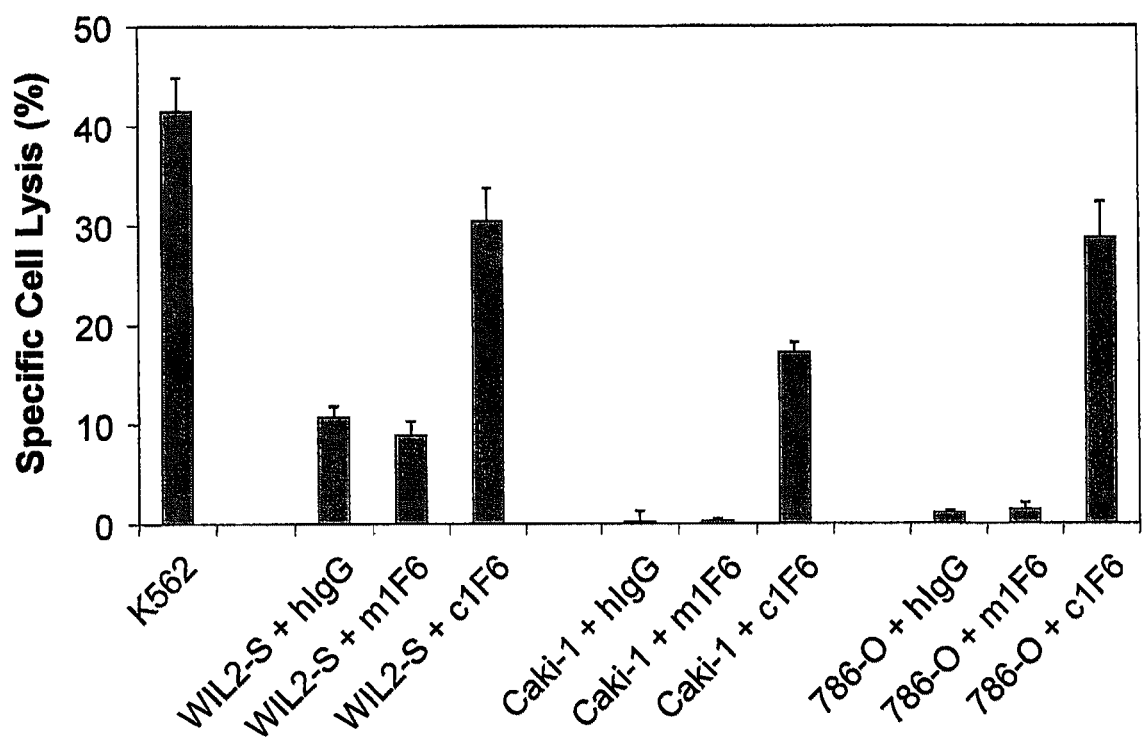
FIG. 5. Chimeric 1F6 anti-CD70 antibody mediates antibody-dependent cellular cytotoxicity (ADCC). $Na_2^{51}CrO_4$-labeled target cells (WIL2-S B lymphoblastoid cells, Caki-1 renal cell carcinoma cells, and 786-0 renal cell carcinoma cells) were coated with chimeric 1F6 (c1F6), murine 1F6 (m1F6), or human IgG (hIgG) and mixed with peripheral blood mononuclear cells (PBMC) at an effector to target ratio of 30 CD16$^+$ cells to 1 target cell. After 4 hours, the supernatants from lysed cells were measured on a scintillation counter. The percent specific lysis was calculated as {(test sample cpm–spontaneous cpm)÷(total cpm–spontaneous cpm)}×100. Points represent the mean±standard deviation of triplicate samples.

The ability of c1F6 to mediate ADCC against the $CD70^+$ cell lines WIL2-S, Caki-1 and 786-O was measured using a standard $^{51}Cr$ release assay. Tumor cells were labeled for one hour with 100 µCi $Na_2^{51}CrO_4$, washed thoroughly to remove unincorporated radioisotope, then plated in a 96-well plate at a concentration of 5,000 cells per well. Antibodies c1F6, m1F6 or human Ig were added to appropriate wells at a final concentration of 1 µg/ml for 0.5 hours prior to the addition of effector PBMC. PBMC were adjusted to reflect an effector cell to target cell ratio of 30 $CD16^+$ cells:1 target cell. After 4 hours incubation, the $^{51}Cr$ released from lysed cells was measured and the percent specific lysis calculated as {(test sample cpm−spontaneous cpm)÷(total cpm−spontaneous cpm)}× 100. Spontaneous release of isotope was determined from the supernatant of target cells incubated in medium alone. Total counts were determined from target cells lysed with 2% triton-X. As shown in FIG. 5, c1F6 effectively induced the lysis of each tumor target whereas tumor cells treated with CD70 binding murine 1F6 (m1F6) or non-binding control human Ig (hIg) were minimally affected. Lysis of the NK sensitive target K562, in the absence of antibody, confirmed the presence of effector cells with cytolytic potential within PBMC.

Example 3

Chimeric 1F6-Coated Target Cells Recognized by PBMC from Multiple Donors

Figure 6:
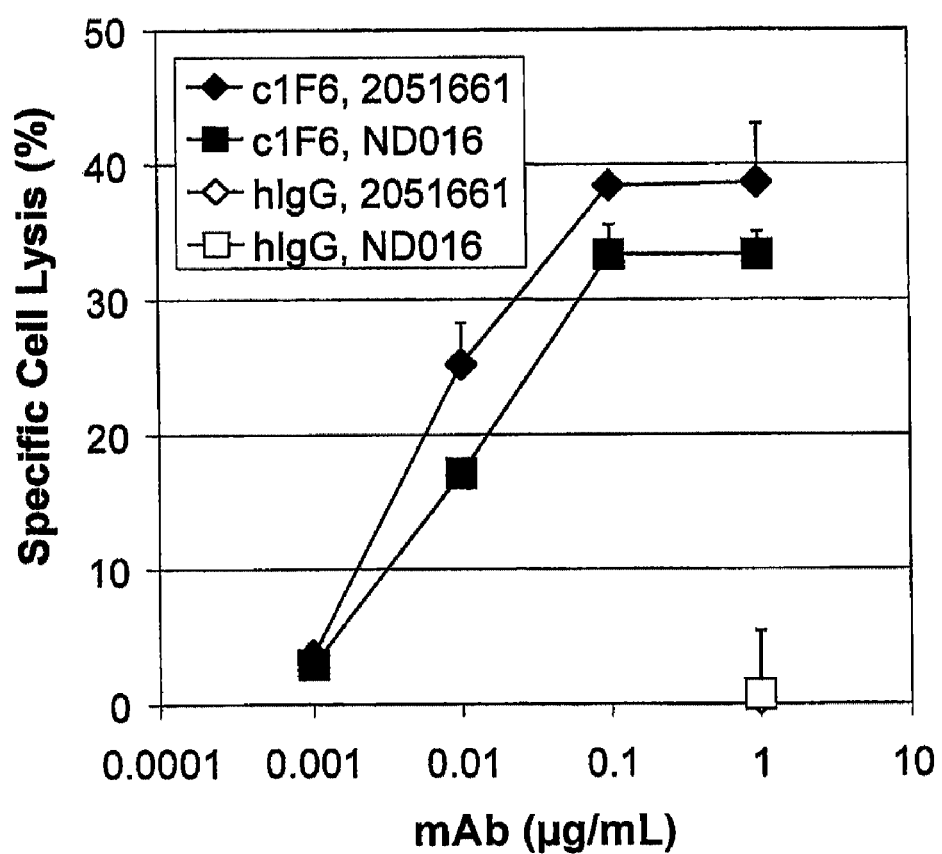
FIG. 6. Chimeric 1F6-coated target cells recognized by PBMC from multiple donors. $Na_2^{51}CrO_4$-labeled Caki-1 renal cell carcinoma cells were coated with varying concentrations of chimeric 1F6 or non-binding control human IgG (hIgG) and mixed with PBMC from two normal donors (2051661 and ND016) at an effector to target cell ratio of 17 CD16$^+$ cells to 1 target cell. Specific lysis was assessed by measuring chromium-51 activity in culture supernatants four hours later as described in FIG. 5.

Caki-1 renal cell carcinoma cells were labeled with $Na_2^{51}CrO_4$, treated with graded doses of c1F6, and then incubated with effector PBMC from two normal donors. Specific lysis was assessed after 4 hours incubation as described in Example 2. Donor 2051661 and ND016 efficiently lysed Caki-1 target cells treated with 1 or 0.1 µg/ml c1F6 (FIG. 6). Specific lysis decreased in an antibody dose-dependent manner thereafter, and was negligible when target cells were treated with 0.001 µg/ml c1F6. Target cells mixed with non-binding control Ig (hIg) were not lysed by PBMC from either donor.

Example 4

Chimeric 1F6-Coated Lymphoid Cell Lines are Susceptible to Lysis by PBMC

Figure 7:
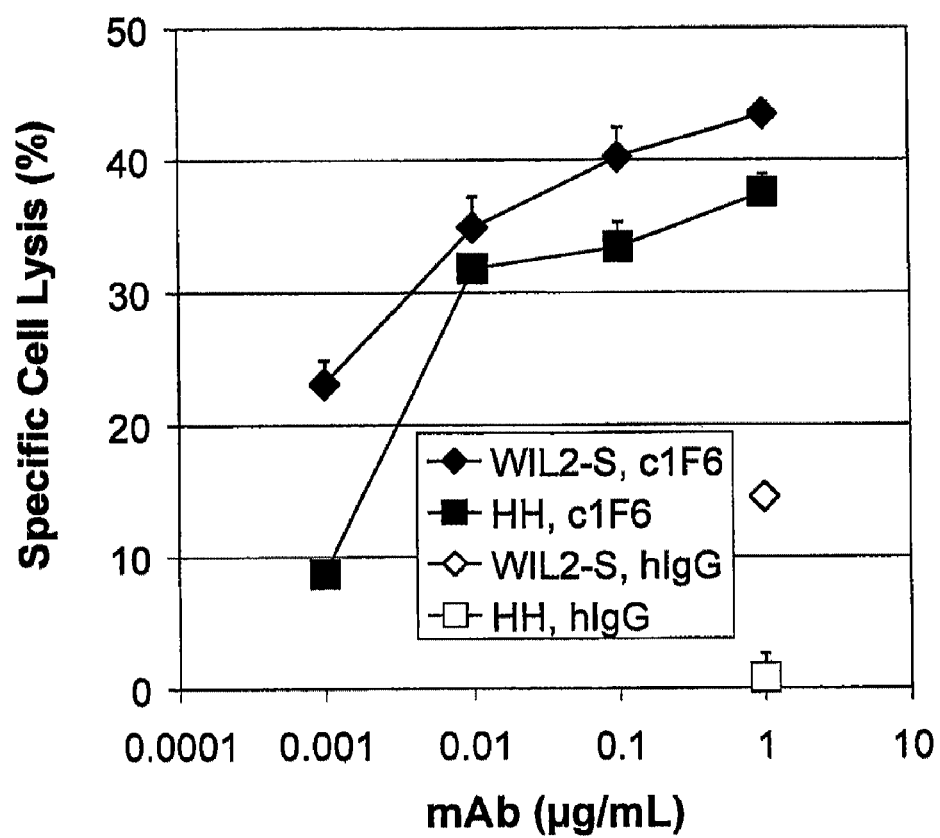
FIG. 7. Chimeric 1F6 mediates ADCC against lymphoid cell lines. CD70$^+$ B lymphoblastoid cells (WIL2-S) and cutaneous T cell lymphoma cells (HH) were labeled with $Na_2^{51}CrO_4$ then mixed with chimeric 1F6 or human Ig (hIgG) at various concentrations as indicated. PBMC-containing CD16$^+$ cells were added to the target cells at a ratio of 18:1 (CD16$^+$ cells:target) and percent lysis determined after a four-hour incubation as described in FIG. 5.

To determine if transformed cells of B and T cell lineage were also susceptible to c1F6-mediated ADCC activity, $CD70^+$ B lymphoblastoid cells (WIL2-S) and cutaneous T cell lymphoma cells (HH) were labeled with $Na_2^{51}CrO_4$ and then mixed with c1F6 or human Ig at various concentrations, as indicated. PBMC were added to the target cells at a ratio of 18:1 ($CD16^+$ cells:target) and percent lysis determined after a four-hour incubation as described in Example 2. FIG. 7 shows that both WIL2-S and HH are recognized and lysed by PBMC effector cells in the presence of c1F6. Whereas treatment of target cells with non-binding control antibody resulted in minimal cell lysis, treatment of WIL2-S and HH cells with c1F6 at 1 µg/ml enabled 43.5% and 37.5% target cell death, respectively.

Figure 8:
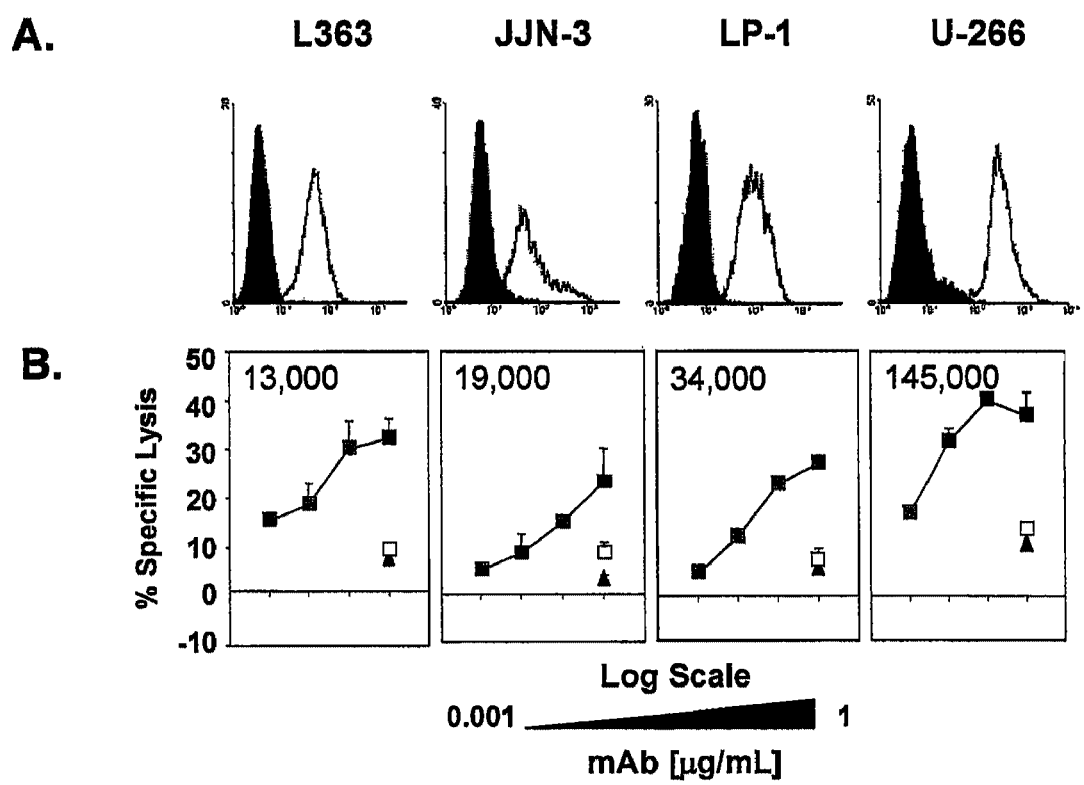
FIG. 8. Chimeric 1F6 mediates ADCC against CD70$^+$ multiple myeloma cell lines. (A) Expression of CD70 by multiple myeloma cell lines. L-363, JJN-3, LP-1 and U-266 cells were stained with a murine anti-CD70 antibody (open histograms) or a non-binding murine IgG control antibody (solid histograms). Antibody binding was detected with FITC-conjugated anti-mouse IgG and the cells analyzed by flow cytometry. (B) ADCC activity of c1F6. CD38$^{+/-}$/CD138$^+$/CD70$^+$ multiple myeloma cell lines were labeled with $Na_2^{51}CrO_4$ and then mixed with chimeric 1F6 (solid squares) or human Ig (solid triangle) at various concentrations as indicated. CD16$^+$ cells enriched from PBMC were added to the target cells at a ratio of 15:1 (CD16$^+$ cells:target) and the percent lysis determined after a four-hour incubation as described in FIG. 5. ADCC activity was blocked by pre-incubating the CD16$^+$ effector cells with antibody to FcγRIII (CD16, open squares). Numbers within each graph indicate the number of CD70 molecules expressed by each cell line estimated using the QIFIKIT® (DakoCytomation, Carpinteria, Calif.)
Figure 9:
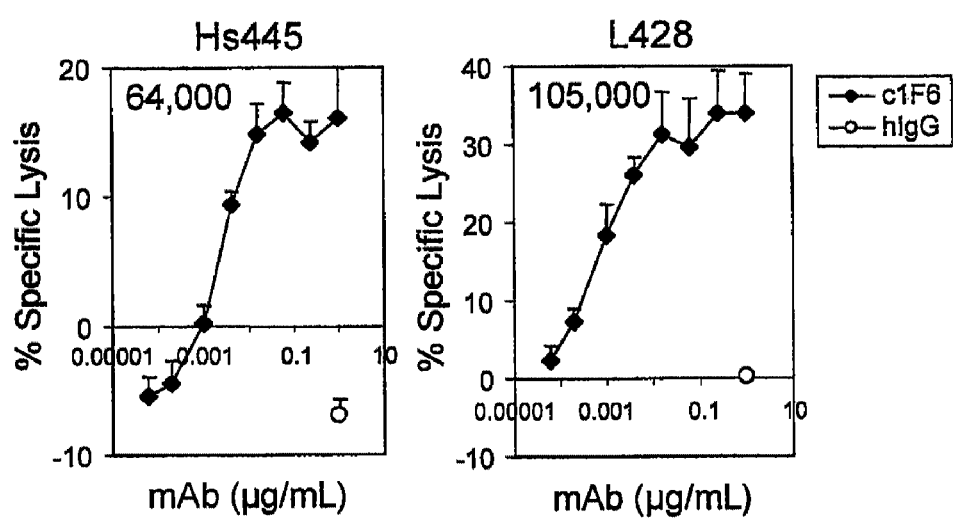
FIG. 9. Chimeric 1F6 mediates ADCC against Hodgkin's disease (HD) cell lines. CD70$^+$ HD cell lines Hs445 and L428 were labeled with $Na_2^{51}CrO_4$ then mixed with chimeric 1F6 or human Ig (hIgG) at concentrations indicated. PBMC-containing CD16$^+$ cells were added to the target cells at a ratio of 18:1 (CD16$^+$ cells:target) and percent lysis determined after a four-hour incubation as described in FIG. 5. Numbers within each graph indicate the number of CD70 molecules expressed by each cell lines estimated using the QIFIKIT® (DakoCytomation, Carpinteria, Ca)

The multiple myeloma cell lines L-363, JJN-3, LP-1 and U-266 were tested for expression of CD70 by flow cytometry. As shown in FIG. 8A, CD70 was readily detected on each. The susceptibility of these multiple myeloma cell lines to chimeric 1F6-mediated ADCC was determined as described in Example 2. Target cells treated with 1 or 0.1 µg/ml c1F6 were efficiently lysed (FIG. 8B). Specific lysis decreased in an antibody dose-dependent manner thereafter, and was negligible when target cells were treated with 0.001 µg/ml c1F6. Target cells mixed with non-binding control Ig (hIg) were not lysed. Blockade of FcγRIII by pre-incubating effector cells with anti-CD16 antibody abolished ADCC activity, confirming the dependence of lytic activity on interaction of antibody with FcR-bearing effector cells. Similar dose-dependent chimeric 1F6-mediated ADCC was also observed using $CD70^+$ Hodgkin's disease cell lines as targets (FIG. 9).

Example 5

CD70 Expression on Activated T Cells During an Antigen-Specific In Vitro Immune Response A 9-amino acid peptide (GILGFVFTL, M1 peptide, (SEQ ID NO:50)) derived from the influenza virus matrix protein binds to the peptide-binding groove of the HLA-A0201 molecule. Presentation of the M1 peptide by HLA-A0201 expressing antigen presenting cells to autologous T cells specifically stimulates the activation and expansion of $CD8^+$ cytotoxic T cells expressing the T cell receptor Vβ17 chain (Lehner et al., 1995, *J. Exp. Med.* 181: 79-91), constituting a convenient in vitro experimental system to track the activation and expansion of antigen-specific T cells to their cognate antigen.

Figure 10:
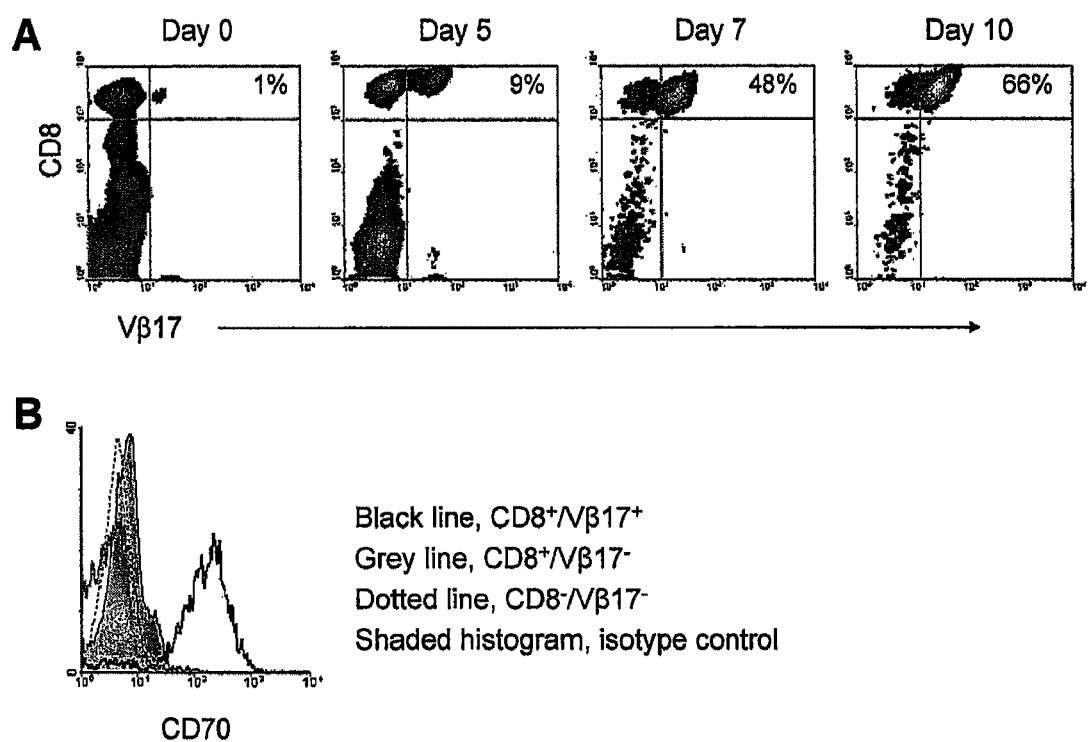
FIG. 10. CD70 induced during antigen-specific T cell expansion. PBMCs from a normal HLA-A0201 donor were stimulated with the M1 peptide derived from the influenza virus matrix protein. At the indicated time points the emergence of CD8$^+$/Vβ17$^+$ T cells were enumerated by flow cytometry (A). Five days after initiation of M1 peptide stimulation, expression of CD70 on the different indicated T cell subsets was determined (B). The kinetics of CD70 expression on CD8$^+$/Vβ17$^+$ cells during M1 stimulation is represented as the percent CD8$^+$/Vβ17$^+$ cells that express CD70 (C) and the mean fluorescence intensity (MFI) of CD70 expression as measured by flow cytometry (D).
Figure 10:
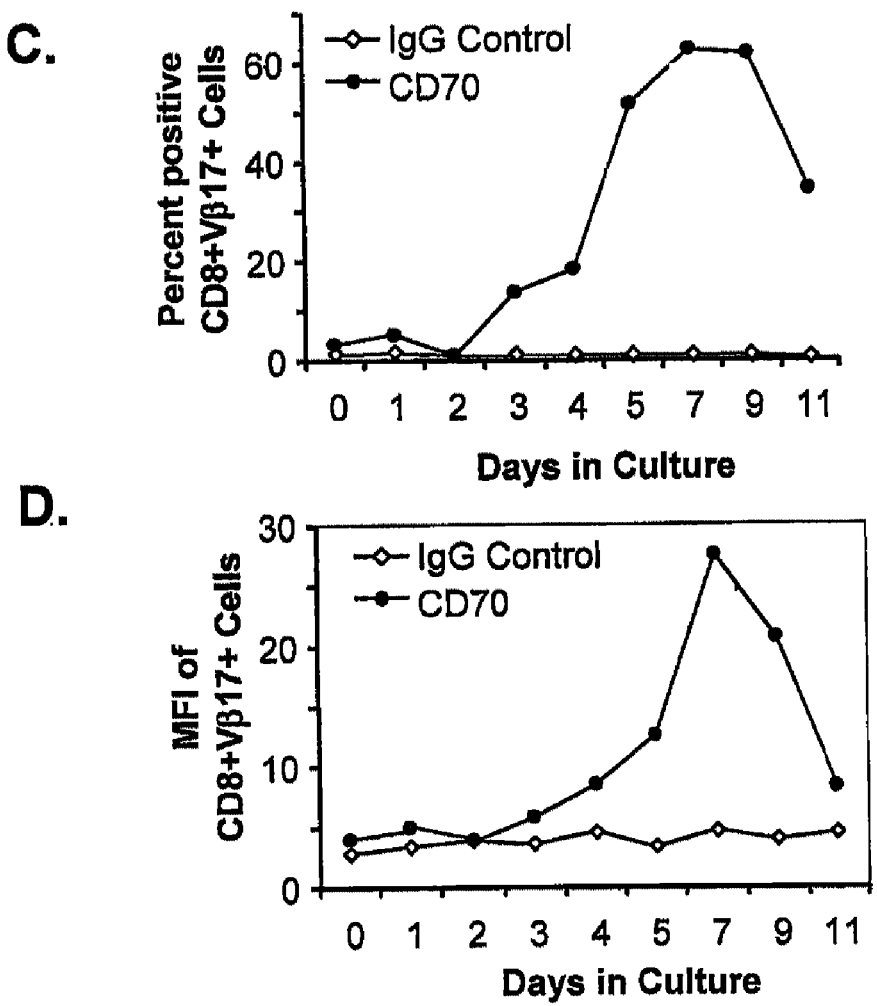

To examine CD70 expression on activated antigen-specific T cells, PBMCs from a normal donor expressing HLA-A0201 were stimulated with the M1 peptide. PBMCs were seeded at $2 \times 10^6$ cells/ml with 5 µg/ml of M1 peptide in AIMV medium supplemented with 5% human AB serum. IL-2 (Proleukin, Chiron, Emeryville, Calif.) and IL-15 (R and D Systems, Minneapolis, Minn.) were added to a final concentration of 20 IU/ml and 5 ng/ml, respectively, once every two days beginning on day 2 after culture initiation. The expansion of $CD8^+$ Vβ17$^+$ T cells and induction of CD70 on the $CD8^+$/Vβ17$^+$ were followed by three-color flow cytometry. Vβ17⁺ T cells were identified by the anti-TCRVβ17 mAb clone E17.5F3 (Beckman Coulter, Miami, Fla.). Results showed that whereas 1% of the cells within the lymphocyte population were CD8⁺/Vβ17⁺ at culture initiation, the percentage of CD8⁺/Vβ17⁺ progressively increased to 9% on day 5, to 48% on day 7, and to 66% on day 10 (FIG. 10A). CD70 expression was only detected in the CD8⁺/Vβ17⁺ subpopulation (FIG. 10B), confirming that CD70 was induced on activated T cells responding to the antigenic stimulation but not on the bystander, antigen-non-specific T cells. The kinetics of CD70 expression was analyzed in the CD8⁺/Vβ17⁺ population. CD70 became detectable 3 days after antigen stimulation and was expressed on approximately 60% of the expanding CD8⁺/Vβ17⁺ cells by day 7 (FIG. 10C). The highest level of CD70 expression as indicated by mean fluorescence intensity (MFI) was also detected on day 7 (FIG. 10D). The percentage of CD70⁺/CD8⁺/Vβ17⁺ cells and the MFI of CD70 expression on the CD8⁺/Vβ17⁺ started to decline thereafter (FIG. 10 C, D).

Example 6

In Vitro Deletion of CD70 Antigen-Specific T Cells by c1F6

To test the ability of c1F6 to deplete antigen-specific activated T cells, PBMC from a normal donor expressing HLA-A0201 were stimulated with the M1 peptide in the presence or absence of anti-CD70 antibody. PBMC were seeded in a 24-well plate at a concentration of 0.5×10⁶ cells/ml with 5 μg/ml M1 peptide in 2 ml medium supplemented with IL-2 and IL-15, as described supra. Nonbinding immunoglobulin, murine 1F6 (m1F6) or chimeric 1F6 (c1F6) antibody was added at a concentration of 1 μg/ml at the start of the culture and on days 2 and 5 post culture initiation. On day 5, half of the spent culture supernatant was replaced with fresh cytokine-containing medium. On day 9, the percentage of antigen-reactive cells (CD8⁺/Vβ17⁺ population) was determined by flow cytometric analysis of cells stained with FITC-conjugated anti-Vβ17- and PE-Cy5-conjugated anti-CD8 antibodies. Some of the cell cultures were additionally supplemented on days 0 and 5 with 0.25×10⁶ CD16⁺ cell-enriched PBMC. To enrich for CD16⁺ cells, T cells, B cells and monocytes were depleted by labeling PBMC with anti-CD8, anti-CD4, anti-CD20, and anti-CD14 antibodies followed by immunomagnetic bead selection. Over the course of the study, the antigen-specific CD8⁺/Vβ17⁺ cells expanded to comprise 47.2% of all viable cells within the culture in the absence of antibody. Similarly, CD8⁺/Vβ17⁺ cells represented 48.3% and 38.5% of all cells present in cultures treated with the nonbinding antibody and murine anti-CD70 antibody, respectively. In contrast, substantial inhibition of CD8⁺/Vβ17⁺ expansion was observed in cultures treated with chimeric anti-CD70 antibody (12.5%). The reduction in antigen-reactive cells was even more pronounced when CD16⁺ effector cells were added to the culture. CD8⁺/Vβ17⁺ cells made up only 1.5% of all cells in c1F6-treated cultures compared to 32.6% in untreated cultures and 22.4% or 22.9% of cells treated with irrelevant and m1F6 antibodies, respectively. These results demonstrate that c1F6 selectively targets and prevents the expansion of antigen-activated T cells.

Example 7

Figure 11:
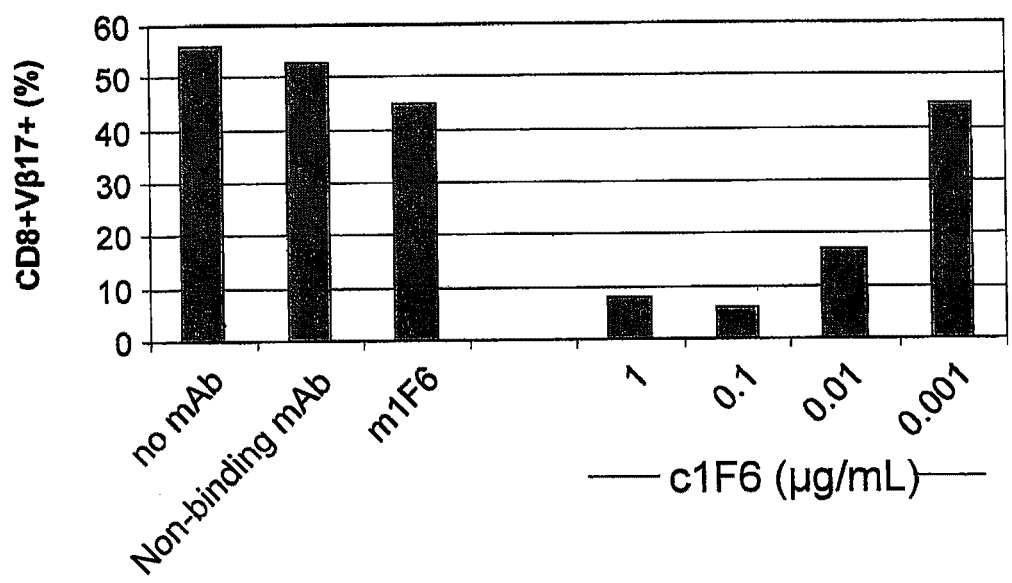
FIG. 11. Dose response comparison of c1F6 on depletion of antigen-specific CD8$^+$/Vβ17$^+$ cells. PBMCs from a normal HLA-A0201 donor were stimulated with the M1 peptide as described in FIG. 10. Peptide-stimulated cultures were untreated or initiated with concurrent addition of irrelevant control mAb, murine anti-CD70 antibody (m1F6) or graded doses of chimeric anti-CD70 antibody (c1F6), as indicated. The percent CD8$^+$/Vβ17$^+$ cells after 9 days was determined by flow cytometry.

Dose ResponseCcomparison of Anti-CD70 on Depletion of Antigen-Specific CD8+/Vβ17+ Cells To confirm the ability of c1F6 to prevent the expansion of antigen-activated T cells and to further evaluate the antibody-dependent nature of this response, a second study was performed in which M1-peptide stimulated PBMCs were initiated in the presence of graded doses of c1F6 (FIG. 11). Antigen-specific CD8⁺/Vβ17⁺ cells recovered on day 9 from untreated cultures represented 56% of all viable cells. In contrast, addition of c1F6 to the cultures on day 0 significantly limited expansion of the antigen-reactive population in a dose dependent manner. CD8⁺/Vβ17⁺ cells comprised 7.8, 5.8, and 16.9% of all cells in cultures treated with 1, 0.1 and 0.01 μg/ml c1F6, respectively. c1F6 antibody added at a concentration of 0.001 μg/ml did not prevent CD8⁺/Vβ17⁺ cell expansion.

Example 8

Chimeric 1F6 Mediates Complement-Dependent Cytotoxicity in CD70⁺ B and T Cells

Figure 12:
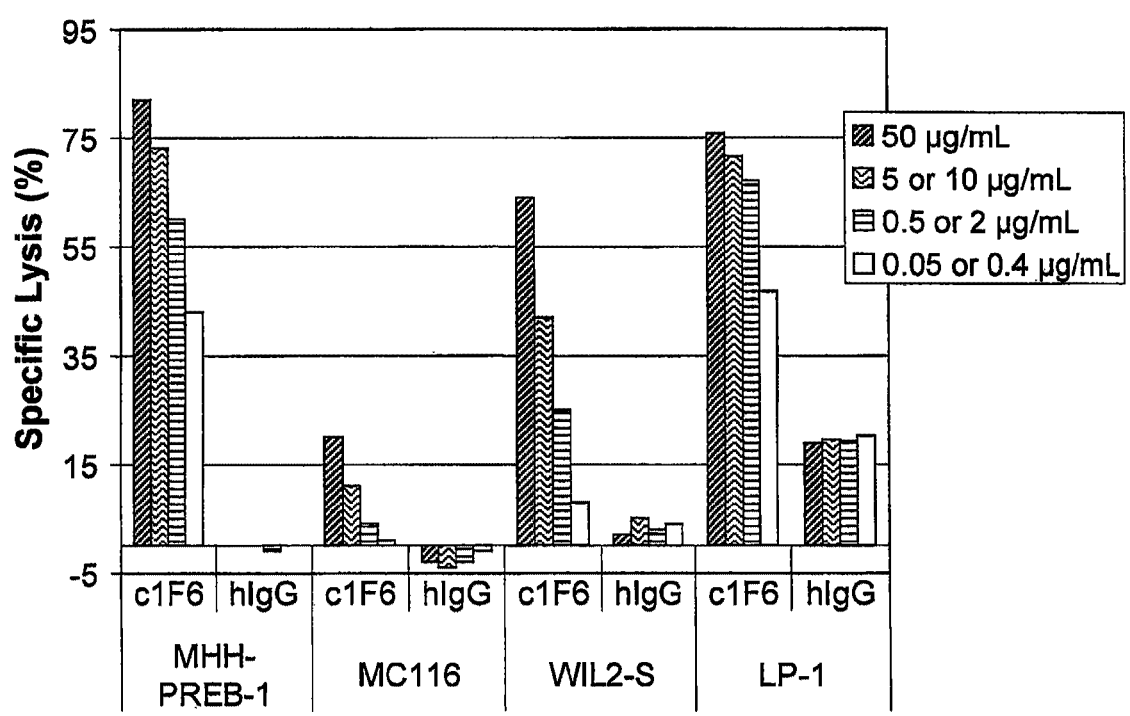
FIG. 12. Chimeric 1F6 mediates complement-dependent cytotoxicity in CD70$^+$ B cells. The CD70$^+$ lymphoblastic NHL line (MHH-PREB-1), EBV-Burkitt's lymphoma line (MC116), lymphoblastoid B cell line (WIL2-S), and multiple myeloma cell line (LP-1) were incubated with graded doses of the indicated antibodies in the presence of 10% normal human serum. For MHH-PREB-1, MC116 and WIL2-S antibodies were used at 50, 5, 0.5, and 0.05 µg/mL, while for LP-1 antibodies were used at 50, 10, 2, and 0.4 µg/mL. Human IgG (hIgG) was used as a non-binding negative control antibody. Cell lysis was assayed by cell permeability to the DNA dye, propidium iodide, detected by flow cytometry. Background cell lysis in medium only was subtracted to give specific cell lysis.

The ability of c1F6 to mediate complement-dependent cytotoxicity was examined using CD70⁺ B and T cells. In these experiments, normal human serum that was not heat-inactivated was used as the source of complement. Target cells were treated with graded doses of c1F6 or a non-binding human IgG control in the presence of normal human serum. After incubation at 37° C. for 2 hours, propidium iodide was added to a final concentration of 5 μg/ml. Cell preparations were then examined by flow cytometry. Cells stained by propidium iodide were considered to have lost plasma membrane integrity (cell lysis) as a result of antibody-mediated complement activation and formation of the membrane attach complex. Spontaneous background lysis was subtracted from antibody-mediated cell lysis to yield specific cell lysis. Using this assay, c1F6 mediated dose-dependent lysis of several CD70⁺ B cell targets (FIG. 12). These targets included a lymphoblastic non-Hodgkin's lymphoma line, MHH-PREB-1, the EBV-Burkitt's lymphoma line, MC116, the EBV⁺ lymphoblastoid B cell line, WIL2-S, and a multiple myeloma cell line, LP-1. For both MHH-PREB-1 and WIL2-S, maximum specific lysis was >50%. Specific lysis of MC116 was around 15% at the highest concentration of c1F6 used.

Figure 13:
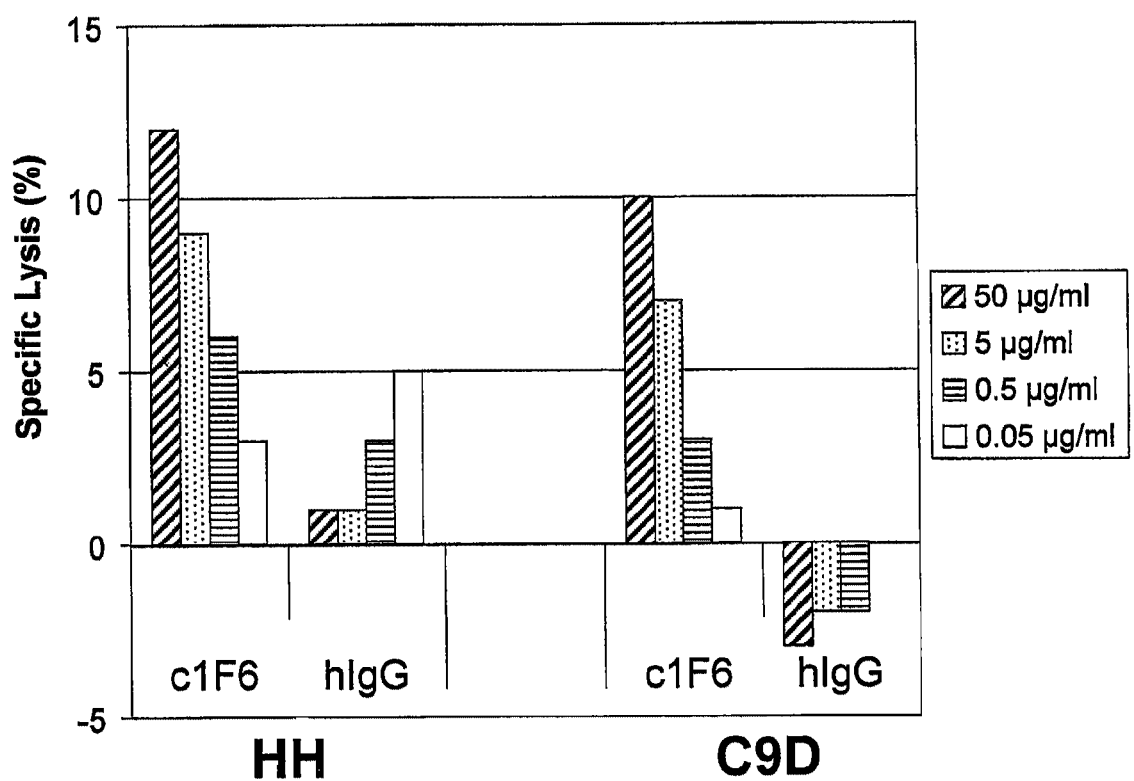
FIG. 13. Chimeric 1F6 mediates complement-dependent cytotoxicity in CD70+ T cells. c1F6-mediated CDC of the CD70+ cutaneous T cell lymphoma line HH and a CD70+ activated normal T cell line (C9D) was evaluated as described in FIG. 12.

The sensitivity of two CD70⁺ T cell targets was also examined. HH is a cutaneous T cell lymphoma cell line that constitutively expresses CD70. C9D is a normal T cell line that is maintained and propagated in culture. Stimulation of resting C9D with phytohemagglutinin (PHA, 2 μg/ml), IL-2 (100 IU/ml Proleukin® (aldesleukin) Chiron, Emeryville, Calif.), and irradiated CESS cells (ATCC, Manassas, Va.) at a 1:1 CESS:T cell ratio initiates a cell activation and expansion cycle which is accompanied by inducible surface expression of CD70. HH and CD70⁺ C9D cells were incubated with c1F6 or control IgG as described above in the presence of normal human serum. Cell lysis was assessed by propidium iodide permeability and flow cytometry (FIG. 13). Cell lysis was detected in both targets in a dose-dependent manner, demonstrating that c1F6 also mediates CDC on CD70⁺ T cell targets.

Example 9

Chimeric 1F6 Mediates ADCP Against CD70⁺ Tumor Cell Lines

Figure 14:
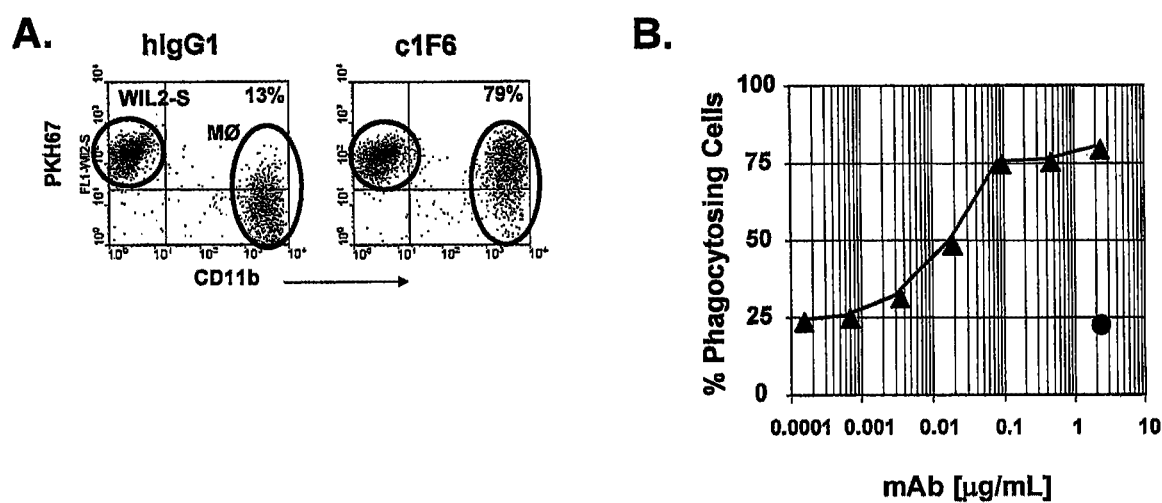
FIG. 14. Chimeric 1F6 mediates antibody-dependent cellular phagocytosis (ADCP) against CD70+ cells. CD70+ lymphoblastoid cells (WIL2-S) were labeled with a green fluorescent cell membrane dye (PKH67), treated with graded doses of c1F6 then mixed with monocyte-derived macrophages. After two hours, the mixture was incubated with a PE-conjugated anti-CD11b antibody to label the macrophage surface. Uptake of antibody-coated target cells by macrophages was determined by flow cytometric analysis of green and red double fluorescent cells. For fluorescent microscopy, CD11b+ cells were additionally stained with Alexa Fluor™568 goat anti-mouse IgG to enhance the red signal. (A) WIL2-S cells were treated with control antibody (hIgG1) or c1F6 and mixed with macrophages. The percent phagocytic cells (of total macrophages) that ingested antibody-coated target cells are indicated in the upper right quadrant. (B) WIL2-S cells were treated with graded doses of c1F6 (triangles) or nonbinding control Ig (hIgG1, circle) and the percent of phagocytic cells that ingested target cells was determined by flow cytometry.

The ability of c1F6 to mediate antibody-dependent cellular phagocytosis was examined using CD70⁺ WIL2-S cells and monocyte-derived macrophages as a source of phagocytic cells. To generate macrophages, monocytes from PBMC were adhered to tissue culture flasks for approximately 1 hour in medium containing 1% human serum. Nonadherent cells were decanted and the remaining adherent cells cultured in serum-free X-VIVO medium (BioWhittaker, Walkersville, Md.) supplemented with 500 units/mL rhGM-CSF for 11-14 days. Macrophages were ≧75% viable, were CD3$^-$/CD14$^+$/ CD11b$^+$, and expressed FcγRI, II and III. To detect c1F6-mediated ADCP, 8×10$^5$ WIL2-S target cells were stained with PKH67 (Sigma-Aldrich Corp., St. Louis, Mo.), a green fluorescent cell membrane dye, according to the manufacturer's protocol. The cells were then pre-incubated with 2 μg/mL of c1F6 in PBS for 30 minutes on ice and washed once with PBS to remove excess antibody. The target cells were combined with 2×10$^5$ macrophages in a 96-well U-bottom microtiter plate at a final ratio of 1 macrophage cell to 4 target cells in RPMI 1640 medium supplemented with 10% Ultra Low IgG FBS (Invitrogen Corp.). After a two-hour incubation at 37° C. in a 5% $CO_2$ humidified incubator, the cell mixture was labeled with PE-conjugated mouse anti-CD11b antibody to surface label the macrophages. The cells were washed once with PBS, fixed in 1% paraformaldehyde in PBS, and analyzed by flow cytometry to detect double fluorescence as a measure of phagocytic activity. For fluorescence microscopy, CD11b$^+$ cells were further labeled with Alexa Fluor™ 568 goat anti-mouse IgG (Molecular Probes, Inc., Eugene, Oreg.) to enhance the red fluorescent signal. As shown in FIG. 14A, 79% of macrophages phagocytosed WIL2-S target cells when the targets were coated with c1F6. In contrast, limited phagocytosis was observed by macrophages mixed with WIL2-S cells treated with non-binding Ig control antibody (12.8%). The double fluorescence staining indicative of phagocytosis was a result of target cell ingestion and was not due to conjugate formation, as judged by fluorescent microscopy. Green WIL2-S cellular material was clearly shown to be localized within macrophages whose membranes were stained red. WIL2-S cells treated with non-binding Ig were seen to be separate and apart from red-stained macrophages. Phagocytic activity was dependent upon antibody in a dose specific manner (FIG. 14B). Further examination revealed that CD70$^+$ transformed cell lines derived from different cancer types were all sensitive to chimeric 1F6-mediated ADCP (FIG. 15).

Example 10

In Vivo Antitumor Activity of c1F6

CD70 positive Burkitt's lymphoma line Raji and EBV-transformed lymphoblastoid cell line IM-9 were obtained from the ATCC (Manassas, Va.). Cells were grown in RPMI (Life Technologies Inc., Gaithersburg, Md.) and supplemented with 10% Fetal Bovine Serum. To establish disseminated disease, 1×10$^6$ Raji or IM-9 cells washed and resuspended in 0.2 ml PBS were injected into the lateral tail vein of C.B.-17 SCID mice (Harlan, Indianapolis, Ind.). After injection, all of the mice were pooled and then placed randomly into the various treatment groups. A single dose of 1 or 4 mg/kg of c1F6, or 4 mg/kg of control IgG was given one day after the cell implant by intravenous injection into the lateral tail vein. Mice were weighed and evaluated for signs of disease at least once per week. Mice were removed from the experiment and sacrificed when they exhibited signs indicative of disease onset characterized by one or more of the following: weight loss of 15-20% from day 0 body weight, hunched posture, lethargy, cranial swelling, or dehydration. In the Raji model median survival for the untreated and control IgG-treated groups was 21 and 24 days, respectively. Chimeric 1F6 prolonged survival in a dose-dependent manner, with a median survival of 31 and 72 days in the groups treated at 1 and 4 mg/kg of chimeric 1F6, respectively (FIG. 16). A similar increase in survival was also observed in the IM-9 model. In the absence of treatment or treatment with control IgG, the median survival was 35 and 28 days, respectively. Treatment with 1 or 4 mg/kg of c1F6 increased the median survival time to 53 and >100 days, respectively (FIG. 16). In both models the increase in survival was found to be statistically significant based on the log-rank test as indicated in FIG. 16.

Example 11

In Vivo Activity of a Humanized 1F6 Antibody in SCID Mouse Xenograft Models of Disseminated Lymphoma and Multiple Myeloma The in vivo antitumor activity of a humanized 1F6 antibody was examined in disseminated lymphoma and multiple myeloma xenograft mouse models. Humanized 1F6 antibody was prepared as described in U.S. Provisional Patent Application No. 60/673,070, filed Apr. 19, 2005 (the disclosure of which is incorporated by reference herein). To establish disseminated disease, 1×10$^6$ Raji or 1×10$^7$ MM1.S or L363 cells were injected into the lateral tail vein of C.B.-17 SCID mice. Mice were dosed with the humanized antibody or control non-binding antibody by intraperitoneal (i.p.) injection every four days for a total of six doses (Raji) or by intravenous injection into the lateral tail vein once weekly for a total of four weeks (MM.1S and L363) starting one day after cell implant. Disease requiring euthanasia was manifested by hunched posture and lack of grooming, weight loss, cranial swelling and hind limb paralysis, or, in L363-bearing mice, the development of palpable lymphoid tissue-associated tumors.

Figure 17:
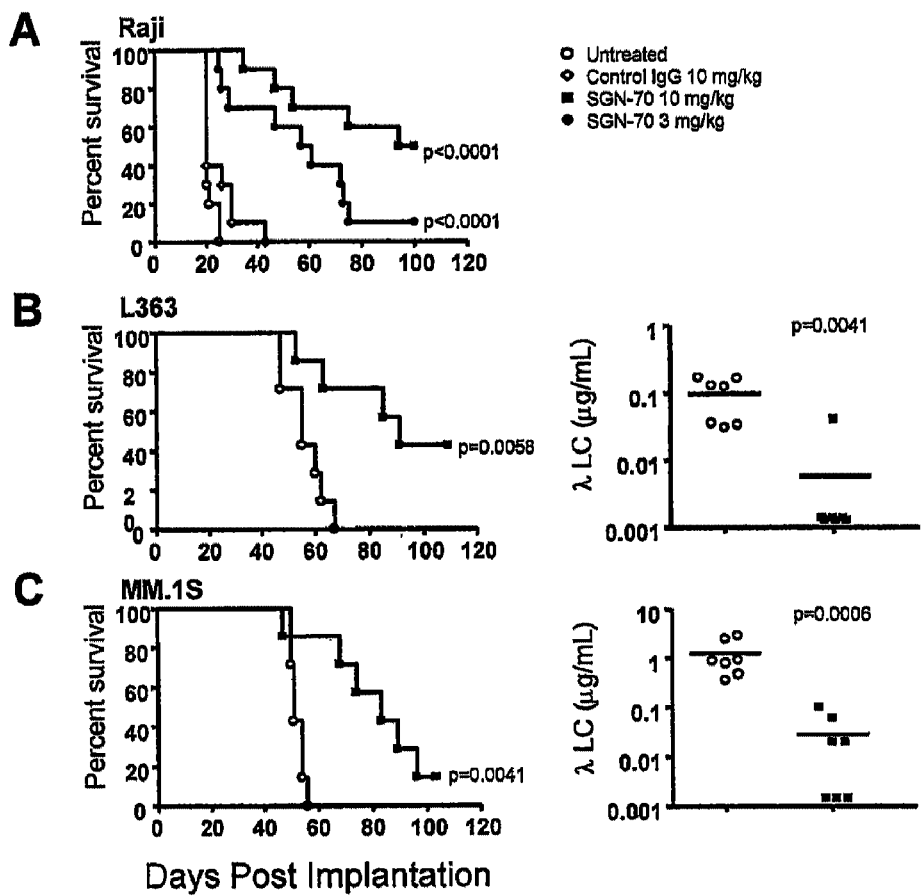
FIG. 17. Humanized 1F6 anti-CD70 antibody prolongs survival of mice in xenograft models of disseminated lymphoma and multiple myeloma. (A) Survival of mice injected with Raji cells and treated with humanized 1F6 antibody or control non-binding antibody. Treatment was initiated one day after tumor cell injection and was administered by intraperitoneal injection every four days for a total of six doses (n=10 per group). (B, C, left panels) Survival of mice injected with L363- or MM.1S-cells and treated with humanized 1F6 starting one day after cell implant. The antibody was administered by intravenous injection once weekly for a total of five doses. Mice were monitored twice weekly and were euthanized upon manifestation of disease (n=7 per group). (B, C, right panels) Analysis of λ light chain concentrations in sera collected from mice injected with L363- or MM.1S-cells. Samples were collected on days 35 and 42 post tumor injection, respectively. In all studies, p values given are between humanized 1F6-treated groups and the untreated group.

The results show that, in each tumor model (FIGS. 17A, 17B and 17C), survival of mice treated with humanized 1F6 was significantly prolonged compared to that of untreated mice or mice receiving non-binding control antibody. The effect of humanized 1F6 treatment was further evaluated in multiple myeloma xenografts (L363 and MM.1S cells) by measuring the level of tumor-derived monoclonal protein (λ light chain) in the sera of individual mice. As shown in FIGS. 17B and 17C (right panels), circulating λ light chain concentrations were significantly lower in mice treated with humanized 1F6 as compared to untreated mice. Mean serum levels of λ light chain in L363-bearing mice treated with humanized 1F6 were 0.006 μg/mL compared to 0.10 μg/mL in sera of untreated mice. Similarly, λ light chain levels in humanized 1F6-treated MM.1S-bearing mice were 0.03 μg/mL compared to 1.25 μg/mL in untreated mice. These results were consistent with the increased survival rates of the mice (FIGS. 17B and 17C, right panels).

Example 12

In Vitro Deletion of CD70 Antigen-Specific T Cells by Humanized 1F6 Antibody

To test the ability of humanized 1F6 antibody to deplete antigen-specific activated T cells, PBMC from a normal donor expressing HLA-A0201 were stimulated with the M1 peptide in the presence or absence of varying concentrations of humanized anti-CD70 antibody. Humanized 1F6 antibody was prepared as described above. PBMC were seeded in a 24-well plate at a concentration of 0.5×10$^6$ cells/ml with 5 μg/ml M1 peptide in 2 ml of medium supplemented with IL-2 and IL-15, as described supra (Example 5). On day 5, half of the culture supernatant was replaced with fresh cytokine-containing medium. On day 9, the percentage of antigen-reactive cells (the CD8$^+$/Vβ17$^+$ population) was determined by flow cytometric analysis of cells stained with FITC-conjugated anti-Vβ17- and PE-Cy5-conjugated anti-CD8 antibodies.

Figure 18:
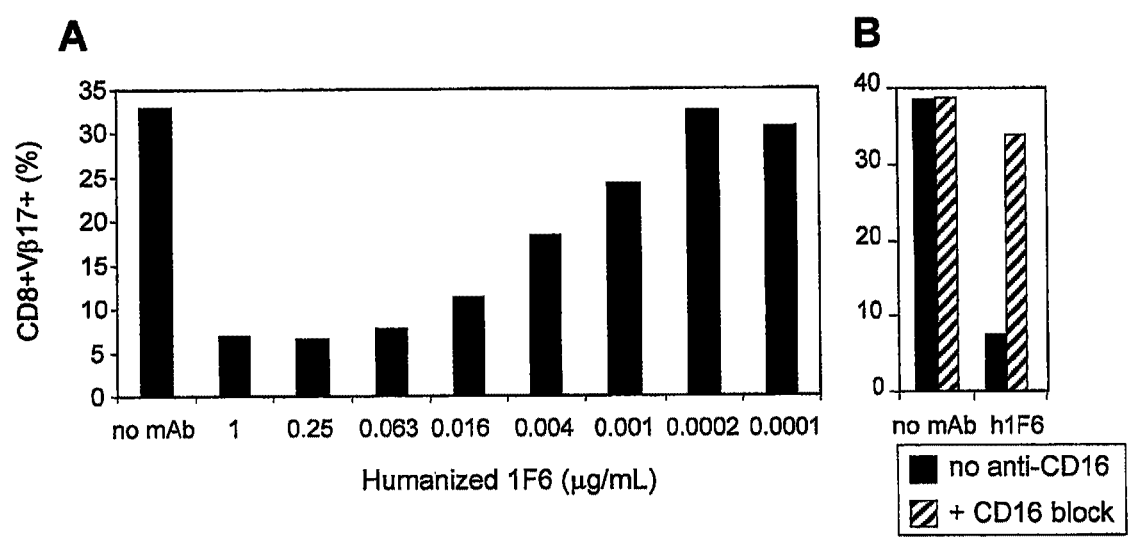
FIG. 18. Humanized 1F6 mediates depletion of antigen-specific CD8+/Vβ17+ cells. PBMCs from a normal HLA-A0201 donor were stimulated with the M1 peptide as described in Example 5. (A) Peptide-stimulated cultures were untreated or treated with concurrent addition of graded doses of humanized 1F6 antibody, as indicated. The percent CD8+/Vβ17+ cells after 9 days was determined by flow cytometry. (B) Peptide-stimulated cultures were untreated or treated on day 0 with 1 μg/ml humanized 1F6 in the absence (solid bars) or presence (hatched bars) of 10 μg/ml antibody specific for FcγRIII (CD16). The percent CD8+/Vβ17+ cells after 9 days was determined by flow cytometry.

FIG. 18A shows that antigen-specific CD8$^+$/Vβ17$^+$ cells expanded to comprise 33% of all viable cells within the culture in the absence of antibody. In contrast, addition of humanized 1F6 to the cultures on day 0 significantly limited expansion of the antigen-reactive population in an antibody-dose dependent manner. These results show that humanized 1F6 selectively targets and prevents the expansion of antigen-activated T cells.

In a second study (FIG. 18B), M1-peptide stimulated cultures were untreated or treated with humanized 1F6 in the absence or presence of antibody that specifically blocks FcγRIII (CD16). In untreated cultures, the antigen-specific CD8+Vβ17$^+$ population expanded to comprise 39% of all viable cells within the culture. Addition of humanized 1F6 significantly diminished expansion of the reactive population. This activity was largely reversed when FcγRIII receptors were blocked with anti-CD16 specific antibody, indicating that deletion of peptide-reactive cells was mediated via humanized 1F6 interaction with FcgRIII-bearing effector cells.

Example 13

Anti-CD70 Antibody does not Affect Antigen-Negative Bystander Cells

To determine the effect of 1F6-mediated depletion on antigen-negative bystander T cells, the TCR Vβ family representation of CD4 and CD8 lymphocytes was examined in M1-activated cultures that were untreated or treated with a chimeric variant of 1F6 (c1F6) (human IgG1 isotype) and compared to resting, non-antigen stimulated PBMC. Chimeric and humanized 1F6 variants are comparable in binding affinity, capacity to mediate effector functions, and ability to deplete activated CD8+ T cell subsets.

Figure 19:
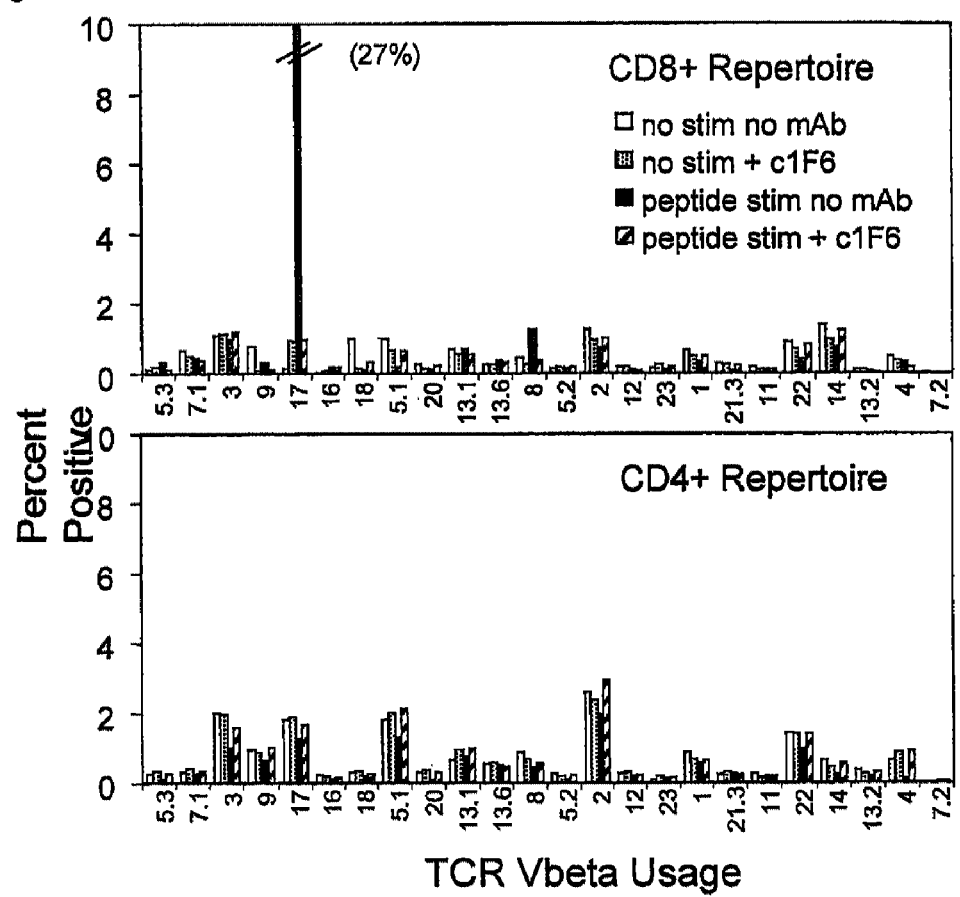
FIG. 19. Minimal impact of anti-CD70 1F6 antibody on bystander resting T cells. PBMCs from a normal HLA-A0201 donor were untreated (no stim) or stimulated with M1 peptide (peptide stim) in the presence or absence of 1 μg/mL c1F6. After nine days in culture, Vβ TCR representation among CD4 and CD8 cells from each group was analyzed by flow cytometry using the IOTest® Beta Mark TCR Vβ Repertoire Kit.

As shown in FIG. 19, stimulation of HLA-A0201+PBMC with M1 peptide caused the expansion of CD8+ cells bearing the Vβ17 TCR approximately 30-fold, whereas all other VβTCR families tested in CD8+ cells and all families tested in the CD4 cell population demonstrated minimal change. In the control population, cell expansion was limited to the Vβ17+CD8+ T cell subset, which increased from <1% of CD8+ cells to 27%; this observation confirms the specificity of the M1-peptide immune response. Unlike T cells stimulated in the absence of CD70-specific antibody, expansion of M1-peptide specific CD8+ cells was prevented by the addition of c1F6 to the culture. In the presence of c1F6 antibody, the percent Vβ17+CD8+ cells was comparable to that of resting, non-peptide stimulated cells. Treatment with c1F6 antibody did not significantly perturb the relative representations of other CD8+ or CD4+ Vβ TCR families; no group was observed to be eliminated. These data demonstrate that exposure to c1F6 selectively depletes CD70+ activated T cells without causing detectable collateral damage to bystander T cell populations.

Example 14

Treatment of Experimental Allergic Encephalomyelitis by Administration of Anti-CD70 Antibodies Studies indicate a role for CD70/CD27-mediated T cell-T cell interactions in enhancing the Th$_1$-mediated immune responses in cell-mediated autoimmune diseases, including, for example, autoimmune demyelinating diseases. In this example, experimental allergic encephalomyelitis (EAE), an animal model of the demyelinating disease multiple sclerosis (MS), is treated with a chimeric or humanized anti-CD70 antibody that recognizes an epitope of murine CD70 corresponding the 1F6 epitope of human CD70.

Induction and clinical assessment of Experimental Allergic Encephalomyelitis (EAE): R-EAE (relapsing EAE) is induced in six- to seven-week-old female SJL mice by subcutaneous immunization with 100 µl of complete Freund's adjuvant (CFA) emulsion containing 200 µg of *Mycobacterium tuberculosis* H37Ra and 40 µg of the immunodominant epitope of proteolipid protein, PLP$_{139-151}$. The signs of EAE are scored on a 0 to 5 scale as follows: (0) normal; (1) limp tail or hind limb weakness; (2) limp tail and hind-limb weakness (waddling gait); (3) partial hind-limb paralysis; (4) complete hind-limb paralysis; and (5) moribund. A relapse is defined as a sustained increase (more than 2 days) in at least one full grade in clinical score after the animal had improved previously at least a full clinical score and had stabilized for at least 2 days. The data are plotted as the mean clinical score for all animals in a particular treatment group or as the relapse rate (total number of relapses in a group divided by the total number of mice in that group).

Anti-CD70 Administration Regimens: Anti-CD70 antibody (0.1-3 mg/kg body weight) is administered intraperitoneally in a total volume of 100 µl. Mice are treated 3 times per week for 3 consecutive weeks (9 total treatments). Treatment is initiated before disease onset (day 7) or at the peak of acute disease (day 14). As a control, one group of EAE-induced mice are left untreated.

Inhibition of TNF-α and IFN-γ induction: Demonstration of the presence of TNF-α and IFN-γ in the brains of mice with EAE shows an inflammatory disease process indicative of EAE disease progression. Inhibition of the induction of these cytokines in the brains of SJL mice treated with anti-CD70 antibody indicates the value of anti-CD70 antibody therapy in preventing or treating EAE. Brains are obtained from at least three animals treated preclinically (at day 13, after three treatments, and day 26, after nine treatments) and at peak of acute disease (at day 20, after three treatments, and day 33, after nine treatments). Brains are fixed (10% buffered formalin), and tissues are embedded in paraffin and sectioned. Sections are then independently stained for TNF-α or IFN-γ by incubation with a primary antibody specific for the respective cytokine, followed by incubation with a secondary antibody conjugated to FITC. Tissue sections are then mounted in mounting media and analyzed by immunofluorescence microscopy. Decreased TNF-α or INF-γ staining in anti-CD70 antibody-treated mice versus the untreated EAE-induced mice shows inhibition of inflammatory cytokine induction using anti-CD70 antibody therapy.

Inhibition of Disease Symptoms or Relapse Rates: EAE-induced SJL mice in the anti-CD70 antibody treatment group are compared with untreated EAE-induced mice to assess the efficacy of anti-CD70 antibody therapy in either preventing disease onset or treating established disease. For mice treated preclinically, a decrease in the mean score for EAE disease, as compared to the untreated control group, demonstrates the efficacy of anti-CD70 antibody therapy in preventing disease. For mice treated at the peak of acute disease, either (a) a decrease in the relapse rate or (b) a decrease in the post-treatment mean score for EAE, as compared to the untreated control group, demonstrates the efficacy of anti-CD70 antibody therapy in treating established disease.

Example 15

Treatment of Graft Versus Host Disease by Administration of Anti-CD70 Antibodies The hu-SCID model has proven to be an effective system for investigating human immunological diseases. In this model of graft versus host disease, the effects of anti-CD70 antibodies on human PBLs and/or PBMCs are studied.

Establishment of Human Immune Cells in Immunodeficient Mice: Prior to injection of human PBL or PBMC, the following effector cells are depleted in the mice with the indicated reagents: for Natural Killer (NK) cells, e.g., anti-asialo-GM1 or TMB-1 antibody; for macrophages/monocytes, e.g., chlodronate encapsulated liposomes; for neutrophils, e.g., anti-Gr-1 antibody; for complement, e.g., cobra venom factor. Human PBL or PBMC ($1-30\times10^7$) are transplanted into SCID mice (female CB.17-SCID, SCID-NOD, or CB.17-SCID/beige mice, 8-12 weeks old) to establish a stable long-term reconstitution of a functional human immune system in the mice.

Human cell engraftment in SCID mice is assessed by analyzing sera for the presence human immunoglobulin during the experiment. Engraftment efficiency is also measured by human cell counts in blood, peritoneal exudates, and spleens of anesthetized or euthanized animals throughout the study. Upon successful establishment of human cell engraftment, the mice are treated with anti-CD70 antibody (1-10 mg/kg body weight, given intraperitoneally or intravenously, four-seven doses every four to seven days). The effects of antibody or antibody conjugate treatment on human cells is investigated by examining the numbers of the human cells in mouse blood and/or spleen taken at different days (1, 4, 7, 14, and 28) after treatment.

Collection of tissues: At specific time points post injection and at the end of the experiment, the following tissues are collected and analyzed for disease progression and cellular infiltration from euthanasized mice: spleen, lymph nodes, thymus, liver, bone marrow, lung, brain, intestine, colon, skin, pancreas, peritoneal exudate, and blood.

Example 16

Treatment of Asthma by Administration of Anti-CD70 Antibodies

The efficacy of anti-CD70 antibody was investigated in a murine model of asthma. Balb/c mice were treated with 10 mg OVA/Alum for sensitization at days 0, 7 and 14. An anti-murine CD70 antibody (clone 3B9) at a dose of 10 mg/kg body weight, was administered intraperitoneally Q7dx4 starting at day 0. The mice were then challenged with 5% aerosolized ovalbumin at days 21, 22, and 23. On day 26, the mice were sacrificed and the bronchioalveolar lavage fluid, blood, draining lymph nodes, spleen, and lung were collected. The results obtained indicated a milder cellular infiltration to the lung in the 3B9 treated group in comparison to the control group.

Example 17

Expression of CD70 on Multiple Myeloma Cell Lines

Cell surface CD70 expression was evaluated in a panel of multiple myeloma cell lines (Table 2). The copy number of CD70 molecules expressed by each cell line was determined by quantitative flow cytometry using the QIFIKit® (Dako, Carpinteria, Calif.).

TABLE 2

CD70 receptor number on Multiple Myeloma Cell Lines

| Cell Line | CD70 copies/cell |
| --- | --- |
| MM.1S | 14,000 |
| MM.1R | 25,000 |
| AMO-1 | 92,000 |
| JJN-3 | 19,000 |
| L363 | 13,000 |
| LB | 45,000 |
| U266 | 155,000 |
| LP-1 | 34,000 |
| MOLP-8 | 9,000 |

Example 18

Expression of CD70 on Hodgkin's and Glioblastoma Cell Lines

Cell surface CD70 expression was also evaluated in panels of Hodgkin's disease (Table 3) and glioblastoma cell lines (Table 4). The copy number of CD70 molecules expressed by each cell line was determined by quantitative flow cytometry using the QIFIKit® (Dako, Carpinteria, Calif.).

TABLE 3

Expression of CD70 on Hodgkin's Disease Cell Lines

| Cell Line | CD70 copies/cell |
| --- | --- |
| RPMI-6666 | 21,000 |
| Hs445 | 64,000 |
| L428 | 105,000 |
| KMH2 | 160,000 |
| SUP-HD-1 | 221,000 |

TABLE 5

Expression of CD70 on Glioblastoma Cell Lines

| Cell Line | CD70 copies/cell |
| --- | --- |
| U251 | 117,000 |
| SNB-19 | 90,000 |
| U373MG | 70,000 |
| GMS-10 | 64,000 |
| DBTRG-05MG | 59,000 |

\* \* \*

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Various references, including patent applications, patents, and scientific publications, are cited herein, the disclosures of each of which is incorporated herein by reference in its entirety.

What is claimed is:

1. A method for the treatment of a CD70-expressing non-Hodgkin's lymphoma in a subject, comprising:
   administering to the subject an effective amount of an antibody having an antigen-binding region that binds to CD70 and at least one effector domain mediating at least an ADCC, ADCP or CDC response in the subject, wherein the antibody exerts a cytostatic or cytotoxic effect in the absence of conjugation to a therapeutic agent and wherein the antibody is not conjugated to a therapeutic agent,
   wherein the CD70-expressing non-Hodgkin's lymphoma is a mantle cell lymphoma.

2. The method of claim 1, wherein the antibody is a chimeric, humanized, or fully human antibody.

3. The method of claim 2, wherein the antibody is a humanized antibody.

4. The method of claim 3, wherein the humanized antibody comprises an effector domain of a human IgM or IgG antibody.

5. The method of claim 4, wherein the IgG antibody is of the human IgG1 subtype.

6. The method of claim 2, wherein the antibody is a chimeric antibody.

7. The method of claim 6, wherein the chimeric antibody comprises an effector domain of a human IgM or IgG antibody.

8. The method of claim 7, wherein the IgG antibody is of the human IgG1 subtype.

9. The method of claim 2, wherein the antibody comprises a human constant region.

10. The method of claim 1, wherein the antibody comprises H1, H2, H3, L1, L2 and L3 complementarity-determining regions having, respectively, the amino acid sequences set forth in SEQ ID NO:6, SEQ ID NO:8, SEQ ID NO:10; SEQ ID NO:16, SEQ ID NO:18, and SEQ ID NO:20.

11. The method of claim 1, wherein the antibody comprises a heavy chain variable region having the amino acid sequence set forth in residues 20-137 of SEQ ID NO:2 or residues 20-137 of SEQ ID NO:22.

12. The method of claim 11, wherein the antibody-further comprises a light chain variable region having the amino acid sequence set forth in residues 21-132 of SEQ ID NO:12 or residues 21-132 of SEQ ID NO:32.

13. The method of claim 1, wherein the antibody comprises a light chain variable region having the amino acid sequence set forth in residues 21-132 of SEQ ID NO:12 or residues 21-132 of SEQ ID NO:32.

14. The method of claim 10, wherein the antibody is a humanized antibody.

15. The method of claim 10, wherein the antibody is a chimeric antibody.

16. The method of claim 1, wherein the antibody is multivalent.

17. The method of claim 1, further comprising administering a therapeutic agent.

18. The method of claim 17, wherein the therapeutic agent is a cytostatic, cytotoxic or immunomodulatory agent.

19. The method of claim 18, wherein the therapeutic agent is a cytostatic or cytotoxic agent.

20. The method of claim 1, wherein the subject is human.

21. The method of claim 1, wherein the antibody comprises H1, H2, and H3 complementarity determining regions having the amino acid sequences set forth in SEQ ID NO:26, SEQ ID NO:28 and SEQ ID NO:30, respectively, and further comprises L1, L2, and L3 complementarity determining regions having the amino acid sequences set forth in SEQ ID NO:36, SEQ ID NO:38 and SEQ ID NO:40, respectively.

22. The method of claim 1, wherein the antibody competes for binding to CD70 with a second antibody comprising a heavy chain variable region having the amino acid sequence set forth in residues 20-137 of SEQ ID NO:2 and a light chain variable region having the amino acid sequence set forth in residues 21-132 of SEQ ID NO:12.

23. The method of claim 22, wherein the antibody is a chimeric, humanized, or fully human antibody.

24. The method of claim 23, wherein the antibody is a humanized antibody.

25. The method of claim 24, wherein the humanized antibody comprises an effector domain of a human IgM or IgG antibody.

26. The method of claim 25, wherein the IgG antibody is of the human IgG1 subtype.

27. The method of claim 22, wherein the antibody comprises a human constant region.

28. The method of claim 1, wherein the antibody competes for binding to CD70 with a second antibody comprising a heavy chain variable region having the amino acid sequence set forth in residues 20-137 of SEQ ID NO:22 and a light chain variable region having the amino acid sequence set forth in residues 21-132 of SEQ ID NO:32.

* * * * *

UNITED STATES PATENT AND TRADEMARK OFFICE
CERTIFICATE OF CORRECTION

PATENT NO. : 8,337,838 B2
APPLICATION NO. : 12/370151
DATED : December 25, 2012
INVENTOR(S) : Che-Leung Law, Julie McEarchern and Alan F. Wahl Page 1 of 1

It is certified that error appears in the above-identified patent and that said Letters Patent is hereby corrected as shown below:

On the title page, item (60), Line 1, after "application" insert --No. 60/792,132, filed on Apr. 13, 2006, provisional application No.--

In the Claims:

Claim 10, Column 73, Line 35, after "in" delete "SEQ ID NO:6" and insert --residues 45-54 of SEQ ID NO:2--

Claim 12, Column 73, Line 41, after "antibody" delete "-" and insert a space before "further"

Signed and Sealed this
Twenty-third Day of April, 2013

Teresa Stanek Rea
*Acting Director of the United States Patent and Trademark Office*